United States Patent [19]
Allington et al.

[11] Patent Number: 5,635,070
[45] Date of Patent: Jun. 3, 1997

[54] APPARATUS AND METHOD FOR SUPERCRITICAL FLUID EXTRACTION

[75] Inventors: Robert W. Allington; Daniel G. Jameson, both of Lincoln; Dale A. Davison, Greenwood; Dale Clay, Lincoln, all of Nebr.; Robin R. Winter, Newburg, Oreg.; Yoossef Tehrani, Lincoln, Nebr.

[73] Assignee: Isco, Inc., Lincoln, Nebr.

[21] Appl. No.: 208,121

[22] Filed: Mar. 8, 1994

Related U.S. Application Data

[60] Continuation-in-part of Ser. No. 134,033, Oct. 8, 1993, abandoned, which is a division of Ser. No. 27,257, Mar. 5, 1993, Pat. No. 5,268,103, which is a continuation-in-part of Ser. No. 908,458, Jul. 6, 1992, Pat. No. 5,198,197, which is a division of Ser. No. 795,987, Nov. 22, 1991, Pat. No. 5,160,624, which is a continuation-in-part of Ser. No. 553,119, Jul. 13, 1990, Pat. No. 5,094,753.

[51] Int. Cl.[6] ................................................. B01D 11/00
[52] U.S. Cl. ........................................ 210/634; 210/416.1
[58] Field of Search ............................... 210/634, 511, 210/416.1; 60/3.2; 417/228

[56] References Cited

U.S. PATENT DOCUMENTS 5,180,293  1/1993  Hartl ........................................ 417/366

*Primary Examiner*—Frank Spear
*Attorney, Agent, or Firm*—Vincent L. Carney

[57] ABSTRACT

To pump supercritical carbon dioxide into a supercritical extractor without overpressure in the reservoir and to record the volume being delivered, the pumping speed is controlled and the volume pumped is determined from a pressure-related signal used in a feedback circuit. The feedback controls the velocity of pumping in conjunction with programmed values to avoid destructive reverse torque. A cam in the pump controls piston stroke, has a depressurization portion with an initial slope equal to but in the opposite direction of the final slope, rounded transition slopes, increasing linear velocity to the refill portion and constant velocity in the refill portion.

6 Claims, 15 Drawing Sheets

APPARATUS AND METHOD FOR SUPERCRITICAL FLUID EXTRACTION

RELATED CASE

This application is a continuation-in-part application of U.S. patent application Ser. No. 08/134,033 filed Oct. 8, 1993, now abandoned, which is a divisional application of U.S. patent application Ser. No. 08/027,257 filed Mar. 5, 1993, now U.S. Pat. No. 5,268,103, which is a continuation-in-part application of U.S. patent application Ser. No. 07/908,458 filed Jul. 6, 1992, now U.S. Pat. No. 5,198,197, which is a divisional application of U.S. patent application Ser. No. 07/795,987 filed Nov. 22, 1991, now U.S. Pat. No. 5,160,624, which is a continuation-in-part application of U.S. patent application Ser. No. 07/553,119 filed Jul. 13, 1990, now U.S. Pat. No. 5,094,753 for APPARATUS AND METHOD FOR SUPERCRITICAL FLUID EXTRACTION.

BACKGROUND OF THE INVENTION

This invention relates to supercritical fluid extraction and more particularly relates to a reciprocating pump for pumping liquid near its supercritical temperature in such systems.

In supercritical fluid extraction, an extraction vessel is held at a temperature above the critical point and is supplied with fluid at a pressure above the critical pressure. Under these conditions, the fluid within the extraction vessel is a supercritical fluid. In one type of apparatus for supercritical extraction, there is a specially constructed extraction vessel within a source of heat and a specially constructed pump for supplying supercritical fluid to the extraction vessel.

One prior art type of pump used for supercritical extraction is the same as a single piston pump used for HPLC. This type of pump has several disadvantages when used for supercritical fluid extraction, which are: (1) a regenerative effect may, under some circumstances, be created in which the heat of compression increases the temperature of the fluid and which in turn increases its compressibility and causes the regenerative effect, which prevents the accurate prediction of flow rate for purposes of control; (2) the usual cams create destructive reverse torques on the pumping cam, gear train and drive motor after the cam passes top dead center because the high compressibility of the liquid in the pump chamber causes the storing of a relatively high amount of energy at high pressures.

Another prior art pump used for supercritical fluid extraction is a multiple cylinder pump of the type now used in HPLC to reduce pulsation. This type of pump, besides being sometimes under some circumstances subject to the problems of single cylinder pumps, is also more expensive and complicated.

In still another prior art pump, a cam for driving the piston that is to pump a supercritical fluid has a slow return stroke intended to reduce destructive forces. This type of pump has a disadvantage insofar as it causes pulsations and delays on time during which fluid is not delivered.

In the prior art pumps, water cooling is usually used or the pumps have very low flow rates. Other prior art discloses cooling of either the inlet fluid or the pumphead. Such prior art discloses cooling just one but not the other. In U.S. Pat. No. 5,087,360, there is disclosed a supercritical fluid extraction system in which both the inlet fluid and pumphead are cooled, but water cooling is used for both.

In supercritical fluid extraction pumps, determination of actual fluid flow rate is a significant problem due to the very high compressibility of fluids used for supercritical applications such as carbon dioxide. The critical temperature of $CO_2$ is 31.1 degrees C, not much above room temperature. It is difficult to pump fluids near their critical point, a problem not encountered with HPLC pumps. The density of the approximately room temperature liquid (not yet supercritical fluid) leaving the pump is about 1¼ times that of the density of the fluid entering the pump: the compressibility of liquid carbon dioxide is about 1¼ to 1 from 870 psi to 7,500 psi. This compressibility is greater than the liquids used for HPLC. The high compressibility produces an unfortunate regenerative effect. The heat of compression raises the temperature of the fluid, which in turn makes it more compressible. This in turn raises the heat of compression further. The existence of this process makes a priori accurate prediction of flow rate impossible. The prior art cams for driving the plunger of a single-plunger pump for pumping highly compressible liquids such as in a liquid fluid supply for a supercritical extractor have a profile similar to that used in high performance liquid chromatography (HPLC) pumps. However, when using this profile highly compressible fluids at high pressure produce an undesirable and possible destructive reverse torque on the pumping cam, gear train and drive motor after the cam passes top dead center. This is because the high compressibility of the liquid in the pump chamber results in the storage of a relatively large amount of energy at high pressure such as 7500 psi.

One conventional solution to this problem is to use a cam with a slow return stroke. However, the slow return stroke takes up a lot of the cam rotation and it is obvious that liquid can not be delivered from the pump during the return stroke. This causes undesirable mechanical stress in and flow pulsations from the single-plunger pump.

Another conventional solution to this problem is to use a two or more plunger pump as this inherently reduces the pulsations and reduces the reverse torque on the mechanical system since when one head is depressurizing the other pumphead is delivering and is taking up positive torque which subtracts from the reverse torque of the pump it is depressurizing. However, this fix is undesirable because adding a second pumphead decreases reliability because of the increased number of parts and increases the cost of the pump for the same reason.

SUMMARY OF THE INVENTION

Accordingly, it is an object of the invention to provide a novel supercritical extraction technique.

It is a still further object of the invention to provide a novel supercritical extraction apparatus.

It is a still further object of the invention to provide a novel pump and pumping technique.

It is still further object of the invention to provide a novel technique for measuring volumetric flow rate.

It is a still further object of the invention to provide a novel technique for controlling the temperature of fluids used in supercritical fluid extraction.

It is a still further object of the invention to provide a novel supercritical extraction technique which is able to use less expensive containers for samples to be extracted than prior techniques.

It is a still further object of the invention to provide a novel supercritical extraction apparatus and method in which a series of samples may be automatically processed with a minimum of handling by an operator.

It is a still further object of this invention to provide a novel reciprocating pump intended for pumping highly compressible liquids such as liquid carbon dioxide near its critical point with a minimum pulsation and maximum efficiency and reliability to a pressure of up to 7500 psi (pounds per square inch).

It is a still further object of this invention to provide a novel technique for pumping highly compressible liquids to pressures up to 7500 psi with a single-head pump.

It is a still further object of this invention to provide a novel technique for pumping liquid carbon dioxide from a supply vessel at a temperature below 30° and at a pressures as low as the vapor pressure of the liquid carbon dioxide at the temperature to a pressure up to at least 7500 psi without use of a circulating coolant liquid.

It is a still further object of this invention to provide a novel technique for pumping highly compressible liquids at a temperature close to the critical temperature without requiring a fluid coolant loop.

It is a still further object of this invention to provide a novel technique for improving the performance of a pump for pumping highly-compressible, low-boiling-point fluids by providing both the pumphead and a pump inlet heat exchanger with air-cooled thermoelectric coolers.

It is a still further object of the invention to provide a novel technique for pumping liquid with a temperature near its critical temperature to an outlet pressure of at least 7500 psi and an outlet flow rate in excess of 10 ml per minute.

It is a still further object of this invention to provide a novel plunger type pump whose plunger is supported concentrically with respect to its seal by a support bearing which lies in the same block of metal as the gland housing the seal.

It is a still further object of the invention to provide a novel means for accurately measuring the volume of highly compressible liquid being pumped to a high pressure.

It is a still further object of this invention to provide a novel technique for determining the delivered fluid volume of a pump which pumps a very compressible liquid to a high pressure and using this known delivered fluid volume to form composition gradients by either high pressure or low pressure mixing of two or more fluids.

It is a still further object of this invention to provide a novel liquid $CO_2$ pump that pumps liquid $CO_2$ from a reservoir pressurized only by the vapor pressure of the liquid $CO_2$ without the use of helium overpressure in the reservoir to a higher pressure suitable for supercritical fluid extraction.

In accordance with the above and further objects of the invention, a supercritical fluid extraction system includes a cartridge capable of holding the sample to be extracted, a pressure vessel into which the cartridge fits, a pumping system and a collection system. The pressure vessel fits into a heater and the cartridge is removably mounted to a breech plug that seals the pressure vessel. There are separate outlets for the cartridge and pressure vessel to permit equalization of pressure on the inside and outside of the cartridge without contamination from impurities outside the cartridge but inside the pressure vessel. A specially designed pump for the supercritical extraction system is a cam-driven single-plunger pump having a cam profile that enables the pumping system to avoid destructive reverse torque on the cam, gear train and drive motor after the cam passes top dead center.

The fluid volume leaving the pump is determined by measuring only pressure or other parameter related to flow and movement of the plunger. Measurement of the fluid volume leaving the pump is useful for recording or indicating the flow rate while the pump is operating as follows: (a) recording or indicating the flow volume or flow rate of the pump when the pump is operating at constant pressure; and (b) useful as feedback means for controlling the pump to provide constant flow.

The fluid delivery volume or actual flow rate provides signals used for accurate formation of either high pressure (outlet side) or low pressure (inlet side) composition gradients.

The pumphead and the inlet fluid are air-thermoelectrically cooled separately and simultaneously. It is surprising that air heat rejection is satisfactory as previous designs are water cooled or have very low flow rates. Also, there are surprising advantages over cooling just one but not the other as described in prior literature.

The plunger or piston of the pump is supported on both sides of the seal to lengthen the seal life by improving the alignment of the plunger within the seal. The plunger support within the pumphead is the controlling locator of the seal and is machined concentric and collinear to the seal gland. This construction which increases seal life is particularly useful because pump head cooling makes seal replacement more difficult.

In an automatically operated supercritical fluid extraction, programmable valves are caused to open and close to control the flow of high pressure fluids into the pressure chamber of a supercritical fluid extractor. For this purpose, a valve is provided having a valve seat that receives a spherical or ball-shaped valve element and a valve stem that is moved reciprocally to force the valve element into the seat or to release it. The ball is free to rotate upon being released and the supercritical fluid flows past the ball through the seat and into the pressure vessel.

In the preferred embodiment, the reciprocating stem that forces the valve element to close or releases it is controlled by a program controlled rotary motor. The reciprocating stem is connected to a rotary element that moves up and down to move the stem but does not cause the stem to rotate with it but only causes it to reciprocate.

To automate the operation under the control of a microprocessor, a motor operated fraction collector, a motor operated sample source and a motor operated sample injector automatically move samples and collection containers into an extraction station, inject samples into the extraction pressure vessel, perform extraction and collect extractant in different appropriate collection containers in a timed sequence to permit extracting of a series of samples with minimum human handling.

In the preferred embodiment, a movable motor member is aligned: (1) with an opening in a sample cartridge reel that moves sample cartridges carrying samples into the extraction station; and (2) with an opening in the extraction pressure vessel. The movable member is dimensioned to be capable of sealing a correspondingly sized opening in the pressure vessel and adapted to move the sample cartridge into the pressure vessel and seal the pressure vessel.

As can be understood from the above description, the supercritical extraction technique has several advantages, such as for example: (1) it is more convenient than prior art extractors; (2) it automates the sample injection and fraction collection part of the extraction process as well as automating the extraction itself; (3) it is smaller and more compact because of the air-thermoelectric cooling the pumphead and the inlet fluid separately and simultaneously; (4) it may have a reasonably high flow rate; (5) seal life is lengthened by improving the alignment of the plunger within the seal; (6) fluid volume leaving the pump is precisely measured; and (7) no water cooling is required.

DESCRIPTION OF THE DRAWINGS

The above noted and other features of the invention will be better understood from the following detailed description when considered with reference to the accompanying drawings in which.

DETAILED DESCRIPTION

Figure 1:
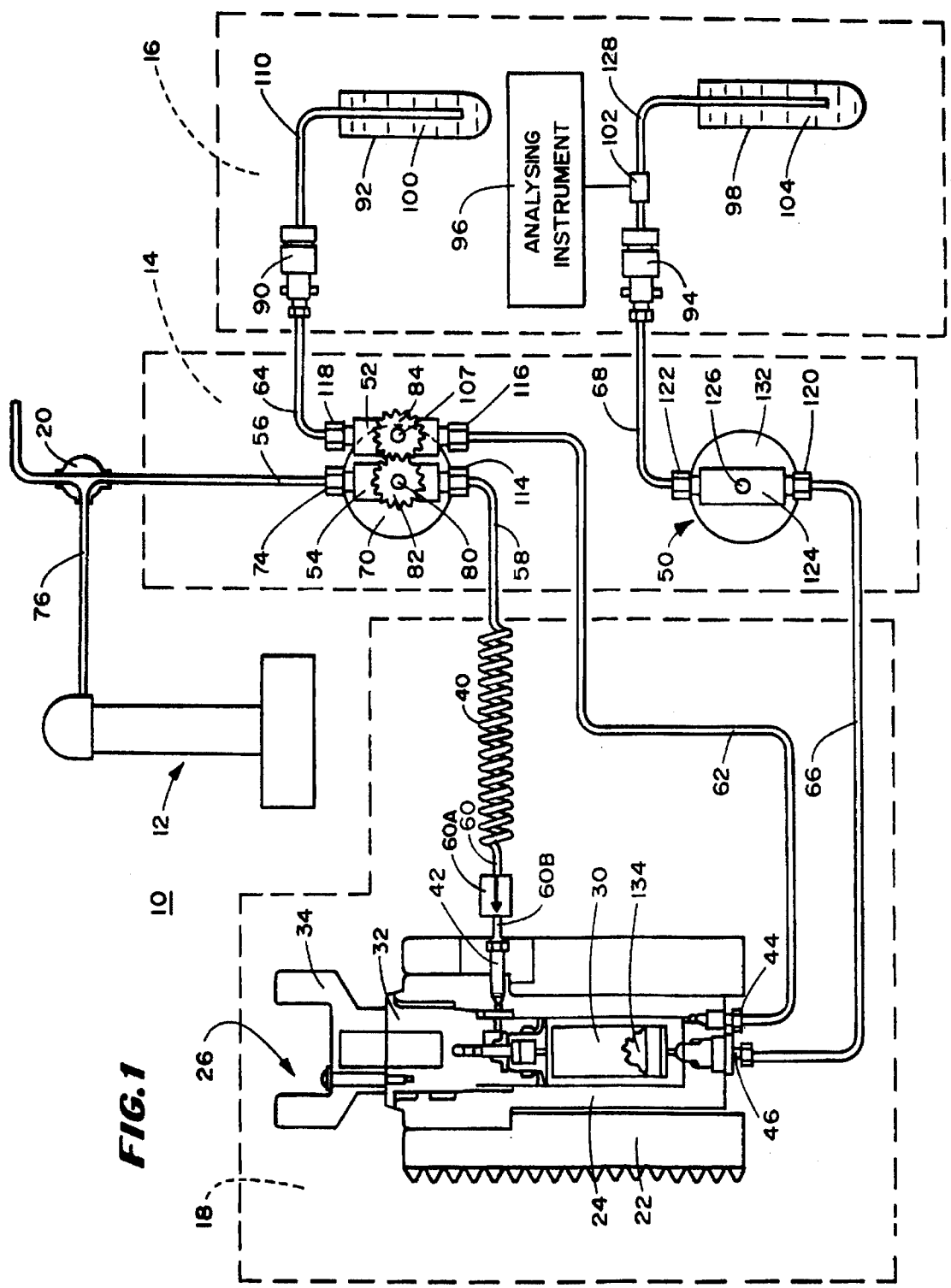
FIG. 1 is a schematic diagram illustrating the operation of a single supercritical fluid extraction system according to the invention.

In FIG. 1, there is shown a schematic fluidic diagram of one channel of a dual-channel supercritical fluid extraction system 10 having a pumping system 12, a valve system 14, a collector system 16 and a pressure vessel and fluid-extraction assembly 18. The pumping system 12 communicates with two extraction cartridges within the pressure vessel and fluid-extraction assembly 18 and for this purpose is connected through a tee joint 20 to two identical valve systems, one of which is shown at 14. Each valve system communicates with a different one of two inlets for the corresponding one of two extraction cartridges.

A specially designed pump (not shown in FIG. 1) for the supercritical extraction system is a cam-driven single-plunger pump having a cam profile that enables the pumping system to avoid destructive reverse torque on the cam, gear train and drive motor after the cam passes top dead center.

The fluid volume leaving the pump is determined by measuring only pressure or other parameter related to flow and movement of the plunger. Measurement of the fluid volume leaving the pump is useful for recording or indicating the flow rate while the pump is operating as follows: (a) recording or indicating the flow volume or flow rate of the pump when the pump is operating at constant pressure; and (b) useful as feedback means for controlling the pump to provide constant flow.

The fluid delivery volume or actual flow rate provides signals used for accurate formation of either high pressure (outlet side) or low pressure (inlet side) composition gradients.

The pumphead and the inlet fluid are air-thermo-electrically cooled separately and simultaneously. It is surprising that air heat rejection is satisfactory as previous designs are water cooled or have very low flow rates. Also, there are surprising advantages over cooling just one but not the other as described in prior literature.

The plunger or piston of the pump is supported on both sides of the seal to lengthen the seal life by improving the alignment of the plunger within the seal. The plunger support within the pumphead is the controlling locator of the seal and is machined concentric and collinear to the seal gland. This construction which increases seal life is particularly useful because pump head cooling makes seal replacement more difficult.

The valve system 14 and a second valve system (not shown in FIG. 1) which is connected to the other branch of the tee joint 20 are each connected to two different collector systems 16, one of which is shown in FIG. 1, and to different ones of the two extraction cartridges in the pressure-vessel and fluid-extraction assembly 18 so that, two extraction operations can be performed at the same time using the same pumping system 12. With this arrangement, the valve system 14 causes: (1) supercritical fluid to flow from the pumping system 12 into a space between a cartridge and the interior of the pressure vessel of the pressure-vessel and fluid-extraction assembly 18 for purging the outside of the cartridge and the inside of the pressure vessel; and (2) applies supercritical fluid through the cartridge for extraction of a sample 134 therein. Because the fluid is applied both to the interior of the cartridge and the exterior, the cartridge does not have to withstand a high pressure difference between its interior and exterior and can be made economically.

In addition to controlling the flow of fluid into the pressure-vessel and fluid-extraction assembly 18, the valve system 14 controls the flow of: (1) purging supercritical fluid from the space between the cartridge and interior of the vessel to the collector system 16 or to a vent; and (2) the extractant from the interior of the cartridge to the collector system 16 for separate collection.

To hold sample 134 during an extraction process, the pressure-vessel and fluid-extraction assembly 18 includes a heating block 22, a pressure vessel 24 and a cartridge and plug assembly 26 with the cartridge and plug assembly 26 extending into the pressure vessel 24. The pressure vessel 24 fits within the heating block 22 for easy assembly and disassembly. With this arrangement, the heating block 22 maintains the fluids within the pressure-vessel and fluid-extraction assembly 18 at supercritical fluid temperature and pressure for proper extraction.

The cartridge and plug assembly 26 includes an extraction cartridge assembly 30, a breech plug 32 and a knob 34 which are connected together so that: (1) the pressure vessel 24 is easily sealed with the breech plug 32; (2) the extraction cartridge assembly 30 snaps onto the breech plug 32 and the assembly may be carried by the knob 34; and (3) the knob 34 serves as a handle to insert and fasten the assembly to the tube pressure vessel with the extraction tube communicating with an outlet aligned with its axis and an inlet for the space between the internal walls of the pressure vessel 24 and the exterior of the extraction cartridge 30 and for the interior of the extraction cartridge 30 being provided through a groove circumscribing the assembly inside the pressure vessel 24.

With this arrangement the extraction cartridge assembly 30 may be easily sealed in the pressure vessel 24 by threading the breech plug 32 into it and may be easily removed by unthreading the breech plug 32 and lifting the knob 34. The extraction cartridge assembly 30 contains a hollow interior, an inlet and an outlet so that a sample to be extracted may be placed in the hollow interior and supercritical fluid passed through the inlet, the hollow interior and to the outlet to a collector. The extraction cartridge assembly 30 serves as an extraction chamber or tube, the pressure vessel 24 serves as an extraction vessel and the heating block 22 serves as an oven as these terms are commonly used in the prior art.

In the preferred embodiment, the knob 34 is of a low heat conductivity material and it should include in all embodiments at least a heat insulative thermal barrier located to reduce heating of the handle portion of the knob 34. It extends outside of the pressure vessel 24 and is adapted to aid in the sealing of the pressure vessel 24 and the breech plug 32 together so that the extraction cartridge assembly 30 is within the pressure vessel 24 for maintaining it at the appropriate temperature and the knob 34 is outside the pressure vessel 24 so as to remain cool enough to handle.

Although in the preferred embodiment the knob 34 is a heat insulative material, it only needs to be insulated against heat conducted from the interior of the pressure vessel 24 and this may also be done by a thermal barrier separating the pressure vessel 24 from the knob 34 such as an insulative disc having a width of at least 1 millimeter and extending across the cross-section of the knob 34 to the extent of at least 80 percent of the cross-section to effectively block any considerable amount of transfer of heat between the cartridge and the knob 34. It should have a heat conductivity no greater than 0.05 calories/cm. sec. degree C at 30 degrees Centigrade.

The extraction cartridge assembly 30 has an opening which permits some supercritical fluid to enter the pressure vessel 24 to follow one path passing into the extraction tube and out through an outlet of the extraction tube into a conduit leading to a collector. Other supercritical fluid follows a second path around the outside of the cartridge to remove contaminants from the pressure vessel 24, equalize pressure and flow from another outlet. One of the inlet and outlet of the extraction cartridge assembly 30 enters along the central axis of the extraction cartridge assembly 30 and the other from the side to permit rotation of parts with respect to each other during seating of the pressure vessel 24 and yet permit communication of the extraction cartridge assembly 30 with the fluid source and with the collector. To reduce wasted heat and fluid, the space between the outside of the cartridge and the inside walls of the pressure vessel 24 is only large enough to accommodate the flow of purging fluid and to equalize pressure between the inside and outside of the cartridge. The volume between the outside of the cartridge and the inside of the pressure vessel 24 is less than 10 cubic centimeters.

In the preferred embodiment, the inlet opens into an annular space between the internal wall of the pressure vessel 24 and the cartridge and plug assembly 26. The fluid follows two paths from the annular space, both of which include an annular manifold with narrow holes and a passageway that communicates with the recess in the breech plug 32. One path opens into the extraction cartridge assembly 30. The other passes along the narrow space outside the extraction cartridge assembly 30. Thus, supercritical fluid enters the extraction tube through a labrythian like path and at the same time passes outside the extraction tube so that the pressure inside the extraction tube is always substantially the same as that inside the pressure vessel 24. Because the pressures are substantially the same, the tube itself may be formed of relatively inexpensive plastics notwithstanding that a high pressure is desirable for extraction from the sample within the extraction tube.

The pressure vessel 24 is generally formed of strong material such as metal and is shaped as a container with an open top, an inlet opening and two outlet openings. The inlet opening is sized to receive an inlet fitting 42, the inlet fitting 42 being shown in FIG. 1 connected in series with check valve 60A to corresponding heat exchanger 40. Each of the two outlet openings are sized to receive a different one of a corresponding purge valve fitting 44, and a corresponding extractant fluid fitting 46. With these fittings, the pressure vessel 24 is able to receive the cartridge and plug assembly 26 in its open end and permit communication between the cartridge and the extractant fluid fittings such as shown at 46. The inlet fittings such as shown at 42 and purge valve fitting, such as 44, permit communication with the inside of the pressure vessel 24.

To control the flow of fluids to and from the pressure vessel and fluid-extraction assembly 18, the valve system 14 includes an extractant valve 50, a purge fluid valve 52 and an extracting fluid valve 54.

To introduce extracting fluid into the pressure-vessel and fluid-extraction assembly 18, the extracting fluid valve 54 communicates with one branch of the tee joint 20 through tube 56 and with one end of the heat exchanger 40 through tube 58, the other end of the heat exchanger 40 communicating with the inlet fitting 42 through tube 60, check valve 60A and tube 60B. With these connections, the extracting fluid valve 54 controls the flow of fluid from the pumping system 12 through the heat exchanger 40 and the pressure vessel 24 through the inlet fitting 42.

To remove purge fluid from the pressure vessel 24, the purge fluid valve 52 communicates at one port with the purge valve fitting 44 through tube 62 and with its other port through tube 64 (not shown in FIG. 1) with the collector system 16 or with a vent (not shown) to remove fluid containing contaminants from the exterior of fluid extraction cartridge assembly 30 and the interior of the pressure vessel 24.

To remove extractant from the extraction cartridge assembly 30, the extractant valve 50 communicates at one of its ports through tube 66 with the extractant fluid fitting 46 and through its other port with the collector system 16 through tube 68 for the collecting of the extracted material, sometimes referred to as analyte or extractant, from the sample within the pressure vessel and fluid-extraction assembly 18.

For convenience, the valves 52 and 54 are mounted to be operated by a single manual control knob 70. To supply fluid to the valve system 14: (1) the tube 76 carries pressurized fluid from the pumping system 12 to tee joint 20; (2) another tube is connected to the top arm of tee joint 20 to carry pressurized fluid to another liquid extraction system unit not shown on FIG. 1; and (3) the remaining arm of the tee joint 20 is connected through the tube 56 to an inlet fitting 74 of extracting fluid valve 54. The valves 50, 52 and 54 may be SSi type 02-0120.

The extracting fluid valve 54 has a rotary control shaft 80 that is rotated to open and close its internal port. This shaft is operated by hand control knob 70 and carries spur gear 82 pinned to the control shaft 80. Spur gear 84, which is pinned to control shaft 107 of purge fluid valve 52, meshes with spur gear 82 so that when control knob 70 is rotated clockwise, extracting fluid valve 54 is closed, but since the control shaft 107 of purge fluid valve 52 is geared to turn in the opposite direction, the clockwise rotation of knob 70 opens purge fluid valve 52.

The relative locations of the two gears on the two shafts are such that, in the first (clockwise) position of the knob 70, the extracting fluid valve 54 is shut and the purge fluid valve 52 is open. Turning the control knob 70 counterclockwise 130 degrees from this first position opens extracting fluid valve 54 while allowing purge fluid valve 52 to remain open. Thus, both valves are open when the knob 70 is rotated 130 degrees counterclockwise from the first position. When the knob 70 is rotated 260 degrees counterclockwise from the first position, extraction fluid valve 54 is open and purge fluid valve 52 is shut. Thus, there are three definable positions for control knob 70: (1) clockwise with valve 54 shut and valve 52 open; (2) mid position with both valves open; and (3) full counterclockwise with valve 54 open and valve 52 shut.

The extractant valve 50 includes an inlet fitting 120, outlet fitting 122, manual control knob 132 and control shaft 126. The rotary control shaft 126 is attached to control knob 132. When the extractant valve 50 is opened by turning the control knob 132 counterclockwise from its closed position, fluid flows from the extraction cartridge assembly 30, through the extractant fluid fitting 46, the conduit 66, the valve inlet fitting 120, the outlet fitting 122, through the tube 68 and into the collector system 16.

The collector system 16 includes a purge coupling 90, a purge fluid collector 92, an extractant coupling 94, an analyzing instrument 96, and an extractant fluid collector 98. The purge fluid flowing through the valve 52, flows through purge coupling 90 into the capillary tube 110 and from there into the purge fluid collector 92 where it flows into a solvent 100. Similarly, the extractant flowing through valve 50 flows through tube 68 to the extractant coupling 94 and from there to the capillary tube 128 and extractant fluid collector 98 which contains an appropriate solvent 104 in the preferred embodiment.

The analyzing instrument 96 may be coupled to the capillary tube 128 through an optical coupling 102 in a manner known in the art. The optical coupling 102 is a photodetector and light source on opposite sides of a portion of the capillary tube 128, which portion has been modified to pass light. This instrument 96 monitors extractant and may provide an indication of its passing into the extractant fluid collector 98 and information about its light absorbance. Other analytical instruments may also be used to identify or indicate other characteristics of the extractant.

Figure 2:
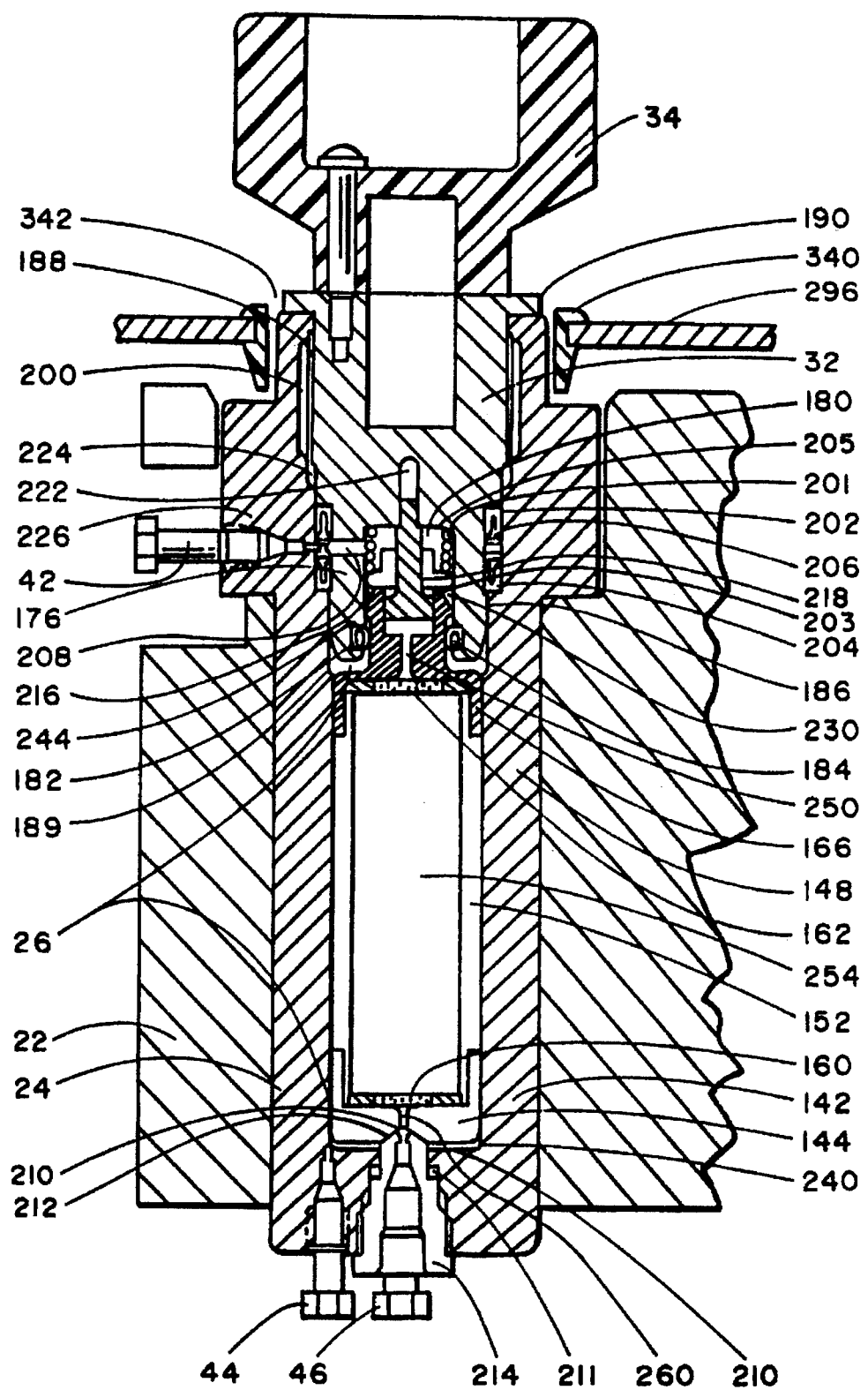
FIG. 2 is a fragmentary sectional view of the extraction cartridge, breech plug pressure vessel and heating block.

In FIG. 2, there is shown a sectional view of the clipped-together extraction cartridge 26, knob 34 and breech plug 32 replaceably installed in pressure vessel 24 which in turn has previously been permanently force fit into heating block 22. The pressure vessel 24 is fabricated of type 303 stainless steel for good machinability and corrosion resistance and has within it a cylindrical central opening sized to receive the extraction cartridge 26, two openings for outlet fittings in its bottom end, an opening in its cylindrical side wall to receive an inlet fitting and an open top with internal threads sized to engage the external threads 188 of the breech plug 32. The heating block 22 is fabricated from aluminum for good thermal conductivity and includes a cylindrical opening sized to tightly receive the pressure vessel 24. The breech plug 32 and the extraction cartridge assembly 30 are a slip fit within the pressure vessel 24. External threads 188 on breech plug 32 engage in internal threads 200 within pressure vessel 24.

An annular self-acting high pressure seal 202 cooperates with a sealing surface 186 to seal high pressure supercritical fluid from the atmosphere and an annular low pressure seal 204 spaced from the annular high pressure seal 202 prevents contaminated supercritical fluid in the space between the interior of the pressure vessel 24 and the exterior of the extraction cartridge assembly 30 from getting back to the supercritical fluid supply. These two annular seals 202 and 204 form between them a toroidal inlet chamber into which the outlet of the fluid inlet 42 extends to introduce fluid. Contamination may arise from fingerprints or other foreign material on the outside wall of extraction cartridge assembly 30 and the low pressure seal 204 protects against this contamination. Seals 202 and 204 are Bal-Seal type 504MB-118-GFP.

Supercritical fluid is supplied to fluid inlet 42 and circulates in the annular space between high pressure seal 202 and low pressure seal 204, and then follows two paths into the pressure vessel 24 and extraction cartridge 30: one path for purging and one path for extraction. An annular spacer 206 within the torroidal opening between seals 202 and 204 has an hour-glass shaped cross section with radial holes through it and distributes incoming supercritical fluid from the inlet of fitting 42 to the opposite side of the spacer 206 from which it flows to passageway 208 drilled in breech plug 32.

Because the passageway 208 extends radially from the recess 180 in the breech plug 32 to the annular ring, it provides an open path for fluid between the two regardless of the orientation of passageway 208. The passageway 208 opens at an uncontrolled angular location with respect to the inlet fixture 42 (inner side). Fluid flows from one side of the inwardly curved portion of the hour glass shaped spacer 206 that communicates with the outlet of fitting 42 to the other side of the inwardly curved portion and from there to the passageway 208.

When the cartridge and plug assembly 26 are inserted into the pressure vessel 24 as shown in FIG. 2, the knob 34 is rotated and the external threads 188 of the breech plug 32 which form an eight thread per inch connector engage internal threads 200 in the pressure vessel 24, screwing the breech plug 32 and attached cartridge and plug assembly 26 down into the pressure vessel 24. When conical recess 210 in the bottom cap 144 reaches the external conical tip 212 of fitting adapter 214, the cartridge and plug assembly 26 is prevented from moving further down.

Screwing the breech plug 32 in further after the cartridge and plug assembly 26 has bottomed causes the upper flat annular surface of fitting nipple 176 to bear upon the flat lower surface of a hat-shaped washer 216. At this time, the hat-shaped washer 216 is residing against the upper surface of the head of a shoulder screw 218 which is threaded into cylindrical hole 222 in breech plug 32.

Further screwing of the breech plug 32 into the pressure vessel 24 causes the nipple 176 to lift the washer 216 off of the screw head and compress a coil spring 201 between annular surface 205 and the ridge of the washer 216. Continued screwing of the breech plug 32 into the pressure vessel 24 causes annular flange 190 of breech plug 32 to bear upon the upper surface of the pressure vessel 24. This provides a limit stop with the coil spring 201 compressed, as shown in FIG. 2.

The force of the compression spring 201 is enough to provide a low pressure seal between the hat-shaped washer 216 and the upper annular surface 203 of the fitting nipple 176. More importantly, this force also provides a low pressure seal on the mating conical surfaces of the recess 210 of lower cap 144 and the external conical tip 212 of the fitting adapter 214.

The sealing surface 186 acts as a pilot during the initial part of insertion to insure that the internal threads 188 do not get cross-threaded. A taper 189 at the end of the cylindrical sealing surface 186 pilots the breech plug 32 past seals 202 and 204 so that they are not damaged during insertion of the breech plug 32.

The locations of recess 224, passageway 208, high pressure seal 202 and the engaging threads 188 and 200 are chosen such that if the breech plug 32 is inadvertently removed when the interior of the pressure vessel 24 is pressurized, fluid within the pressure vessel 24 leaks past high pressure seal 202 and runs up the flights of the engaging screw threads 188 and 200, and depressurizes the system while there is still adequate screw engagement to ensure safety at the maximum rated operating pressure. The maximum rated operating pressure of the embodiment shown in FIG. 2 is 10,000 psi. The maximum operating temperature is 150 degrees Centigrade. The equipment need not be designed for operating temperatures above 300 degrees Centigrade and pressure above 30,000 pounds per square inch.

After the breech plug 32 and the cartridge and plug assembly 26 are assembled into the pressure vessel 24 as described above, but before an extraction, the space between the cartridge and plug assembly 26 and the pressure vessel 24 is purged of contaminants. During such a purge or cleaning cycle supercritical fluid enters fluid inlet 42, is distributed by the annular spacer 206 and goes through passageway 208. It passes between the outer diameter of hat-shaped washer 216 and the inside cylindrical diameter 230 of the recess within breech plug 32. Fluid then continues down and passes the annular space between the outside diameter of engaging nipple 176 and inside diameter 230 of the recess 180 in breech plug 32. The fluid passes garter spring 184 and circulates with even circumferential distribution around the outside of top cap 148, the extraction tube 152, and the bottom cap 144. The flow is collected in the annular space below the bottom cap 144 and above the bottom 240 of pressure vessel 24 and exits through vent discharge fitting 44, carrying contaminants with it.

Contaminated fluid between the exterior of extraction cartridge 26 and the interior of high pressure vessel 24 does not make its way into the interior of the extraction vessel. Low pressure seal 204 prevents contaminated fluid from reaching passageway 208. A labyrinth seal consisting of the narrow gaps between the major diameter of fitting nipple 176 and the inside diameter 230 of recess 180, and between inside diameter 230 and the outside diameter of the hat-shaped washer 216, prevents contaminants from reaching the space above the hat-shaped washer 216 by diffusion.

During a purge or cleaning cycle, there is downward flow of supercritical fluid through these gaps, and since the gaps are small, this downward fluid flow prevents eddies of contaminated fluid from passing up through the gaps. These gaps are only a few thousandths of an inch. Because the top of nipple 176 and the conical recess 210 at the bottom of the extraction cartridge are sealed by spring pressure, contamination cannot enter in these ways.

For extraction, supercritical fluid entering fitting 42 is distributed in the space occupied by spacer ring 206, flows through passageway 208 and flows down the few thousandths of an inch radial gap between the shoulder of shoulder screw 218 and the inside diameter of washer 216. The fluid continues to flow down and flows through passageway 250, porous frit 162 and into extraction volume 254 where it passes through material to be extracted. Extraction volume 254 is shown sized in FIG. 2 for a 10 cubic centimeter volume to receive sample. After passing the extraction volume fluid, it is exhausted for sample collection through frit 160, passageway 260, fitting adapter 214 and out through fitting 46.

All tubing, except tubing designated as capillary tubing, in this disclosure is 300 series stainless steel with an outside diameter of $\frac{1}{16}$ inch and inside diameter 0.02 inch.

In operation after assembly, the fluid flow associated directly with the pure fluid valve 54 (FIG. 1) exiting its port 114 (FIG. 1) flows through tube 58 through the heat exchanger 40, which is formed by coiling a contiguous segment of tubing into a helix, through the check valve 60A and through the tube 60B to the inlet fitting 42 of pressure vessel 24. The heat exchanger 40 actually resides in a longitudinal bore through heating block 22 so that the heat exchanger is at the same temperature as pressure vessel 24 and extraction tube 30. This preheats any fluid flowing into inlet fitting 42 to essentially the same temperature as the extraction cartridge assembly 30. This temperature is above the critical temperature for the fluid. Assuming that the pump 12 is set to produce a constant fluid pressure greater than the critical pressure, fluid entering the pressure vessel 24 will be a supercritical fluid.

The check valve 60A prevents backflow of supercritical fluid out of the pressure vessel 24 and extraction cartridge 26 of a first channel of a dual channel supercritical extraction system if there is a momentary drop in pressure of the supercritical fluid at the location of the tee 20. Such a pressure fluctuation could occur if the second channel of a dual channel extraction system is suddenly purged while the first channel is extracting. Each channel requires such a check valve.

During a purge cycle, contaminated supercritical fluid leaves fitting 44, flows through a tube 62 and enters the inlet fitting 116 of the purge fluid valve 52. Then it exits the outlet fitting 118 and passes through the tube 64 to the coupling 90 (FIG. 1). The coupling 90 couples the quartz capillary tube 110 so that contaminated purge gas exits through it. The bore of the capillary tube is small enough, such as 75 micrometers, and its length long enough, on the order of a few inches, to provide enough fluid resistance to limit the flow to a convenient rate: for example 5 milliliters per minute with respect to displacement of pump 12, at a pressure of 3,000 psi. Pump 12 is a constant pressure pump so this fluid flow does not affect the pressure within pressure vessel 24 once the flow stabilizes.

The outer end of capillary 110 may be immersed a purge fluid collector 92 (FIG. 1) containing an appropriate solvent 100 such as isopropyl alcohol to serve as a collector. Bubbles through this solvent indicate proper flow and the solvent tends to prevent the end of the capillary tube 110 from being plugged by the exhausted contaminants. A solvent is chosen in a manner known in the art to dissolve contaminants so the end of the capillary tube 110 does not plug and so the solvent may later be analyzed if desired to determine whether there was any contaminants on the exterior of the extraction cartridge.

During an extraction cycle, extractant exits fitting 46 on pressure vessel 24 and passes through tube 66. This tubing extends to inlet fitting 120 of extractant valve 50 which has rotary control shaft 126 attached to control knob 132. When the extractant valve 50 is opened by turning it counterclockwise from its closed position, fluid exits from its fitting 122, through tube 68 to fitting 94. Fitting 94 couples to quartz capillary tube 128 or other flow restrictor device.

Capillary tube 128 has a small enough bore, such as 50 micrometers, and a long enough length, on the order of several inches, to produce a flow rate, relative to the displacement of constant pressure pump 12, of a convenient amount. For example, this may be two milliliters per minute. The end of the capillary tube 128 dips into solvent 104 in the extractant collector 98.

Isopropyl alcohol is under some circumstances used for solvent 104. This solvent 104 must be a good solvent for the extractant since it must trap the extractant by dissolving it from the gas bubbling through it and must prevent plugging at the end of the capillary tube 128.

The solvent 104 is removed after extraction and is analyzed to determine the composition and amount of the extractant. Because of the pressure and temperature drop along the length of capillary 128 (and also capillary 110) fluid entering the capillary as a supercritical fluid (or a liquid if fitting 90 or fitting 94 is not heated) changes to a gas by the time it reaches the far end where it dips into the solvent which is at room temperature.

Before using the extraction system 10, the pump 12 is set to the desired pressure and the heater block 22 is set to the desired temperature. The bottom cap 144 (FIG. 2) with the frit 160 is screwed onto the bottom of extraction tube 152. The internal cavity 158 is then filled or partly filled with sample to be extracted. The frit 162 and top cap 174 are then screwed on to the top of extraction tube 152 forming the cartridge and plug assembly 26. The cartridge and plug assembly 26 is then clipped into breech plug 32 by shoving the fitting nipple 176 on the extraction cartridge past garter spring 184 located within breech plug 32. Knob 70 is set to the vent position closing valve 54 and opening valve 52 (FIG. 1). Valve 124 is set to the clockwise closed position.

The assembled breech plug and extraction cartridge are inserted into preheated pressure vessel 22 and manually screwed with knob 34 into pressure vessel 24 until annular flange 190 contacts the top of pressure vessel 24 (FIG. 2). The pressure vessel has been preheated under control of a thermocouple temperature controller to the desired temperature. The cartridge and plug assembly 26 within pressure vessel 24 rapidly rises to the required temperature.

After insertion of the cartridge and plug assembly 26 into the sample block 24, valve knob 70 is rotated to the purge position. In this position, both valves 54 and 52 are open. Since the pump 12 has already been set to the desired fluid pressure, fluid flows through tubes 76, 56, valve 54, tube 58, heat exchanger 40, tube 60, check valves 60A and 60B and inlet fitting 42 into the cavity 180. Since valve 124 is closed, supercritical fluid preheated to the correct temperature by heat exchanger 40, flows past hat-shaped washer 216, fitting nipple 176 and around the outside of cartridge and plug assembly 26. This supercritical fluid dissolves any contaminants on the outside of extraction cartridge assembly 30 and any contaminants inside pressure vessel 24. The hot supercritical fluid also ensures that the extraction cartridge assembly 30 is at the proper operating temperature. The supercritical fluid flushes the contaminants from fitting 44, through tube 62, valve 52, tube 64, the fitting 90 and the capillary tube 110.

After a short purge cycle, control knob 70 is set to the extract position. This sets valves 54 and 52 so that valve 54 is open and valve 52 is closed. Immediately after making this setting, the operator opens valve 124 by rotating knob 132 counterclockwise in the extract direction. Pressurized fluid flows through valve 54 into heat exchanger 40 so that it is at the desired supercritical temperature, and flows into fitting 42. It then flows into cavity 180 and past the annular space between shoulder screw 218 and the inside diameter of hat-shaped washer 216, after which it passes through the interior of fitting nipple 176, through passageway 250 and into the extraction vessel 26. This supercritical fluid flowing through the interior sample cavity 254 of the extraction cartridge extracts analyte from the sample 134 contained within the cavity 254.

Supercritical fluid with the analyte in solution passes out through the fitting 46, the tube 66, the valve 124, the tube 68, the coupling 94 and the capillary tube 128 which leads into the collecting solvent 104 within test tube 98. The analyte is dissolved in the solvent 104 for later analysis. When the extraction is complete, knob 132 is rotated clockwise in the closed direction, closing valve 124. This stops the flow of supercritical fluid into the extraction cartridge 26. Knob 70 is then rotated clockwise to the vent position. This closes valve 54 and opens valve 52, depressurizing the pressure vessel 24 and cartridge and plug assembly 26 through capillary tube 110.

When bubbles stop issuing through the end of capillary tube 110, depressurization is complete. Knob 34 is rotated counterclockwise to unscrew the breech plug 32 and the attached cartridge and plug assembly 26 from pressure vessel 24. Extraction cartridge assembly 30 may now be open to empty spent sample.

Figure 3:
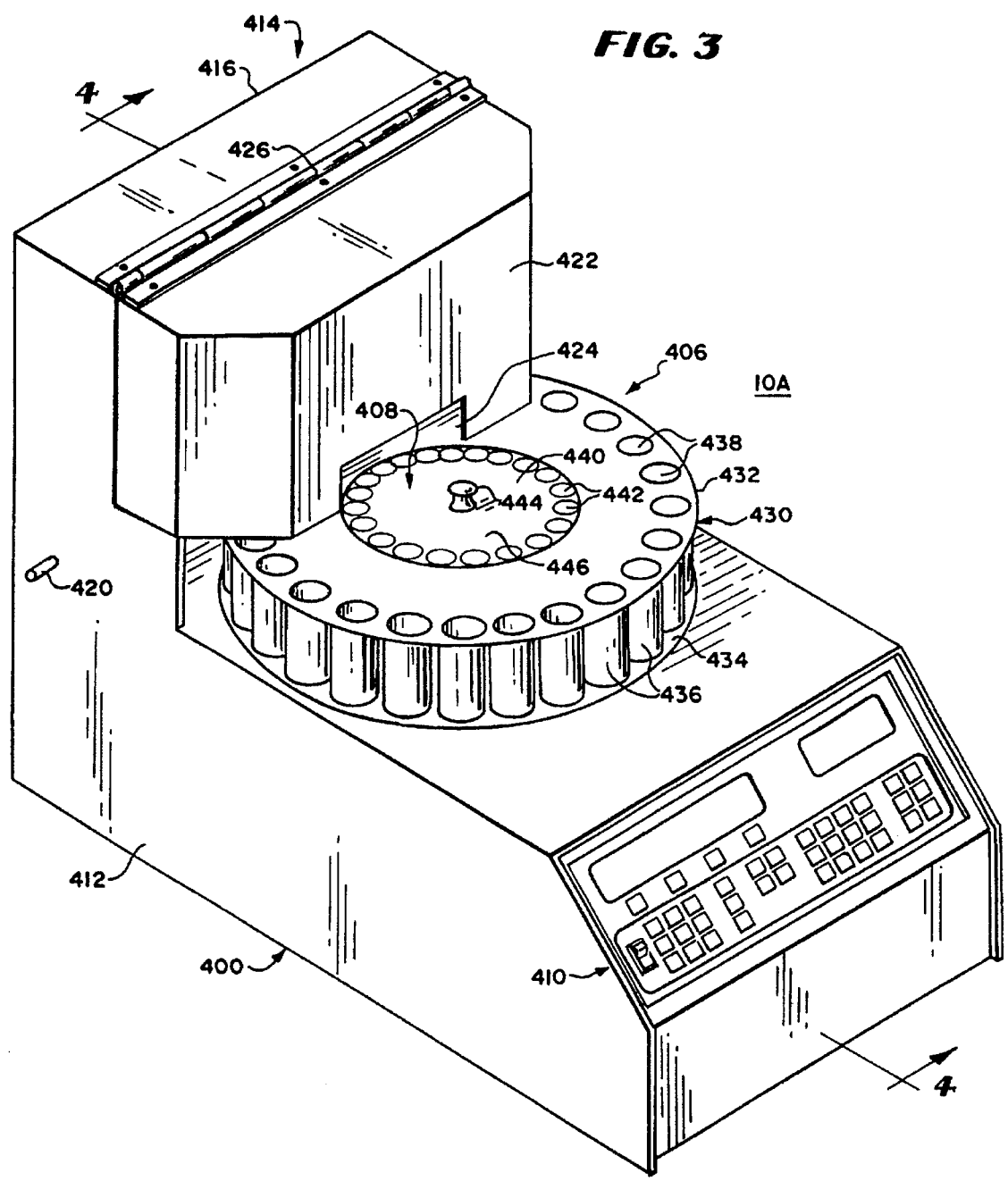
FIG. 3 is a perspective view of another embodiment of the invention capable of automatic extraction of a series of samples.

In FIG. 3, there is shown a simplified perspective view of another embodiment 10A of supercritical fluid extraction system having a cabinet 400 containing a drive section in its lower portion (not shown in FIG. 3), an extraction section in the upper portion of the cabinet (not shown in FIG. 3), a sample injection section 406 and a fraction collection section 408. The supercritical liquid extraction system 10A is controlled from a panel 410 on the front of the cabinet 400 and the drive section operates the extraction section, the sample injection section 406, and the fraction collection section 408, which cooperate together to extract a plurality of samples sequentially and collect the extractant from the samples in separate containers with minimum intervention by an operator.

The liquid extraction system in the embodiment 10A operates in a manner similar to that of the embodiment of FIG. 1 but is adapted to cooperate with the novel sample injector and fraction collector. With this arrangement, a series of samples to be extracted are preloaded into a means for holding the samples and the samples are automatically injected one at a time into the extractor. In the extractor, supercritical fluid is supplied to the samples and an extractant is removed from the samples one by one. To aid in correlating the embodiment 10 and the embodiment 10A, similar parts have the same reference numerals but in the embodiment of FIG. 10A, the numerals include the suffix "A".

The extractant is supplied to individual containers or individual compartments of one container in a fraction collector. Thus, a plurality of extractions are performed on a plurality of different preloaded samples without the need for manually loading samples or initiating the flow of the supercritical fluid for each individual sample. The samples are automatically mechanically moved one by one into the extractor for extraction instead of being individually physically injected by an operator.

The cabinet 400 has a lower portion 412 generally shaped as a right regular parallelopiped with an angled control panel 410 and upstanding upper portion 414 which is another right regular parallelopiped extending upwardly to create a profile substantially shaped as an "L" having a common back portion or rear panel 416 which may contain fans and connections for supplementary pumps and the like. A fluid fitting 420 extends from one side to permit near supercritical fluids to be introduced into the cabinet 400. The L-profiled cabinet 400 has an angled front panel 410 for convenient use of controls and a top surface on the foot of the "L" for manipulation of samples to be injected and extractants that are collected.

To permit access to the interior of the cabinet 400, the upper portion 414 includes a hinged front access panel 422 having hinges 426 at its top so that it can be pivoted upwardly. It includes an opening 424 near its bottom to permit the entrance of fraction collector receptacles that are relatively tall. It extends downwardly to a point spaced from the top surface of the lower portion 412 of the cabinet 400 a sufficient distance to permit the entrance of normal receptacles used in the sample injector and the fraction collector.

The sample injection section 406 includes a sample reel 430 which is formed of upper and lower rotatable plates 432 and 434 spaced vertically from each other and containing holes in the upper plate 432 and openings in the lower plate 434 which receive cylindrical tubular sleeves 436 having vertical longitudinal axes and open ends. The upper open end 438 permits samples to be received and to be removed as the sample reel 430 is rotated into the extractor.

With this arrangement, the sample reel 430 may be rotated to move samples one by one into the extractor for processing. The sample reel 430 is horizontal and extends into the upper portion 414 of the cabinet 400 and into the extractor assembly with its vertical center of rotation being outside of the upper portion 414 to permit ready access to a number of the sleeves 436 by users and yet to permit sequential rotation by automatic means into the extractor. In the preferred embodiment, there are 24 sleeves for containing 24 distinctly different samples which can, without human intervention, be moved into the extractor.

To receive extractant, the fraction collection section 408 includes a horizontal fraction collector reel 440 mounted concentrically with the sample reel 430 but having a smaller diameter to be inside the sample reel 430 having a plurality of openings 442 circularly arranged in spaced apart relationship with each other about the periphery of a top plate 446 of the fraction collector reel 440 and having in its center a knob 444 by which the fraction collector reel 440 may be lifted and removed from the cabinet 400. With this arrangement, the fraction collector reel 440 may be lifted and removed or reinserted after the hinged access panel 422 is pivoted upwardly about the hinges 426.

When the fraction collector reel 440 is in place, it is rotated automatically through the opening 424 into a location in which one or more individual containers 442 may receive extractant. The fraction collector reel 440 is moved alternately with the sample reel 430 and independently of it so that, after a sample injection and extraction, one or more of the openings 442 are moved into position to receive the extractant prior to the injection of another sample for extraction.

Because the reels 430 and 440 rotate within the upper portion 414 of the cabinet 400 with a portion of its periphery outside of the cabinet 400, the collected extractant may be removed and new sample added during operation of the equipment. For this purpose, the receptacles for the fractions and the receptacles for the samples have upward open ends and are mounted with their axes vertical.

Figure 4:
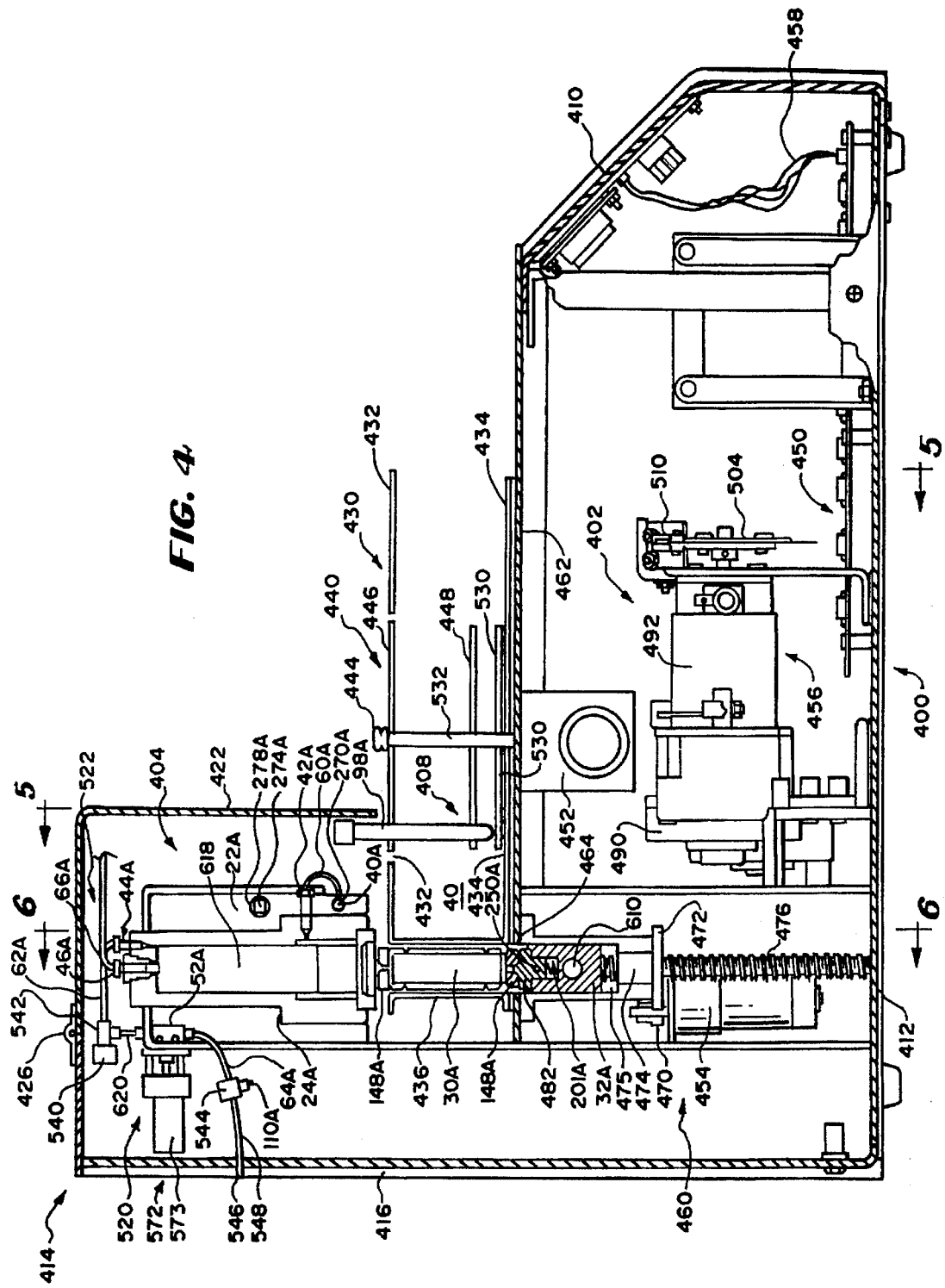
FIG. 4 is a sectional view taken through lines 4—4 of FIG. 3.

In FIG. 4, there is shown a longitudinal sectional view through lines 4—4 of FIG. 3 showing the cabinet 400, the drive section 402 within the cabinet 400, the extraction section 404, the sample injection section 406 and the fraction collection section 408. The drive section 402 includes a control system 450, a sample-and-extractant container reel drive assembly 452, a sample injector drive 454 and a fluid drive or pump 456. The control system 450 receives information from the control panel 410 and conveys information to it through a cable 458. It also controls the pump 456, the sample-and-extractant container reel drive assembly 452 and the sample injector drive 454, which cooperate together to move samples into position, inject them into the extractor, pump fluids through the extractor to extract the samples and collect the samples in sequence one by one.

To inject samples into the extraction section 404, the sample injection section 406 includes the sample-and-extractant container reel drive assembly 452, the sample reel assembly 430, and a cartridge injector assembly 460. The sample-and-extractant container reel drive assembly 452 drives the sample reel assembly 430 to carry a cartridge assembly 30A onto the cartridge injector assembly 460 which lifts it under the control of the sample injector drive 454 upwardly into a pressure vessel 24A for the purpose of extracting a sample within the cartridge assembly 30A. The cartridge assembly 30A and the pressure vessel 24A are similar to the cartridge assembly 30 and pressure vessel 24 of the embodiment of FIGS. 1–14 and are only adapted such as by having their top and bottom sides reversed to permit the cartridge assembly 30A to be inserted from the bottom into the pressure vessel 24A and be more easily sealed therein for extraction and removed by gravity after extraction.

To drive the sample reel assembly 430, the sample-and-extractant container reel drive assembly 452 includes a central transmission and motors on each side that drive the transmission under the control of the control system 450 to drive either one or both the sample injector reel assembly 430 and the fraction collector reel 440.

The sample injector reel assembly 430 includes the top plate 432, the bottom plate 434, both of which are rotatable together to carry a plurality of sleeves 436 sequentially, one at a time, into position for the repeated injecting of cartridges one by one into the pressure vessel 24A and the removal of the cartridges from the pressure vessel 24A and the return of them to the reel assembly 430 one by one so that only one cartridge is in the pressure vessel 24A at a time.

Within the extraction section 404, a stationary bottom plate 462 has a hole 464, with the hole being aligned with the open-bottom end of the pressure vessel 24A and the upper end of the cartridge injector assembly 460. Consequently, the cartridge assemblies such as 30A are rotated one by one above the open end 464 in the bottom plate 462 for movement upwardly into the pressure vessel assembly 24A by the cartridge injector assembly 460 under the control of the sample injector drive 454 for extraction of the sample therein. With this arrangement, a stationary plate 462 holds the cartridge assemblies 30A in place as they are rotated by the upper and lower plates 432 and 434 until they are sequentially brought over the opening 464 through the stationary plate 462 for elevation into the pressure vessel 24A.

To inject cartridges into the pressure vessel 24A, the cartridge injector assembly 460 includes the sample injector drive 454, a pinion 470, a gear 472, a multi-threaded, fast action nut 474, a corresponding screw 476, and piston or plug 32A. The pinion 470 is mounted to the output shaft of the drive gear motor 454 and engages the teeth of gear 472. The gear 472 is fastened to or integrally formed with the drive nut 474 which, as it rotates, moves the screw 476 upwardly or downwardly. The support platform 475, piston or plug 32A and sample container 30A are carried by the top of the screw 476 and are moved upwardly and downwardly. The top surface of the plug 32A, which is supported by the screw 476 in its lower position is flush with the bottom of the opening 464 in the fixed plate 462 to support a cartridge such as 30A therein and in its top position positions the piston or plug 32A at the bottom of the pressure vessel 24A. Plug 32A carries self-actuated, spring-biased, cylinder seals, such as those made by the Bal-Seal Corporation. These seals provide a high pressure fluid-tight seal between the plug 32A and the inner wall of the pressure vessel 24A.

With this arrangement, the piston or plug 32A is sealable against the walls of the pressure vessel 24A during the extraction process after moving the cartridge assembly 30A upwardly into the pressure vessel 24A, and after extraction, can move the cartridge assembly 30A downwardly back to the sample reel assembly 430 for rotation out of the upper injector housing 414 as a new cartridge is moved into position for injecting into the pressure vessel 24A. A bearing mount rotatably supports the nut 474 while maintaining it in the same vertical position so as to move the rapid-advance screw or other screw 476 upwardly and downwardly.

The plug 32A serves a function similar to the breech plug 32 in the embodiment of FIGS. 1–14 and contains within it an opening supporting a spring 201A and a support block 482 so that the support block 482 is biased inwardly against the cartridge end 148A to move the cartridge 30A into place against fittings for supercritical fluid.

To extract the sample in the cartridge 30A after it has been moved into position and the breech plug 32A fastened in place for a seal, extracting fluid is applied through the fitting 42A in a manner similar to the embodiment of FIG. 1, so that the extracting fluid flows through one path into the cartridge 30A and through another path over the outside of the cartridge 30A into the fitting 44A and from there to a purge collector or vent. The extractant, after passing through the cartridge and the sample, exits from a fitting 46A and proceeds to the sample collector in a manner to be described hereinafter.

To pump fluid such as carbon dioxide into the pressure vessel 24A at a temperature proper for supercritical extraction: (1) the pump 456 includes a pump head and gear box 490 and an electrical motor 492; and (2) the pressure vessel 24A has an aluminum heating block 22A over it, an opening 278A in the aluminum heating block, a rod-shaped heating element 274A in the aperture 278A, the extracting fluid fitting 42A and a heat exchanger 40A entering the aluminum heating block 22A at aperture 270A. The motor 492 drives the pump mechanism 490 to pump fluid into the aperture 270A, through the heat exchanger 40A within the aperture 270A, through the connecting tubing 60A and the fitting 42A and into the cartridge 30A and the pressure vessel 24A. The aluminum block 22A controls the temperature of the fluid, which may be carbon dioxide or any other useful extracting fluid to keep it above the supercritical temperature for that fluid, and for that purpose, the heating rod 274A within the aperture 278A is used when necessary to heat the aluminum block 22A.

The pump 456 may be any suitable pump, but one appropriate pump for carbon dioxide is a highly modified version of the pump used in the Isco model 2350 HPLC Pumping System sold by Isco, Inc., Lincoln, Nebr. However, for best results when using carbon dioxide, the stroke of this pump is modified from ten millimeters to fifteen millimeters and smaller, lower trapped-volume check valves are used. These modifications increase the compression ratio of the pump from 1.64:1 to 2.64:1 and increase the displacement by a multiple of 1.5. Additional changes are the use of: (1) Carpenter Technologies 182FM stainless steel in the pump head, instead of type 316, for better thermal conducting; (2) differently shaped cam; and (3) heavier bearings.

To collect extractants, the fraction collector section 408 includes the fraction collection reel 440, the sample-and-extractant container reel drive assembly 452, a purge fluid outlet system 520 and an extractant fluid outlet system 522. The fraction collection reel 440 moves receptacles such as 98A into position within the housing 414 where the extractant fluid outlet system, 522 to be described in greater detail hereinafter, causes fluid from the fitting 46A in the pressure vessel 24A to flow outwardly and into the receptacle 98A after piercing a seal therein. The purge fluid system 520 causes purge fluid to flow from the purge fluid fitting 44A to a pressure control unit and finally to an exhaust or collection unit.

To move the collection receptacles 98A into position, the fraction collection reel 440 includes a knob 444, an intermediate plate 448, an upper plate 446, a lower disk plate 530 and a drive rod 532. The drive rod 532 rotates within the fixed disk 530 and carries above them the upper and lower plates 446 and 448. The upper and lower plates 446 and 448 have aligned circumferentially spaced holes through them, each of which can receive a collection vial such as 98A. The lower disk 530 does not have holes and supports the plates as they are moved. The knob 444 may be used to lift the fraction collector reel 440 from the center of the sample injector reel 430 after the hinged front access panel 422 has been opened about its hinge 426.

The sample-and-extractant container reel drive assembly 452 moves the collection vials one by one inside the upper portion of the housing 414 to receive extractant. One or more such vessels 98A may be moved in place each time a sample cartridge 30A is extracted so that the receptacles 98A are moved alternatively with the sample cartridges 30A, although several receptacles 98A may be moved in the time between moving one of the sample cartridges 30A into a pressure vessel 24A and the time the sample cartridge is removed from the pressure vessel 24A.

In operation, the extractant passes through fitting 46A and into the fraction collector receptacles 98A in a manner to be described hereinafter. The purge fitting 44A communicates with the extraction volume in the cartridge 30A and is connected to a Tee-joint tube 542 through tubing 62A. A second arm of the Tee-joint tube 542 is connected to an over-pressure safety diaphram 540 calibrated to burst at 15,000 pounds per square inch. This is an excess of the maximum rated working pressure of 10,000 pounds per square inch for pressure vessel 24A. The remaining arm of the Tee-joint tube 542 is connected to the purge valve 52A. The other side of the purge valve 52A is connected to the first side of a second Tee-joint tube 544 through the tube 64A. The second side of the Tee-joint tube 544 is connected to an exterior vent port 546 through a tube 548. The third arm of the Tee-joint tube 544 is connected to the exhaust tube 110A which vents the fraction collection vial 98A. With this arrangement, the purge fluid flowing through fitting 44A is removed and a tube connected to the vent port 546 is also used to vent the sample receptacle 98A in a manner to be described hereinafter.

Figure 5:
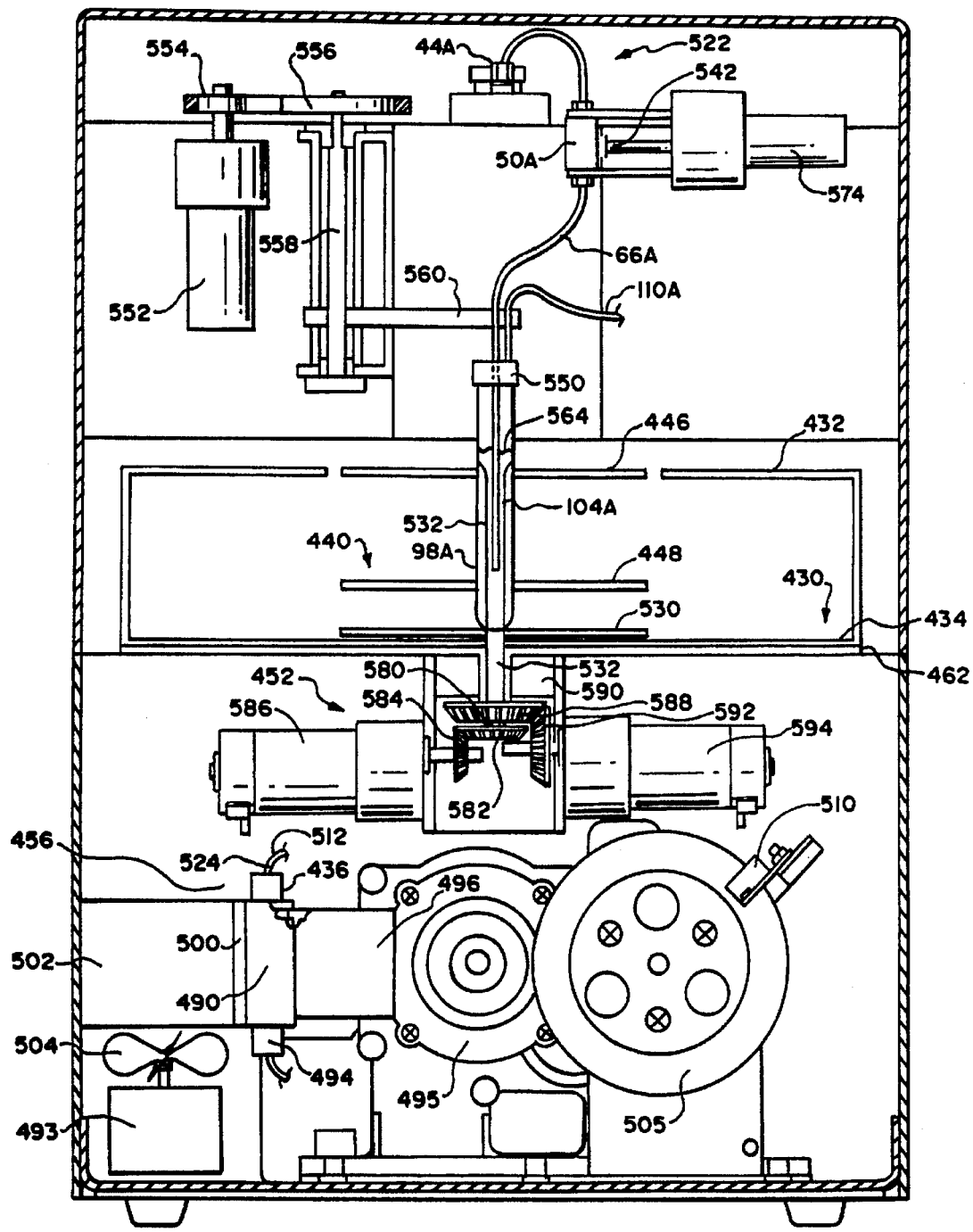
FIG. 5 is a sectional view taken through lines 5—5 of FIG. 4.

In FIG. 5, there is shown a simplified sectional elevational view of the embodiment 10A of supercritical fluid extractor taken through lines 5—5 of FIG. 4 having the sample-and-extractant container reel drive assembly 452, the pump 456 and the extractant fluid outlet system 522. The sample-and-extractant container reel drive assembly 452 may selectively move either the sample reel 430 or the fraction collection reel 440 under the control of the controller 450 (FIG. 4).

To selectively drive the fraction collection reel 440, the sample-and-extractant container reel drive assembly 452 includes a fraction collection spindle 532, a tubular shaft 580, a bevel gear 582, a bevel gear 584 and a gear motor 586. The controller 450 controls the gear motor 586 to rotate the fraction collection reel 440. For this purpose, the spindle 532 is held by the tubular shaft 580. The bevel gear 582 is fastened at the end of the spindle 532 and meshes with the bevel gear 584 on gear motor 586. The controller 450 causes the motor 586 to rotate its output shaft so as to drive the collection reel 440 (FIGS. 15 and 16) and not the sample injector reel 430 (FIGS. 3 and 4).

To move the sample injector reel 430, the sample-and-extractant container reel drive assembly 452 includes the tubular shaft 580 supported by bearing block 590, fraction collection spindle 532, bevel gear 588, bevel gear 592 and gear motor 594. The controller 450 actuates gear motor 594 to cause the bevel gear 592 to rotate. The bevel gear 592 meshes with the bevel gear 588 which is attached to the bottom end of the fraction collection spindle 532.

To cause extractant to flow into the fraction collection vial 98A, the extractant fluid outlet system 522 includes a gear motor 552, a pinion 554, a gear 556, a lead screw 558, an arm 560, and a restrictor tube 66A. The vials 98A have a seal 550 over the top, which seal can be pierced.

To cause the seal 550 to be pierced and extractant to flow into the vial 98A, the controller 450 starts the gear motor 552 which rotates its pinion 554 which is in engagement with the gear 556. The pinion 554 rotates the gear 556, which engages and is fastened to the rotating lead screw 558. The arm 560 is mounted for movement by the lead screw 558 and lowers it into a position where the restrictor tube 66A pierces the cap 550 on the collection vial 98A and moves its tip below the surface 564 of the collection fluid within the vial 98A. As the extractant flows into the tube, exhaust is removed from the tube through an exhaust tube 110A (FIG. 4 in addition to FIG. 5).

If either the tube 66A or the tube 110A are stiff or otherwise inconvenient to bend, it is advantageous to raise the collecting vial 98A up to tubes 66A and 110A, instead of lowering the tubes into the collecting vial. This alternate arrangement does not pose any difficulty as the collecting vial 98A may be raised by a support similar to plug 32A, which support is connected directly to plug 32A so that it moves synchronously with plug 32A.

With either arrangement, extractant flows through the fitting 46A (FIG. 4) from the sample cartridge 30A (FIG. 4) through the tubing 522 (FIG. 4), the valve 50A and the restrictor tube 66A. Extractant residing in bubbles from the tube are captured through trapping fluid 104A whereby extractant is trapped in the trapping fluid 104 in the vial 98A and extracting fluid passes out through the exhaust tube 110A, Tee-joint tube 544 (FIG. 4), tube 66A and exhaust port 546 (FIG. 4). After collection of the extractant, the motor 552 moves in the reverse direction and raises arm 560 which removes the restrictor tube 66A and exhaust tube 110A from the vial 98A.

Because the pump head 490 is heated by pumping at high compression, both the pump head 490 and incoming fluid line are preferably cooled. In the preferred embodiment, they are cooled thermoelectrically (Peltier effect). The pump head 490, the inlet check valve housing 494 are formed of Carpenter 182FM stainless steel rather than type 316 stainless steel to increase their thermal conductivity.

In pumping, the pump drive motor 492 (FIG. 4) drives a cam within cam housing 495 through appropriate gear train within the gear housing 496. The rotating cam within the cam housing 495 operates a pump plunger which cooperates with the pump head 490A (FIG. 5) to draw liquid carbon dioxide through inlet check valve assembly 494 and discharge it through outlet check valve assembly 436. In one embodiment, the Peltier cooling plate 500 is mounted to the flat face of the pump head 490A (FIG. 5) with cooling fins 502 mounted for good thermal contact to the opposite side of the Peltier cooling plate 500.

When an electric current is passed in the proper direction through the Peltier cooling plate 500, heat is withdrawn from the pump head 490A (FIG. 5) and rejected into the cooling fins 502. A fan 504 driven by an electric motor 493 (FIG. 5) withdraws heat from the fins 502. Another Peltier-effect cooled heat exchanger is also utilized in the inlet line.

To control the speed of the motor 492 (FIG. 4), a tachometer wheel 505 is mounted to the shaft of motor 492 (FIG. 4) with a photoelectric tachometer sensor 510 mounted to provide signals reading indicia on the wheel. The signals from the photoelectric tachometer 510 indicate the speed of motor 492 and thus the pumping speed of pump 456. These signals are compared in the controller 450 and utilized to control the speed of the motor 492.

To control the pressure on the outlet line 512 from the pump, a pressure transducer 514 (FIG. 6) generates a signal indicating the pressure. This signal is used as a feedback signal to control the pumping speed. This structure is provided by existing pumps such as the Isco model 260D pump.

Figure 6:
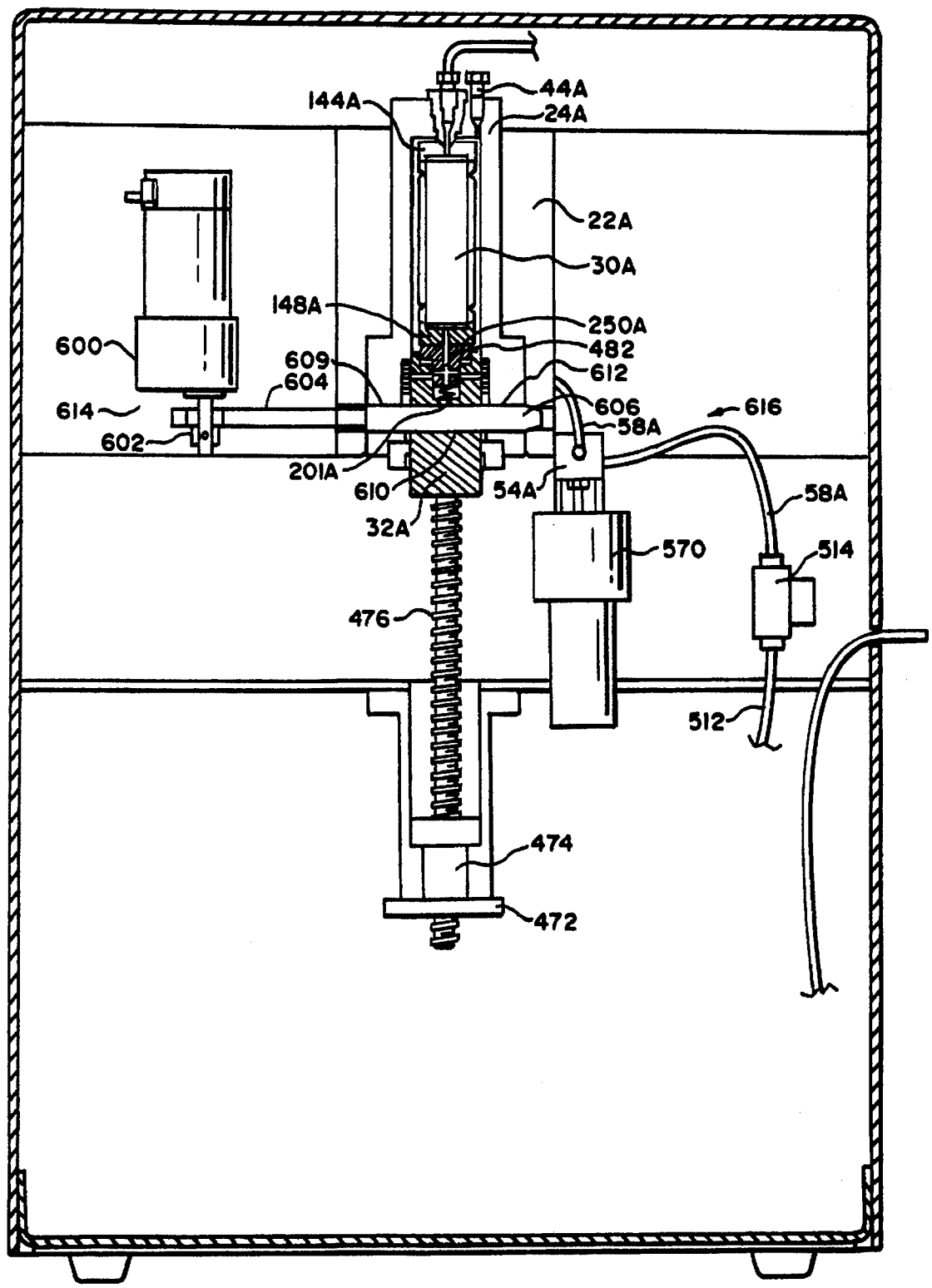
FIG. 6 is a sectional view taken through lines 6—6 of FIG. 5.

In FIG. 6, there is shown a sectional view, partly simplified, taken through lines 6—6 of FIG. 4 having a locking mechanism 614 for locking plug 32A into the pressure vessel 24A and a control mechanism 616 for controlling the extraction fluid. As best shown in this view, the locking mechanism 614 includes a gear motor 600, a pinion 602, a rack 604, a locking pin 606, a hole 609 in the pressure vessel 24A and a hole 610 in the piston or end piece or breach plug 32A and a hole 612 through the other side of the pressure vessel 24A. Instead of a pin 606, a yoke of the type conventionally used as a Winchester 94 rifle locking mechanism advantageously may be used. This type of locking mechanism is a yoke mounted to a pinion 602 and rack 604 as shown in FIG. 6. In this mechanism, a plate with a slot cut out of it to form a yoke is moved by the rack and pinion to pass under the plug 32A to hold it against pressure and provide strong support therewith by further engaging slots in the pressure vessel 24A. The aforementioned slot in the plate provides clearance for the screw 476.

In operation, the gear motor 600 is caused by the control system 450 (FIG. 4) to drive locking pin 606 through the opening 609 in the pressure vessel 24A, through the opening 610 in the piston 32A and through the opening 612 in the pressure vessel 24A by rotating the pinion 602 to drive the rack 604 that carries the locking pin 606, thus locking the cartridge 30A (FIG. 4) in place within the pressure vessel 24A.

To control the flow of extracting fluid from the pump 12 (FIG. 1) into the pressure vessel 24A and cartridge 30A, the control mechanism for extracting fluid includes the gear motor 570 and valve 54A that is connected at one end to the conduit 58A that extends from line 512 and pressure transducer 514 to the conduit 58 which passes into the heat exchanger 40 (FIG. 1). In operation, the gear motor 570 under the control of the control system 450 opens the valve 54A to permit the flow of extracting fluid into the cartridge 30A and pressure vessel 24A during an extraction operation. It also rotates in the opposite direction after extraction is complete to close the valve 54A.

Figure 7:
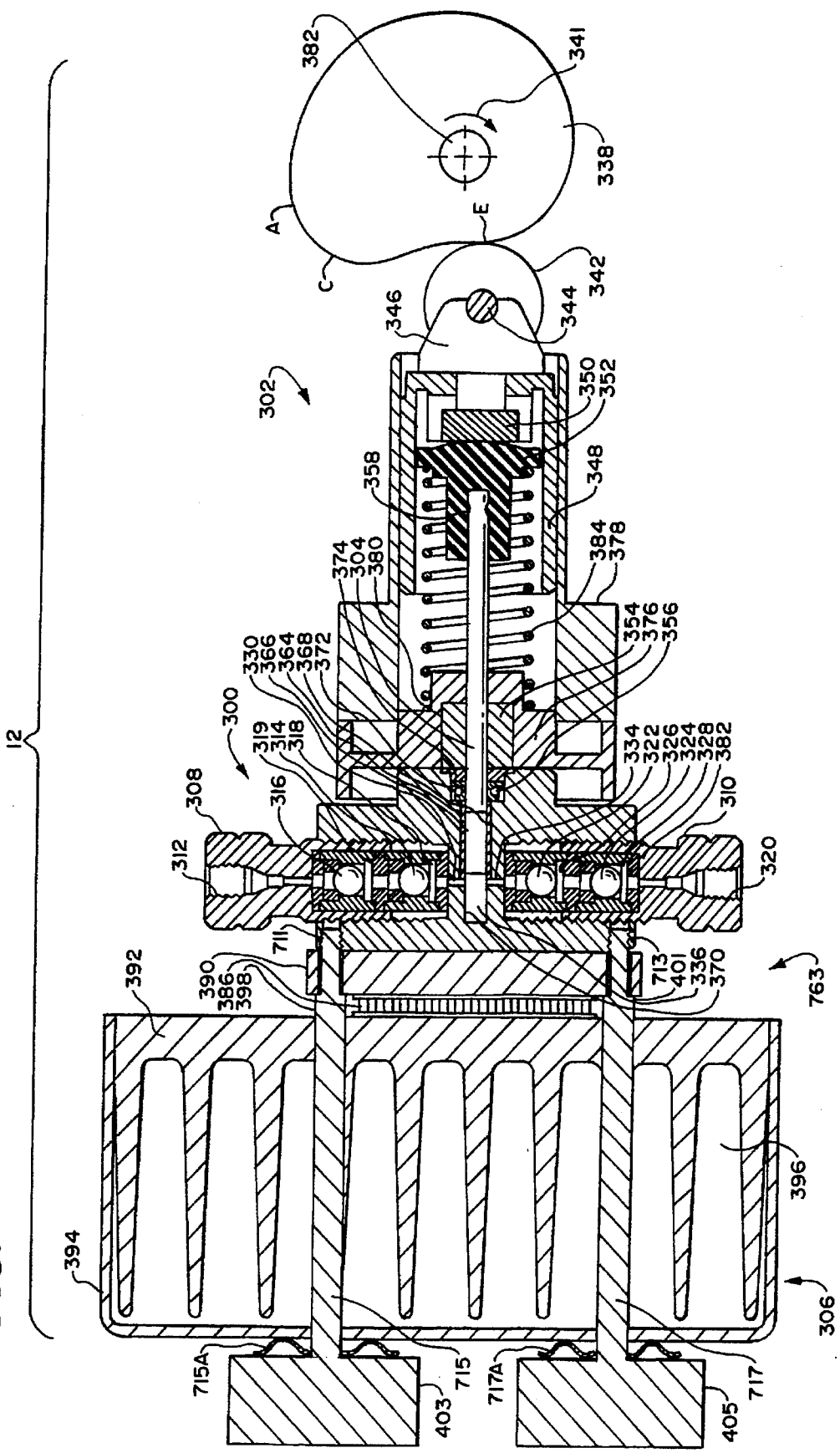
FIG. 7 is a cross-sectional, fragmentary view of the pumphead, its drive cam, thermoelectric cooling means.
Figure 10:
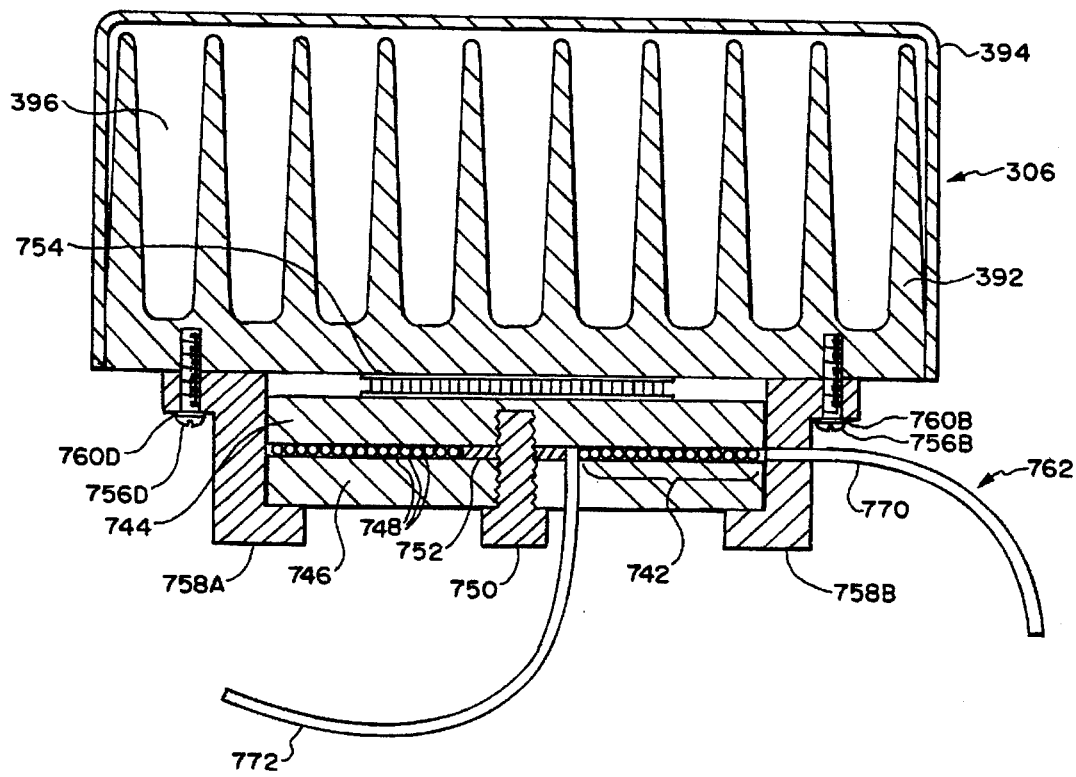
FIG. 10 is a sectional fragmentary view of the fluid inlet heat exchanger.
Figure 11:
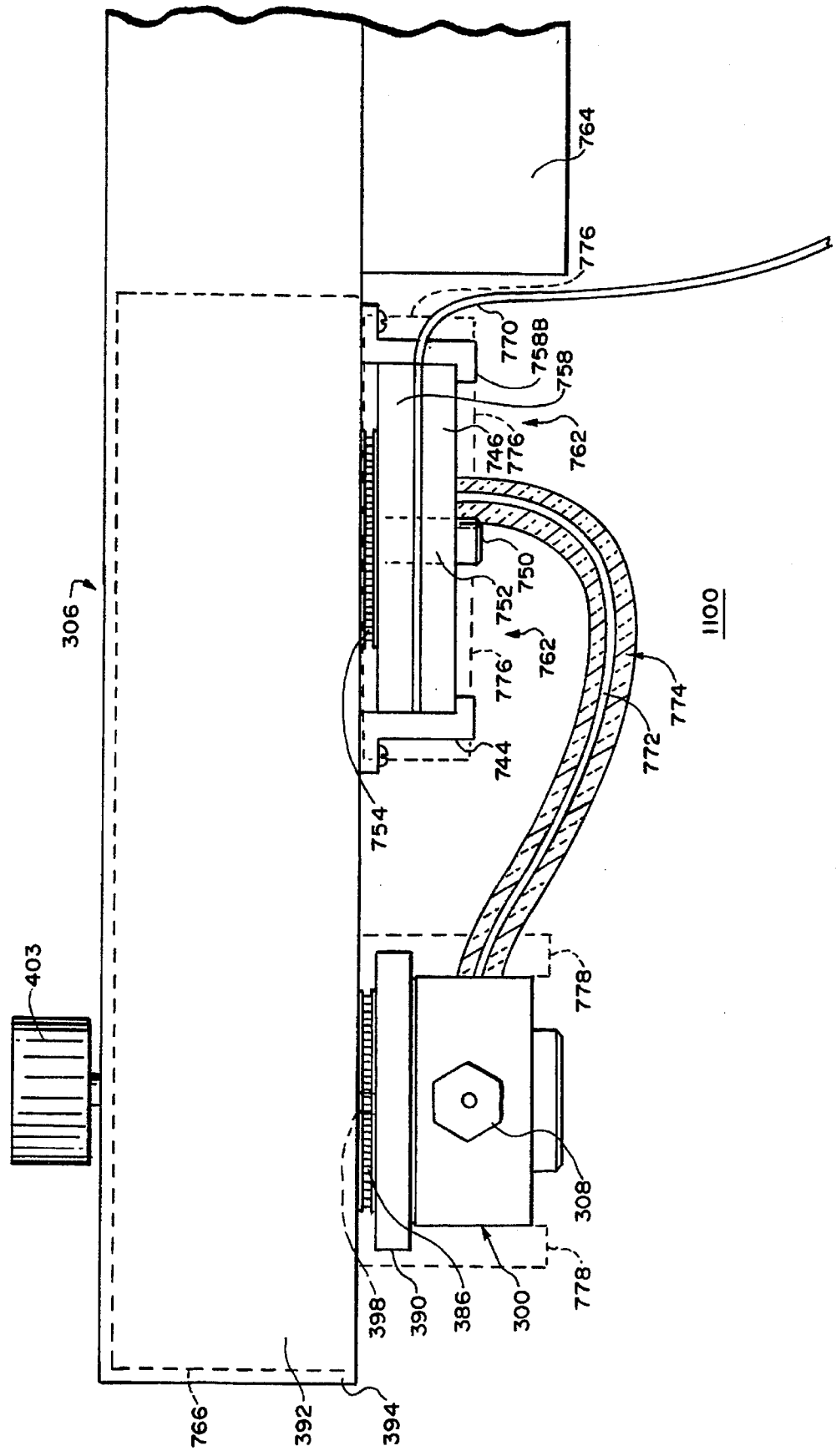
FIG. 11 is a fragmentary elevational view of the metal pumphead, the in-line heat exchanger assembled to thermoelectric cooling means and a fan which removes rejected heat from the thermoelectrical cooling means.

The sample cartridge 30A (FIG. 4) is composed of a tubular sleeve or body portion 140A (FIG. 4) and end pieces 144AA (FIG. 4) and 464A (FIG. 4). The end pieces 144A and 464A are made of stainless steel or an inert plastic and carry a stainless steel frit or filter disk centered in the interior of each. The flat, narrowed ends of the tubular sleeve 140A seal against PTFE washers around the frits which seal against the end pieces at the location between the diameters of the filter disks and the inside diameters of the end pieces 144A or 464A respectively. In FIG. 7, there is shown a cooled pumping unit having a cylindrical pumphead block 300, a piston drive assembly 302, a piston 304, a chamber 336, a cooling assembly 306, and a heat exchanger 763 for transferring heat from the pumphead block 300 to the cooling assembly 306, connected together to pump fluid while cooling the fluid and pump with air-thermoelectric cooling. The heat exchanger 762 (FIG. 10) for transferring heat from the fluid into the cooling assembly is not shown in FIG. 7 but is shown in FIGS. 10 and 11. Fluid volume is measured by pressure and movement of the piston 304 within the chamber 336. The cooling assembly 306 and the heat exchangers 762 and 763 (heat exchanger 762 not shown in FIG. 7) do not use liquid cooling but the pumping system is cooled entirely by air and not by a liquid coolant.

The cylindrical pumphead block 300 includes threaded recesses for receiving a generally cylindrical fluid outlet check valve 308 and fluid inlet valve 310. The fluid outlet check valve 308 incorporates: (1) a threaded recess 312 for a conventional fluid coupling fitting; (2) ball check valve elements 314 and 316; (3) valve seats 318 and 319; (4) the cylindrical passageway 330. The cylindrical passageway 330 communicates between the check valve element 314 and the pumping chamber 336 and contains fluid in contact with the fluid in the pumping chamber 336. The valve elements 314 and 316 cooperate with valve seats 318 and 319 respectively in a manner known in the art to form a conventional dual-ball check valve assembly that blocks the flow of liquid into the chamber 336 and permits flow from the chamber 336 to the pump outlet.

The fluid inlet valve 310 incorporates: (1) a threaded recess 320 for receiving a conventional fluid coupling fitting; (2) check valve ball elements 322 and 324; (3) valve seats 326 and 328; and (4) the cylindrical passageway 334. The check valve ball elements 322 and 324 cooperate with valve seats 326 and 328 in a manner known in the art to form a conventional dual-ball check valve assembly controlling the flow of liquid into the chamber 336 and blocking flow of fluid from the chamber 336. The cylindrical passageway 334 communicates between the check valve element 322 and the pumping chamber 336 and contains fluid in contact with the fluid in the pumping chamber 336.

To limit the trapped fluid volume in the pumphead, the diameter of the fluid passageways 330 and 334, the annular volume between the piston 336 and the bore 370, and the interval volume of the seal 356 are sufficiently small to restrict the trapped liquid to no more than 0.9 times the displacement and to restrict the compression ratio to no less than 2.1:1. In the preferred embodiment, the passage 334 is only one millimeter in diameter and the passage 330 is even somewhat smaller. A high compression ratio (ratio of volume before compression to volume after compression by the pump) is especially advantagous for pumping very compressible liquids such as liquid carbon dioxide because the high compression ratio tends to quickly discharge the compression-heated fluid before it heats the pump head 300 and also improves the volumetric efficiency which is otherwise degraded by compression of the fluid during the compression/delivery stroke. Volumetric efficiency is defined by the amount pumped per stroke divided by the displacement. Higher volumetric efficiency results in a higher maximum flow rate. Compression ratio is less important to HPLC pumps because of the lower compression ratio and have a reason for needing larger inlet fluid passageways. HPLC pumps must have larger inlet fluid passageways because of cavitation problems.

The check valve balls 314, 316, 322 and 324 are preferably spheres made of synthetic ruby and the valve seats 318, 319, 326 and 328 are made of synthetic sapphire. The pumphead block 300 is made of stainless steel, preferably Carpenter type 182FM stainless steel because of its relatively high thermal conductivity (for a stainless steel), its good corrosion resistance and ease of machineability. In those cases where the requirement of ease of machineability is low, half-hard nickle may be used because of the superior thermal conductivity of half-hard nickle.

To move the piston rod 304, the piston drive assembly 302 includes a drive cam 338, a roller cam follower 342, a ferrule-anvil combination 352 and 350, a compression spring 384, a yoke 346 and a tubular slide 348 as its principal parts. The ferrule is attached by injection-molding onto the right end of the synthetic sapphire displacement rod, or piston rod 304. The yoke 346 is an integral part of the tubular slide 348 which supports the anvil 350. A circumferential groove 358 ground into the piston rod 304 insures a firm mechanical coupling between ferrule 352 and rod 304. The ferrule 352 is made of the same material as the anvil 350. Alternatively, the anvil can be made of polished stainless steel. The former material is a low coefficient friction plastic having relatively high compressive strength and relatively low compressive modulus. It is injection molded to form the ferrule 352 and the anvil 350. The ferrule 352 is molded onto the rod 304.

The drive cam 338 drives the cam follower 342, which in turn drives the ferrule 352 downwardly against the pressure of the compression spring 384. The rod or plunger 304 moves with the ferrule 352 to reciprocate in the chamber 336 to pump fluid through the outlet valve 308. The roller cam follower 342 is mounted to rotate on a trunnion 344 mounted in the yoke 346 mounted to the anvil 350 for rotation therewith.

The reciprocating sapphire piston rod 304 is shown in its maximum retracted position in FIG. 7. Rotation of drive cam 338 in the direction indicated by the arrow 341 forces the roller cam follower 342 mounted on trunnion 344 to move the yoke 346 in a direction that expells fluid which in the preferred embodiment is toward the inlet and outlet shown to the left in FIG. 7.

To improve piston seal life, the surface of the ferrule 352 that is engaged by the anvil 350 during a piston stroke is a spherical surface having a radius large enough so that, in case of misalignment with respect to anvil 350, the line of contact and direction of force between the spherical surface and the anvil does not have a significantly large component perpendicular to the axis of the piston rod 304. With this arrangement, the piston 304 is not forced out of alignment during a piston stroke. This reduces wear in the tubular bearing 354 and the seal 356 and prevents the rod 304 from breaking.

To reduce wear on the bearing 354, anvil 350 and ferrule 352 are in hertzian contact with each other. With this arrangement, the amount of depression of the spherical surface of the ferrule 352 and the forces lateral to the radius of the spherical surface that is normal to the anvil 350 is related to the compressive modulus of the ferrule material, the diameter of the spherical surface and the normal force. The relatively high strength of the material used, General Electric bearing grade polyetherimide resin "Ultem 4001", of 21,200 psi compressive strength and relatively low compressive modulus of 450,000 psi, produces a hertzian force at maximum operating pressure of only half of the compressive yield strength of ferrule 352 and anvil 350.

Because most conventional materials for such uses, such as for example, hardened type 440C stainless steel, tend to stress-corrode and because of the high compressive modulus of that material, the hertzian contact forces in this embodiment are sufficient to make them unsatisfactory for the purpose. However, the much softer Ultem #4001 used in the preferred embodiment is paradoxically satisfactory.

Unlike most pumps used for other purposes, the inlet fluid is under pressure that forces it into the pump chamber 356. There is a narrow clearance between the piston 304 and the walls 370 of the pumping chamber so the piston does not quite touch the walls 370. Instead, the piston rod 304 fits within and is principally guided by a first bearing sleeve 364. The sleeve 364 is force-fit into cylindrical recess 366 formed within the pumphead 300 with a larger diameter than the diameter of the pump chamber 336 and joining the walls 370 of the pump chamber 336 at a shoulder. The inside diameter (walls 370) of the pump chamber 336 is slightly larger than the inside diameter 368 of sleeve 364 so piston 304 does not come in contact with the inside diameter of chamber 336.

The internal diameter 368 of first sleeve 364 is an almost-snug, slip fit with respect to piston 304. The diametrical clearance is only about 0.001 inch and therefore, the sleeve acts as a linear bearing which closely and accurately guides the reciprocating motion of piston 304. Helical-toroidal spring-loaded self acting seal 356 is located in the hole 372 bored in pumphead block 300. The spring in the spring-loaded seal 356 improves the reliability of the seal. The seal used is a Bal-Seal type #X41641. The seal is backed up by ring 374 made of unmodified polyetheretherketone.

The bearing sleeve 364 is preferably made of a material softer than that of stainless steel pumphead 300. It should have a suitable spectrum of chemical resistance, a low coefficient of friction against piston 304 and should be dimensionally stable. It is believed that the suitable bearing materials should have a yield strength between 5,000 to 20,000 psi and adequate deformability.

Suitable materials if the pump is not intended to be used to pump fluids containing acid in the presence of water are No. 1 babbitt (tin with 4.5% copper and 4.5% antimony), or an alloy of tin containing 10% gold for hardening and increased corrosion resistance. The latter alloy has a corrosion resistance which is about twice as good as that of No. 1 babbitt. No. 1 babbitt, in turn, has corrosion resistance superior to that of any of the other babbitts.

Neither of these materials have corrosion resistance as good as the stainless steel pumphead block 300. Soft-metal bearing materials which have at least as good a corrosion resistance as the other wetted metals within the pump are gold or pure palladium annealed to a yield strength on the order of 6,000 to 10,000 psi. The materials for the bearing sleeve 364 either do not have an extremely broad spectrum of corrosion resistance (the tin alloys) or they are expensive (the precious metals; however palladium is not excessively expensive). Accordingly, the specific material is selected as trade-off between cost, the use of a bearing sleeve of a soft metallic material and corrosion resistance depending on the intended use of the pump.

Metals generally have high thermal conductivities and it is desirable to efficiently remove the heat of compression of a compressible fluid being pumped at a temperature close to its supercritical temperature. If sufficient heat of compression is not removed; the fluid gets too warm, its density drops rapidly and its compressibility increases rapidly, making it difficult or impossible to produce a reasonable mass flow with the pump.

To permit adequate heat removal from the fluid with a preferred material for the piston and the sleeve, the metallic wall 370 is in contact with about half the maximum volume of fluid within the pumping chamber 336 and serves on its own for a significant amount of heat removal within the pump chamber. Therefore, it is possible to use a low thermal conductivity material for the bearing sleeve 364 with a moderate degradation of performance. Suggested non-metallic materials for this sleeve include DuPont "PFA" perfluorinated polyether plastic or ICI "PEEK" plastic. These materials swell a small but significant amount in liquid carbon dioxide at high pressure, so a sleeve made of one of these materials must be originally machined to a greater diametrical clearance than the 0.001 inch used for a metal sleeve.

The pumphead block 300 is nutted tightly onto type 303 stainless steel studs 715 and 717 (FIG. 12) through support block 376 and into 203EZ (Ryerson) stainless steel guide sleeve 378. Support block 376 is injection molded from ICI type 450CA30 PEEK (carbon fiber reinforced polyetheretherketone). The 303 stainless studs are not shown since they are out of the plane of the section shown in FIG. 7. They are indicated as 715 and 717 in FIG. 12. Their nuts are recessed into pumphead 300. The support block 376 has relatively low thermal conductivity and thermally insulates the pumphead block 300 from the support sleeve 378. A recess 380 within support block 376 loosely supports tubular bearing 354 in the diametrical direction. Bearing 354 is preferably made of a low friction, strong plastic such as ICI type 450CF30 grade of PEEK. The bottom of recess 380 is in light face-to-face contact with the right end of tubular bearing 354, which tightly compresses it against backup disk 374 when the type 303 stainless mounting bolts (FIG. 12) are tightened during assembly.

In operation, as the cam 338 rotates on shaft 382, the sapphire piston 304 is urged to the left until it reaches its maximum leftward excursion with its end fairly close to the left end of the pumping chamber 336. The cam 338 continues to rotate past the maximum and then compression spring 384 and pressure within the chamber 336 urge piston 304 to the right with needle-bearing roller cam follower 342 remaining in contact with the periphery of the cam 338.

This reciprocating motion of the piston rod 304 continues and provides a pumping action for fluid entering the inlet fitting at 320 and exiting the fitting at 312 in the manner usual with reciprocating fluid pumps. The diameter of the piston 304 is ⅛ inch and its longitudinal motion during one rotation of cam 338 is 15 millimeters. This results in a displacement of 0.12 milliliter per stroke of the plunger 304.

Because of the heat of compression of liquid carbon dioxide, there must be some arrangement for removal of heat, or the temperature of liquid in the pumphead 300 will correspond to a vapor pressure higher than the supply pressure feeding the inlet valve 310 of the pump. Under this circumstance, the pump neither fills nor delivers fluid. Some prior art arrangements overpressurize the $CO_2$ supply tank with helium to solve this problem. This has several disadvantages, such as: (1) the helium overpressure in the headspace above the liquid $CO_2$ decreases as the tank empties and the headspace volume increases; (2) the helium dissolves into the liquid $CO_2$, decreasing its density which decreases its quality as a supercritical fluid extraction solvent; and (3) $CO_2$ from tanks incorporating helium pressurized headspace is more expensive than that from tanks filled with $CO_2$ alone.

To permit carbon dioxide to be pumped without helium overpressure, the cooling assembly 306 and the heat exchanger 763 in the preferred embodiment incorporates thermoelectric cooling element 386 which removes heat from aluminum heat coupling spreader plate 390 which in turn is in close thermal contact with pumphead block 300. Melcor type CP1.0-127-05L thermoelectric elements and Melcor type CP1.4-127-045L thermoelectric elements provide satisfactory results, with Melcor type CP1.4-127-045L producing the better results of the two elements. The heat coupling spreader plate 390 is desirable since the thermoelectric element 386 is square and its corners would protrude past the outside diameter of pumphead block 300. The heat rejected from pumphead 300 and spreading plate 390 to the thermoelectric cooling element 386, plus the electric resistive heat generated within the cooling element 386 is connected to finned aluminum extrusion 392 which provides for heat removal. The heat removal extrusion 392 is surrounded sheet metal shroud 394 defining multiple cooling air passages such as 396 for forced air cooling to be described later. No liquid cooling is used in any form.

Stepped screws 398 and 401 thread into the pumphead block 300 at locations 711 and 713. The steps of the screws force heat spreader plate 390 against the pumphead 300. The stepped screws respectively have hand knobs 403 and 405 and compression wave washers 717 and 715 which force shroud 394 of cooling assembly 306 to the right, pressing finned aluminum extrusion 392 into good thermal contact with thermoelectric element 386.

The cooling assembly 306 may be removed from the pumphead 300 by unscrewing screws 398 and 401 with knobs 403 and 405, releasing the shroud 394 and fins 392, also releasing thermoelectric element 386 and heat spreader plate 390, which have been sandwiched between the finned extrusion 392 and pumphead 300. This provides access to the two stainless steel screws 715 and 717 (FIG. 12), the heads of which are recessed into pumphead block 300. These screws hold the pumphead to the spacer block 376 to the mounting sleeve 378. The removal of these screws provides for removal of pumphead block 300 so that seal 356 can be replaced if necessary.

Removal of cooling assembly 306 and heat exchanger 763 adds to the difficulty of getting access to seal 356 for its replacement. To compensate for this, it is desirable to increase the life of the seal so that replacement is less frequent. To this end, bearing sleeve 364 keeps the piston 304 centered very accurately within the center of seal 356, thus prolonging the life of the seal far past what is usual with this type of pump. This collinearity minimizes the radial stress on the seal and provides a remarkably longer seal life.

To insure that the center lines of sleeve bearing 364 and seal 356 follow the same line, the following three steps are initially taken in manufacturing the pumphead 300, which three steps are: (1) the bores 370 and 366 are made in pumphead block 300; (2) a solid rod of the material selected for the bearing sleeve 364 is turned to an outside diameter which forms a good force fit in bore 366; and (3) the sleeve 364 is then force fitted into bore 366.

After the sleeve 364 is force fitted into bore 366, the following two steps are taken, which are: (1) the pumphead block 300 is chucked in an accurate lathe and the recess or gland 366 for seal 356 is turned; and (2) without disturbing the lathe setup any more than is necessary to carefully change boring tools, the inside bore 368 of bearing sleeve 364 is bored, leaving the center of gland 366 and the center of bore 368 of sleeve 364 collinear.

After removal from the lathe, the following three steps are taken, which are: (1) if palladium is used for the bearing sleeve 364, the pumphead block 300 and the sleeve 364 are annealed at 820 degrees centigrade for five hours in a low pressure argon atmosphere and cooled in the atmosphere; (2) the cool pumphead block is removed from the heat treating furnace, the seal 356 is assembled into gland 366 and the backup disk 374 is assembled outside of it; and (3) before the pumphead block 300 is assembled onto bearing 354, which in turn floats radially within backup block 376, and within mounting sleeve 378, the cam 338 is rotated so that piston 304 is retracted until it does not protrude to the left much farther than shown in FIG. 7.

To permit rotation of the plunger 304 so that it is retracted, optical flag 722 (FIG. 12) and sensor 724 (FIG. 12) in cooperation with the pump controller, provide push-button capability for the user to operate the motor drive to rotate the cam 338 under program or computer control to a position that moves the piston 304 only so far out that it will fill about half or a third of the length of sleeve 364 when the pumphead block 300 is assembled onto support block 376 and guide sleeve 378. It is undesirable at this time for the plunger 304 to move further out, as this unnecessarily subjects it to increased chance of breakage when the pumphead is put onto the plunger.

Next, when the pumphead block 300 is inserted onto the rod or piston 304, the piston 304 becomes accurately constrained into position by the inside surface of bearing sleeve 364 well before backup ring 374 starts to compress and locate against radially floating bearing sleeve 354 when the pumphead block 300 is slid on over holding studs (FIG. 12), which are nutted and tightened. As a result, bearing sleeve 354 is collinearly located with respect to rod 304 and sleeve 364 before such compression.

After this compression, second bearing sleeve 354 becomes radially located and locked in place by compressive forces, such that its center axis is collinear with the center axes of first bearing sleeve 364 and rod 304. This leaves the piston 304 being constrained to reciprocate with its center axis collinear with the center axis of seal 356 since first sleeve 364 is collinear with the seal. The rod 304 is supported on both sides of the seal 356 by first and second bearing sleeves 364 and 354. The axis of rod 304, the axis of the bore in first sleeve 364, the axis of the seal 356 and the axis of the bore of second sleeve 354 are all collinear with respect to each other. The resulting accurate and robust collinear alignment of rod 304 with respect to seal 356 provides substantially and reliably increased seal life and there is negligible side-wise or misalignment wear of the seal.

The piston rod 304 is constrained to operate with close collinearity with the center axis of the pump chamber 336 since the bearing sleeve 364 is immediately adjacent and in the same block of metal. Thus, the pump chamber wall 370 of chamber 336 does not need to have an internal diameter which is much greater than the diameter of the piston 304, decreasing the unswept volume in the pumphead. It increases the compression ratio to 2.64 to 1, an amount which compares well to an embodiment wherein the spring in the seal 356 of this application is replaced with a solid plastic ring. The resulting high compression ratio is needed to provide the high volumetric efficiency required for high flow rate capability when pumping very compressible liquids to a high pressure.

Because the seal, sleeve bearing and plunger are located or imbedded within the pumphead rather than being located behind the pumphead as in some other pumps, there is no risk of the plunger running into the walls of the pumping chamber such as in the vicinity of the fluid passages 330 and 334 leading to the check valves and becoming chipped if the diameter 370 of the pump chamber is made small enough to obtain a good compression ratio. If the plunger were to become chipped, the plunger or the chips themselves could then destroy the seal, thus defeating the effort to prolong seal life by providing coaxiality of the plunger with respect to the seal.

To maximize the speed of repressurization and refill of the pump chamber 336 without increasing the peak torque seen by the mechanical parts of the pumping system, the maximum reverse torque due to depressurization of the fluid in the pump chamber 336 (FIG. 1), as seen by the motor 726 (FIG. 12) or the cam shaft 382 is made substantially equal to the maximum torque during delivery at maximum pressure. This minimizes operating noise and maximizes reliability. This is an important factor for pumps which pump prepressurized and compressible liquid, as is the case with pumps which pump liquids near their critical points, and also generally as pumps for supercritical fluid supply. It is important because of the high stored energy of compression which is not the case with high performance liquid chromatography pumps.

Figure 8:
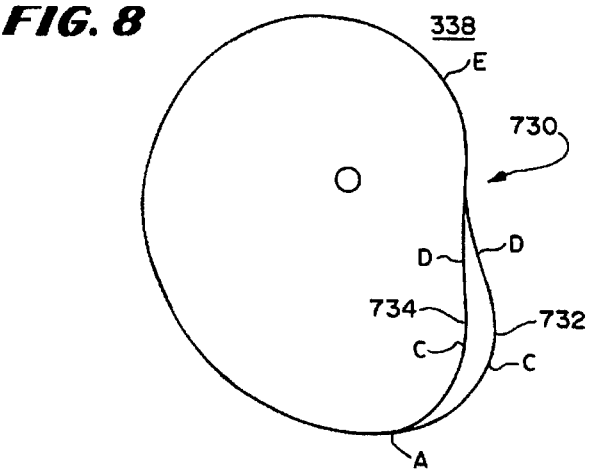
FIG. 8 is an elevational view of two supercritical cams showing the difference between a drive cam of an HPLC pump and the cam of this invention.
Figure 9:
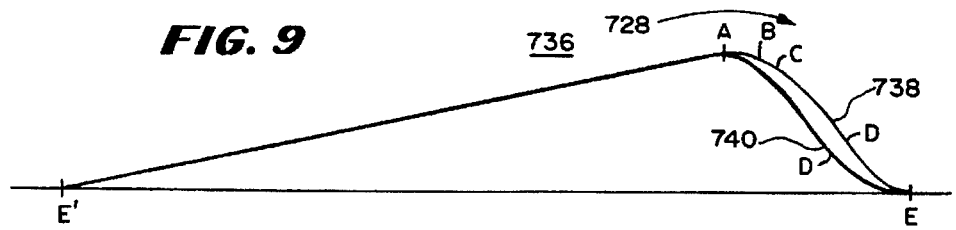
FIG. 9 is a developed curve illustrating the difference between a drive cam of an HPLC pump and the drive cam of the pump of this invention.

In FIGS. 8 and 9, there are shown two versions 730 of the cam 338 and two versions 728 of the cam-operated plunger displacement curve 736. The two version of the cam 338 shown at 730 differ from each other by the portions of the outline 732 and 734. The version with the shape shown at 732 is identical to the cam 338 in FIG. 7. The version with shape 734 has a shape similar to a conventional fast-refill HPLC pump cam.

In FIG. 9, there is shown a development or cam follower displacement profile 736 for a 0.75 inch cam follower indicating linear movement of cam follower 342 (FIG. 7) and piston 304 (FIG. 7) corresponding to one revolution of the cam. A 0.875 inch diameter cam follower has longer life and the difference in displacement profile is negligible. A comparison of the displacement profile of a HPLC cam with the cam 338 is shown at 728. The curve labeled 738 corresponds to cam surface 732 of cam 338 in FIG. 7 and the curve labeled 740 corresponds to a conventional fast-refill HPLC pump cam; cam surface 734 of cam 338. The HPLC-style cam (curve 740) produces a peak reverse torque of about twice the delivery torque at a pressure of 7500 psi. The cam 338 represented by development 738 produces a peak reverse torque equal to that of the delivery torque. This is accomplished without decreasing the time of the forward stroke (delivery direction) or increasing the time of the reverse stroke (i.e. depressurization and refill).

With this arrangement, the maximum delivery torque is not increased and delivery pressure pulsations are unchanged. This, of course, does not happen without foregoing certain characteristics of HPLC pump cams, such as for example: gentle refill followed by a wait (nearly zero cam follower velocity) region for the pump chamber to fill and the inlet check valves to close. This is necessary for HPLC pump cams to avoid cavitation. It is not necessary for supercritical fluid extraction supply pumps because the supply liquid pressure corresponds to room temperature vapor pressure and the liquid vapor pressure in the pumping chamber corresponds to a temperature about 10° C. lower.

Position A on the cam 338 (FIGS. 7 and 8) represents maximum radius of the cam or the top dead center (extended) position of piston 304. The point on the cam at which depressurization ends and refill of the pump chamber 336 starts is indicated as position C. The minimum radius of the cam is indicated as position E and corresponds to maximum volume in the pumping chamber 336 and maximum withdrawal of the piston 304. Positions A, C, D and E respectively correspond to rotational positions of cam 338 such that positions A, C, D and E are in contact with cam follower 342 and also relate to the corresponding position on the cam development 736 so that position E' occurs every 360 degrees of rotation, as better shown in the development 736 (FIG. 9) between E' and E. Starting at position E', a first part of surface E'-A is the repressurization surface. The remaining (second) part of surface E'-A is the delivery surface. The surface near and on each side of position A is the transition surface. Surface A-C is the depressurization surface and surface C-E is the refill surface.

Reverse torque reflected on the cam 338 by cam follower 342 is controlled to a value nearly equal to the delivery torque at cam positions extending from position A to position C. The starting slope of displacement after top dead center velocity of the cam follower 342 and therefore the piston 304 (after position A) should be equal and opposite to the displacement slope produced by the linear spiral contour of the cam before top dead center of the cam (before position A). The delivery surface displacement slope decreases to zero as it approaches position A. The displacement slope of the depressurization surface is zero at position A and then its magnitude increases to the negative of the delivery displacement slope. The resulting rounded area, the transition surface about position A, decreases Hertzian contact forces with the cam follower to prevent deformation of the cam, excess motion of the cam follower and allows the outlet check valve 308 (FIG. 7) to shut gently without damage because the velocity of the piston 304 and the velocity of the pumped fluid is low.

The displacement after top dead center is a function of cam rotation and should increase in an accelerating manner until position C. Position C corresponds to depressurization of the pump chamber to the supply pressure. In the case of carbon dioxide with a supply pressure of 870 psi, a fluid temperature of 15 degrees C and a head pressure of 7500 psi, the compression is about 1.25. This corresponds to an increase in pump chamber volume of 1.25 x the dead volume.

The displacement rate or plunger velocity with respect to cam rotation should accelerate continuously as cam rotation increases from position A to position C. Torque on the cam shaft is proportional to the displacement slope times the pressure on the piston 304. Therefore, torque on the cam shaft from position A to position C is kept constant if the slope of the displacement is proportional to the reciprocal of the pressure on the piston 304.

The pump chamber refills with supply liquid between positions C and E. During this period, it is desirable that the acceleration be small (nearly constant displacement velocity) as this is an efficient condition for receiving supply fluid with minimal pressure drop and minimal chance of vaporization. Such a relatively linear region is generally indicated as position D. For smooth running, it is desirable that there not be a discontinuity of slopes between the join of depressurization A-C and the refill surface C-E. By measurement of motor current, it has been discovered that pumps operating at constant rotational speed and incorporating this feature produce a depressurization torque (and also a refill torque) of the same magnitude as the delivery torque.

In one embodiment, the cam and the electric drive motor are permitted to passively overspeed during the reverse-torque interval of depressurization and refill of the pump chamber. This provides: (1) small but beneficial increase in the maximum pumping rate at high delivery pressures; and (2) simplifies the circuitry for the motor drive because the motor speed does not have to be controlled under reverse torque conditions. The servo loop is used to control the motor speed during fluid delivery and operates similarly to that disclosed in co-pending U.S. patent application Ser. No. 07/843,624; MULTIPLE SOLVENT DELIVERY SYSTEM, Daniel G. Jameson, et al. A motor drive system may be used in which each stroke of the reciprocating pump is controlled in a manner analogous to that of each stroke of a syringe pump in U.S. patent application Ser. No. 07/843,624. The major difference is that it has been found advantageous to combine the instantaneous pressure during delivery of a present pump stroke with the average or integrated pressure throughout the delivery of the previous pump stroke and to use this pressure information for pressure feed back purposes. Using this combined pressure feedback signal for motor control produces a more stable and accurate control system.

On a typical HPLC pump cam, the displacement curve just after position A has a shorter (usually less than half) radius of curvature than the displacement curve just before position E. The displacement curve after position A has a short radius to quickly traverse through depressurization and start the refill quickly so that the time for the refill period is relatively long and gentle. Gentle refill is necessary to prevent cavitation in the pump chamber as the incoming fluid is only at atmospheric pressure so the onset of cavitation inside the pumphead may be at a pressure of only 10 psi less than atmospheric. This pressure drop can readily be exceeded due to viscous and inertial fluid forces in the inlet valve and inlet line if the inlet stroke is too violent. Cavitation causes an unreliable or varying flow.

However, the pumping system 12 is supplied with a high pressure liquid such as carbon dioxide at 22° C., which is pressurized by its own vapor pressure of about 870 psi and thus is less susceptible to cavitation. The pump is cooled below 16° C., which reflects a vapor pressure that is at least 100 psi lower. This is about 10 times the suction pressure available to an HPLC pump.

At the end of the inlet period, the cam of a typical HPLC pump causes a gentle (large radius of curvature of displacement) deceleration and a lengthy dwell at nearly zero velocity to allow time for the inlet check valve 310 (FIG. 7) to close. This is necessary because the viscosity of HPLC mobile phases typically are ten times the viscosity of liquid carbon dioxide so the ball in the HPLC pump check valve falls closed more slowly. However, it is desirable for the displacement curvature of the pump of this invention to have a shorter radius at the end of the refill period to make up for time lost by the larger curvature during the depressurization. In the pump of this invention, the depressurization rate of curvature should be larger than the radius of curvature at the end of the refill period, and preferably at least twice as large. The depressurization displacement from A to C on curve 738 should require at least 1.5 times the cam rotation as the same displacement on curve 740. Curve 740 corresponds to the displacement of an ordinary single piston HPLC pump such as an Isco model 2350. For the $CO_2$ pump during refill, during displacement C to E the average displacement slope is at least 20% greater than that of such an HPLC pump.

As an example, for a pump with 80 microliters of dead volume and 120 microliters displacement with a 15 mm (millimeter) stroke, table 1 provides the preferred cam follower and plunger displacement rates or slopes with respect to cam rotation for plunger positions corresponding to the top dead center position through the position at which depressurization ceases and inspiration of new liquid starts.

The preferred displacement slope shown in Table 1 is obtained from curve 738 (FIG. 9) as follows: (1) row 1—7500 divided by 7500 equals 1; (2) row 2—7500 divided by 4460 equals 1.68; (3) row 3—7500 divided by 2400 equals 3.12; (4) row 4—7500 divided by 1350 equals 5.56; and (5) row 5—7500 divided by 870 equals 8.62.

In table 1, carbon dioxide is at 15° C. The relationship between pressure and volume was determined from tables in K. S. Pitzer et al., *J. Am. Chem. Soc.*, 77 3433 (1955). The relative delivery rate (displacement slope) just before position A is "S". Positions just before and just after A are referred to as A− and A+. Between these two locations, the cam surface is greatly rounded and the slope is zero at A. The calculation is based on isothermal expansion and does not seem to produce a large error.

In FIG. 10, there is shown an air-cooled inlet fluid heat exchanger 762 similar to the heat exchanger 763 (FIG. 7) for the pumphead and the cooling assembly 306. The heat exchanger 762 includes a spiral coil 742, an aluminum disk 744 and aluminum disk 746 and a thermoelectric cooling element 754. The thermoelectric cooling element 754 precools fluid entering the spiral coil 742 through tubing 770 connected to the coil 742 before the fluid reaches the inlet valve fitting 310 of pumping unit 12 (FIG. 7) through tubing 772 that connects the inlet valve fitting 310 (FIG. 7) to the coil 742.

The spiral coil 742 has 0.06 inch outside diameter by 0.04 inch inside diameter and is formed of stainless steel tubing sandwiched between aluminum disks 744 and 746. A bore of 0.04 inch is unusually large for this size tubing. The spiral

TABLE 1

| Cam follower displacement from position A+ to position C | | Volume in pump chamber ul | Pressure in pump chamber PSIG from Pitzer, et al. | Preferred Displacement slope (curve 738 from A+ to C on FIG. 9) During fluid delivery, slope = S. |
| --- | --- | --- | --- | --- |
| Position A+ | 0% | 80 | 7500 | −S |
| | 25% | 85.1 | 4460 | −1.68S |
| Position B | 50% | 90.2 | 2400 | −3.12S |
| | 75% | 95.4 | 1350 | −5.56S |
| Position C | 100% | 100.5 | 870 | −8.62S | coil 742 is in close thermal contact with disks 744 and 746 because of thermally conducting compound packed in the interstitial spaces such as indicated at 748. A screw 750 compresses aluminum disks 744 and 746 together, but a heat-conducting aluminum spacer 752 prevents serious flattening of spirally wound tubing 742.

The aluminum disk 744 is in good thermal contact with one side of thermoelectric cooling element 754 and with disk 746 through spacer 752. The thermoelectric cooler 754 is the same type as thermoelectric cooler 386 (FIG. 7). The second side of thermoelectric cooling element 754 is in good thermal contact with finned aluminum extrusion 392. The finned aluminum extrusion 392 is enclosed by sheet metal shroud 394 which defines forced air cooling passages between the fins such as 396. Four screws 756A–756D (only 756B and 756D being shown in FIG. 10) compress low thermal conductivity plastic clamping members 758A–758D (only 758B and 758D being shown in FIG. 10) against disk 746 by means of clamping force supplied by screws 756A through 756D and spring washers 760A–760D (only washers 760B and 760D being shown in FIG. 10) under the heads of these screws. The screws are threaded into the finned extrusion 392 and tightened sufficiently so that thermal contact on both sides of thermoelectric cooler 754 is obtained. The screws 756B and 756D, spring washers 760B and 760D, and clamping members 758B and 758D appear in FIG. 10. The other two sets are out of the plane of the section and do not appear on this figure.

The assembly formed of disks 744 and 746 and spiral coil of tubing 742 sandwiches thermoelectric cooling element 754 against finned aluminum extrusion 392 because disks 744 and 746 have four-point spring loaded clamping. Passing a current through thermoelectric element 754 causes the side of thermoelectric element 754 that is adjacent to disk 744 to draw heat from disk 744 thereby cooling it and cooling the spiral coil of tubing 742 and cooling the contents of the tubing within this spiral coil. Heat absorbed from aluminum disk 744 and electrical heat generated due to electrical resistance of the thermal elements within thermoelectric cooling unit 754 is rejected to finned aluminum extrusion 392. The heat is removed from finned extrusion 392 by air flow through the cooling passages, one of which is labeled 396, such air flow being in the direction into the plane of the paper. Note that liquid cooling is not used in any form.

The cooled length of the spiral wound coil of tubing 742 within heat exchanger 762 is 75 inches. With the tubing's internal diameter of 0.04 inch, this results in a heat exchanger volume of 1.5 milliliters. The volume of the heat exchanger should not be much less than twice the displacement of the pump 12, or largely uncooled liquid will shoot rapidly through the heat exchanger without adequate cooling during the inlet stroke of the pump. This makes the heat exchanger ineffective.

Increasing the heat exchanger volume to greater than twice the pump displacement further improves the efficiency of the heat exchanger, especially at flow rates greater than two milliliters per minute, due to the longer fluid contact time in the heat exchanger. In the preferred embodiment, the 1.5 milliliter heat exchanger volume is greater than ten times the 0.12 milliliter displacement of the pump. The length to diameter ratio of the wetted surface of the heat exchanger as described in the preferred embodiment is 1875 to 1. This provides a large contact area-to-volume ratio which efficiently cools the liquid, e.g. carbon dioxide, being pumped. For acceptable efficiency, the length to diameter ratio should be at least 50 to 1. Non-circular cross section heat exchangers should have a surface to volume ratio at least equal to that of a tube with a 50 to 1 length to diameter ratio.

In FIG. 11, there is shown a pumping system 1100 with pumphead block 300 (rest of pump not shown in FIG. 11) and the in-line heat exchanger 762 mounted to cooling assembly 306. A shrouded (box type) propeller fan 764 pulls outside air into the air passages 396 (FIGS. 7 and 10) of finned aluminum extrusion 392 as shown at 766. The fan 764 may be a Nidec #A30108 which produces an air flow of about 95 cfm at a static pressure of 0.05 inch of water. The air exits the passages 396 and is exhausted by the fan shown by the arrows 768. This, in cooperation with an electric current passing through thermoelectric cooling elements 386 (FIG. 7) and 754 (FIG. 10), cools the in-line heat exchanger 762 and the pumphead block 300.

In operation, liquid near its supercritical point enters the heat exchanger 762 through tubing 770, is cooled in its inward spiral passage through spiral coil 742 (FIG. 10) and exits the heat exchanger through tubing 772. Tubing 772 is connected to the tubing fitting located within threaded recess 320 (FIG. 7) of inlet check valve assembly 310 (FIG. 7).

To prevent liquid from warming up in its passage from heat exchanger 762 to pumphead block 300, tubing 772 is fitted with tubular thermal insulation 774 and the efficiency of cooling of heat exchanger 762 is improved by its insulated covering 776. Moreover, the efficiency of cooling of pumphead block 300 is improved by the cylindrical wrap of flexible insulation 778.

Thermoelectric coolers 386 and 754 are connected electrically in series and powered from a d.c. power source (not shown) at 2.5 amperes and about 11.5 volts each for Melcor CP1.0-127-05L thermoelectric elements or 3.8 amperes at 7.7 volts each for Melcor type CP1.4-127-045L thermoelectric elements. The Melcor CP1.0-127-05L thermoelectric elements pump about 14 watts of heat and the Melcor type CP1.4-127-045L thermoelectric elements pump about 16 watts of heat under these conditions. Both thermoelectric elements require the same amount of electric power to do this, which is 29 watts.

Figure 12:
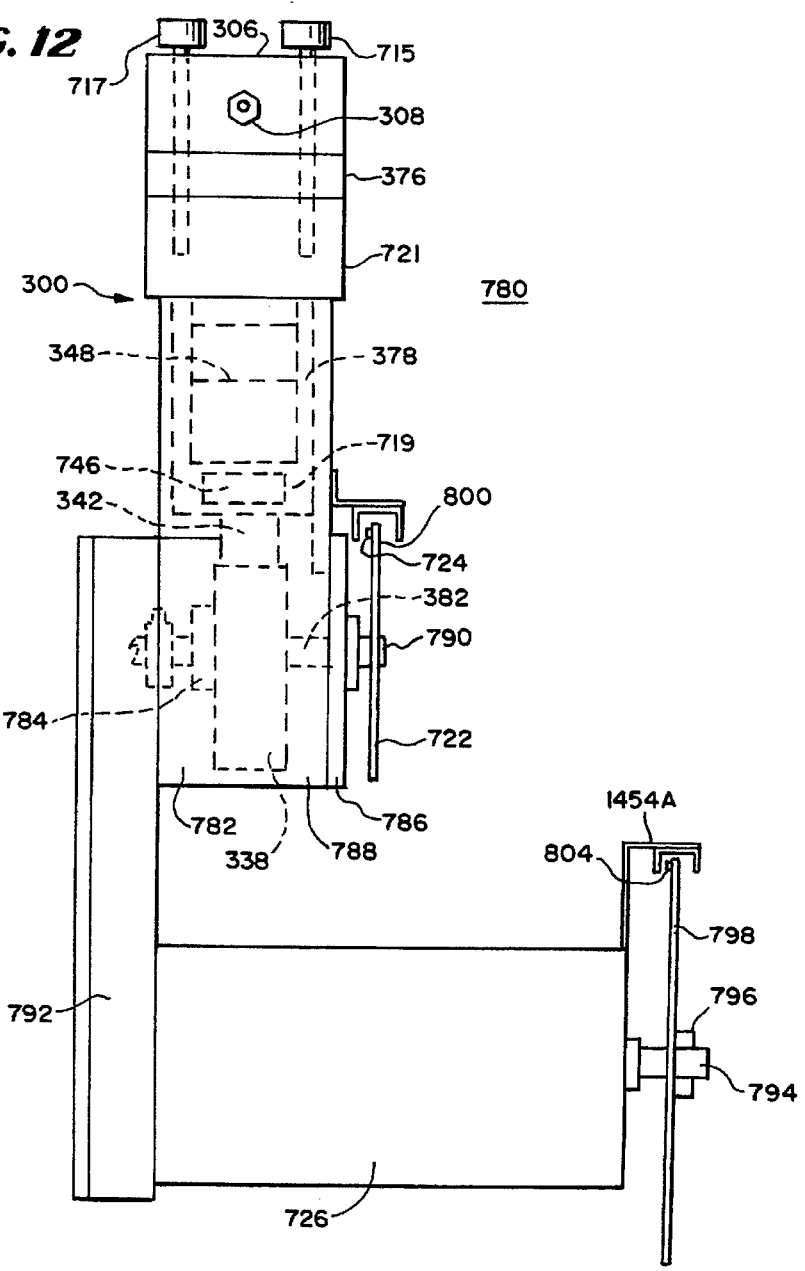
FIG. 12 is an elevational view of the pumphead including its drive cam, support bearings for the drive cam, a reduction gear box and an electric drive motor and position transducers which constitutes the pumping unit and its drive mechanism.

In FIG. 12, there is shown a simplified elevational view of a pumping module 780 having the motor 726, a transmission 792, the cam 338, the cam follower 342, the pumphead block 300 and the cooling assembly 306. The motor 726 is connected to the cam 338 through the transmission 792 to drive the cam 338 and cam follower 342 to operate the pump as described in FIG. 7. Threaded stainless steel studs 715 and 717 (FIG. 12) hold pumphead block 300 to mounting sleeve 378 with plastic support block 376 sandwiched between the pumping block and the mounting sleeve 378. The mounting sleeve 378 carries tapped holes for the studs and fits tightly within molded plastic pump body 782.

As described earlier, tubular slide 348 reciprocates within the bore of mounting sleeve 378. Its reciprocating motion is driven by rotating cam 338 which is in contact with roller bearing cam follower 342 which is supported by trunnion 344 (FIG. 7) located within the two yokes 346 (FIG. 7) which are an integral part of tubular slide 348. The cam 338 is supported by shaft 382 which in turn are supported by ball bearings 784 and 786.

Advantageously, the profile of the cam corresponding to the fluid delivery portion of its rotation is a linear spiral. The bearing 786 is mounted on removable plate 788 which is fastened to the plastic pump body 782. A hub 790 on shaft 382 carries optical flag 722 which cooperates with sensor 724 mounted on plate 788 which in turn is fastened to pump body 782.

As shown in FIG. 12, the flag location at 722 corresponds with the position of the cam as shown. When the cam rotates about 90 degrees, it is in the position which causes outward excursion of rod 304 sufficient for the rod to fill about half the length of sleeve 364 (FIG. 7). This position of the flag is shown by the phantom lines at 800. At this position, the flag 722 blocks the sensor 724, which produces an output signal indicating the aforementioned rod position. At about maximum outward excursion of the rod 304, the flag unblocks the sensor 724, providing an indication of essentially the end of fluid delivery from the pump chamber 336 (FIG. 7).

The transmission 792 includes a twelve-to-one reduction gear box that couples cam shaft 382 to the left shaft extension (not shown) of shaft 794 of drive motor 726. The drive motor 726 runs faster than shaft 382. The gear box is partially filled with oil to improve life of its internal moving parts. This oil is retained by a tight-fitting gear box cover.

Figure 15:
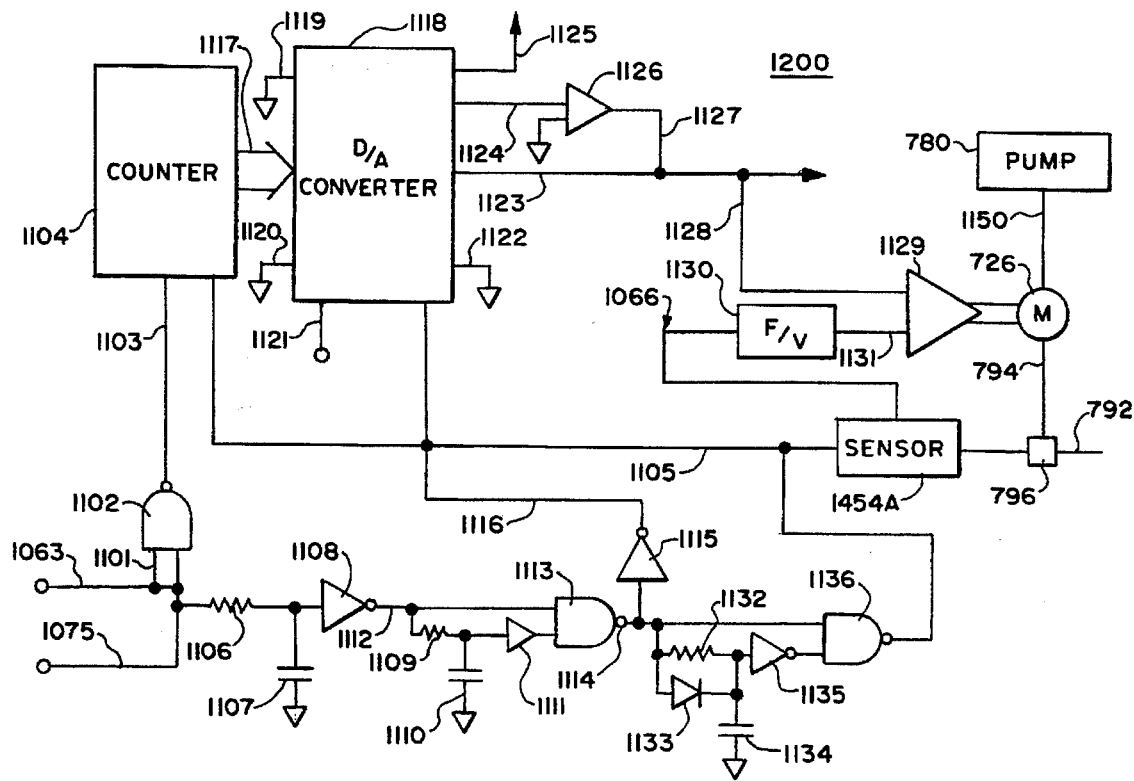
FIG. 15 is a schematic diagram of the constant flow controller for controlling the pump motor speed of the subject invention.

The visible end of the shaft 794 carries hub 796 which supports tachometer disc or encoder 798. Disc 798 is also shown in FIG. 15. Near its periphery, tachometer disc 798 (FIG. 12) carries a number of holes 804 (200 holes are convenient) which cooperate with optical sensor 1454A to produce a pulse repetition rate proportional to angular velocity of the rotor of motor 726 and its tachometer disc 798. Optical sensor 1454A, which produces this repetitive pulse, is mounted on bracket 805 which in turn is fastened to motor 726. The motor 726 may be a Pittman type 14205B749 24 volt d.c. motor.

With the above arrangement, a higher flow rate at any pressure including the maximum pressure of 7500 psi is provided than in a dual pumping system with the same individual kinds of components: insulated pumpheads, insulated heat exchanger, thermoelectric cooling elements, heat rejection means and cooling fans but with two pumping units simultaneously running in parallel. The head of one such pumping unit is thermoelectrically cooled but its inlet line is not cooled. The second such pumping unit is not cooled, but its inlet fluid is cooled by the heat exchanger. The two pump flows are added together and measured. The dual pumping system requires two of the relatively expensive pumping units rather than one, but has inferior performance. Thus, better results are obtained with fewer components even though, under a common corollary of the second law of thermodynamics sometimes referred to as "law of diminishing returns", the whole is, at most, equal to the sum of its parts; and usually is equal to less than the sum of its parts for thermal systems. The whole being less than the sum of its parts is particularly true when cascading thermal processes, such as the two stages of thermoelectric cooling. This is a surprising result. Moreover, the above described arrangement provides more predictable results and lacks erratic characteristics found in an arrangement having separate cooling arrangements.

Figure 13:
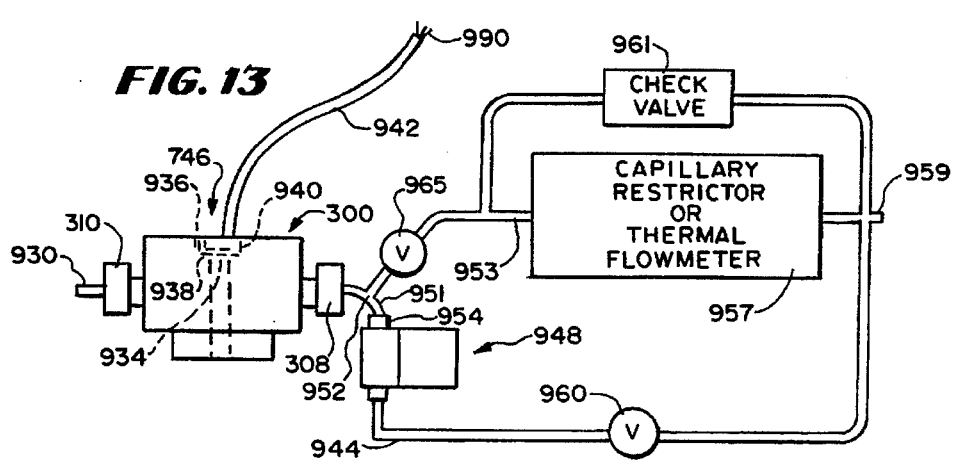
FIG. 13 is a schematic view of the pumping mechanism of the subject invention.

In FIG. 13, there is shown a simplified schematic view of the pumping system and a measuring system connected together for measuring flow rates and/or pressure and having for this purpose a pumphead block 300, an inlet valve 310, and an outlet valve 308, pressure transducer 948 for measuring the pulsating pressure associated with the pumping system 12 and a flowmeter 957 for measuring flow rates. There are at least two ways of measuring this pulsating pressure and at least two ways of measuring the flow rates.

To measure the fluctuating pressure within the pumping chamber 336 (FIG. 7) during the stroke cycle of the plunger rod 304 (FIG. 7), the front face of the pumphead has a counterbore 936 which leaves a relatively thin layer of metal 940 between the bottom of the counterbore 936 and the end of pump chamber 934. The thickness of the diaphragm thus formed at the bottom of the counterbore 936 must be sufficient to withstand the maximum pressure within the pumphead 300 at the fatigue endurance limit of the pumphead material.

A diaphragm pressure transducer strain gauge element 938 is cemented to the central portion of the thin layer of metal 940 at the end of the counterbore 936. The electrical leads 942 from gauge 938 are extended to a conventional differential amplifier (not shown in FIG. 13) which produces an output signal on (not shown) proportional to pressure within the pumphead.

Alternatively, commercially available flow-through pressure transducer 948 is connected to the outlet line 952 of pumphead 300 with the valve 965 closed and the valve 969 open to avoid flow to the flowmeter 957. The pressure fluctuations here are less and do not completely correspond to the fluctuations within the pumphead because of the action of outlet check valve assembly 308 (FIG. 7). Conductors 950 from the pressure transducer 948 are connected to a conventional differential amplifier whose output is proportional to the fluid pressure in pump outlet line 952. Line 959 conducts fluid to the utilizing apparatus such as a supercritical fluid extractor (not shown).

The pressure sensed by diaphragm strain gauge element 938 drops to the pressure in inlet line 930 during the refill stroke of the pump. The pressure sensed by pressure transducer 948 on the pumphead outlet line 952 does not generally drop either to zero or to the inlet pressure during the inlet stroke of the pump. This is because, although outlet flow from the pump stops during the inlet stroke, the pressure stored by the compliance of the compressible fluid in the high pressure fluid system connected to the outlet line maintains the pressure at a high level. However, there is some small to moderate decrease in pressure during the inlet stroke if fluid is flowing to an outlet, as for example, to supply a supercritical fluid extractor at moderate or high flow rate. At very low flow rate, if the extractor has a large internal volume, the decrease in pressure may not be enough to be useful. In such a case, recourse is made to measurement of flow changes instead of pressure changes.

To measure changes in flow in one embodiment, outlet line 952 is connected to outlet fitting 308 of pump 300, the pressure transducer 948 is connected to line 952 through line 951, line 953 is also connected to line 952 and leads to capillary restrictor 957. Valve 965 is open and 967 is closed. Fluid flows from the pump outlet fitting 308 through lines 952, 953, through restrictor 957, through line 959 and to a supercritical extractor. During fluid delivery, fluid flows from left to right through capillary restrictor 957. This causes the pressure at line 953 to exceed that of the pressure in the supercritical extractor. This flow-induced pressure rise sensed by pressure transducer 948 is indicative of delivery of fluid from the pump.

At sufficiently high flow rates, the pressure drop across restrictor or flowmeter 957 may become inconveniently high. The pressure drop may be high enough to noticeably decrease the flow from the pump, especially at high extraction pressures. A spring-loaded check valve 961 may be connected across the restrictor or flowmeter 957. This check valve can be set to crack open at a convenient pressure such as 50 or 100 pounds per square inch, so that the restrictor 957 does not increase the head pressure seen by the pump 300 by more than this amount at high flow rates.

In another embodiment, a thermal flowmeter is included at 957 to measure flow from the pump 300 to the supercritical extractor and the valve 967 is closed. Flow from the outlet to the pump flows through lines 951 and 953 to an electrically insulated coupling to a conventional thermal flow sensing tube. The flow sensing tube is coupled by another electrically insulated coupling to line 959 to the inlet of the supercritical extractor.

Preferably, the electrically insulated tube is made of a metal having a relatively high temperature coefficient of electrical resistance. Its inside diameter should be no more than that necessary to carry the maximum desired flow without increasing the head pressure seen by pump 300 to a point where it produces a noticeable degradation in maximum flow rate at maximum operating pressure. This tube should have a low thermal mass, so its wall thickness should be no more than necessary to reliably sustain maximum operating pressure.

Electrical leads couple a conventional electrical readout device to the ends of the electrically insulated tube. The readout device produces an electrical current which flows through the electrically insulated tube. This current is of sufficient magnitude to appreciably heat the tube when there is no flow through the tube. The tube cools down in response to flow coming from pump 300. Flowing fluid removes heat from the tube, which is warmer than the fluid. This drop in temperature decreases the tube's electrical resistance which is sensed by the electrical readout device. An electrical output from the readout device may be used in place of the electrical readout from the pressure transducer 948.

If at the maximum desired flow rate the pressure drop across the tube is enough to noticeably degrade the performance of pump 300, spring-loaded check valve 961 may be connected in parallel with it. With this arrangement, the pressure seen by pump 300 never exceeds the pressure at the inlet of the supercritical extractor plus the cracking pressure of the spring-loaded check valve 961. If rapid response is required to sense the start of a flow having a very low flow rate, it may be desirable to use a readout device that maintains the sensing tube at a constant temperature, and in which measurement is made of the voltage, current or power required to keep the tube at such constant temperature. This measurement indicates flow. Controllers for keeping a flowing fluid filled tube at constant temperature are described in co-pending U.S. patent application Ser. No. 08/027,257, APPARATUS AND METHOD FOR SUPERCRITICAL EXTRACTION, Daniel Gene Jameson, et al.

A further refinement is to divide the sensing tubing into two sections with the upstream section not being heated and the downstream section being heated. The temperature of both sections is measured by a controller and the downstream section is heated to a temperature that is a constant amount warmer than the upstream section. This provides greater reliability over a wider range of flow rates, ambient temperatures and fluid supply temperatures.

Figure 14:
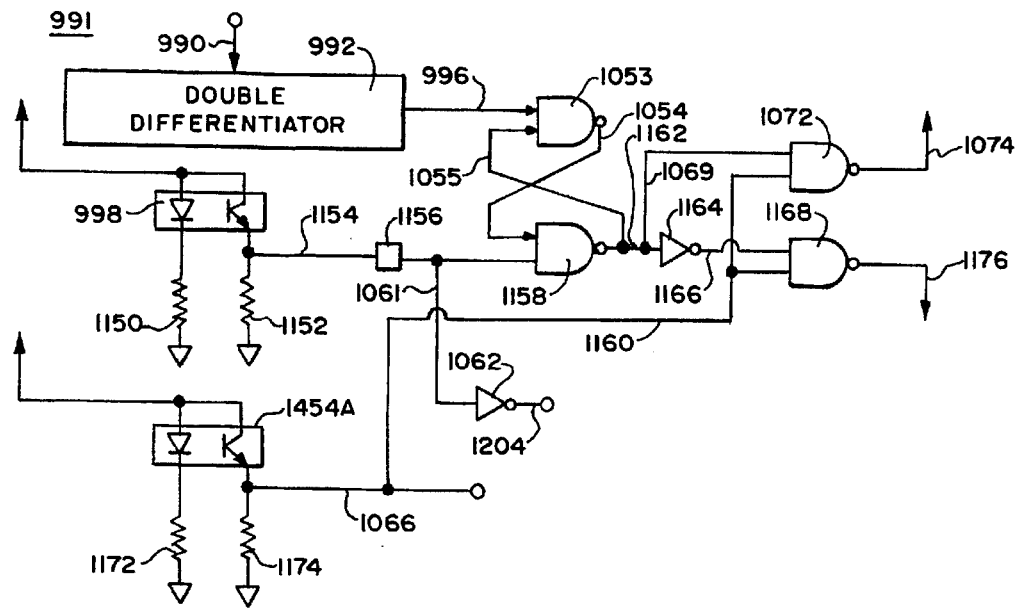
FIG. 14 is a schematic circuit diagram of a control circuit useful in the embodiment of FIG. 13.

In FIG. 14, there is shown a schematic circuit diagram of a first measuring circuit 991 for accurately determining the flow of a pump that pumps a very compressible liquid by measurement of pumping conditions. For this purpose, the measuring circuit 991 includes, as its principal components, a double differentiator or differentiating amplifier 992, AND gate 1053, optical approximate-dead-center sensor 998, inverted pulse former 1156, AND gate 1158, invertor 1164, AND gate 1168 and a tachometer sensor 1454A.

To determine the rate of flow from the end-of-stroke information and the start-of-fluid-delivery information according to a first method and using circuit 14, a pressure signal from pump chamber pressure transducer element 938 is applied to the double differentiator 992 on conductor 990, and in response, the double differentiator 992 transmits a pulse on conductor 996 to one input on AND gate 1053. The pump 300 (FIGS. 12 and 13) is equipped with optical approximate-top-dead-center sensor 998 (FIG. 14). This sensor has its light emitting diode current set by resistor 1150 and load resistor 1152 senses the current.

This potential drop across load resistor 1152 representing current flow produces a voltage on conductor 1154 which is at a logic high level except during the time that flag 722 (FIG. 12) breaks its light path. The following re-establishment of this light path produces a logic-high level which is applied to inverted pulse former 1156.

The pulse former 1156 produces a logic-low level pulse of 5 microsecond duration which corresponds to the onset of the approximate top dead center condition. The low voltage on conductor 1061 appears at an input of AND gate 1158. AND gates 1053 and 1158 are connected R-S flipflop by leads 1054 and 1055.

When the double differentiator 992 applies a negative pulse to input lead 996 of this R-S flip flop, the conductor 1162 latches to logic low. This low is conducted to the input of invertor 1164 whose output 1166 goes positive. This enables AND gate 1168 so that it accepts the pulse train on conductor 1160.

Figure 17:
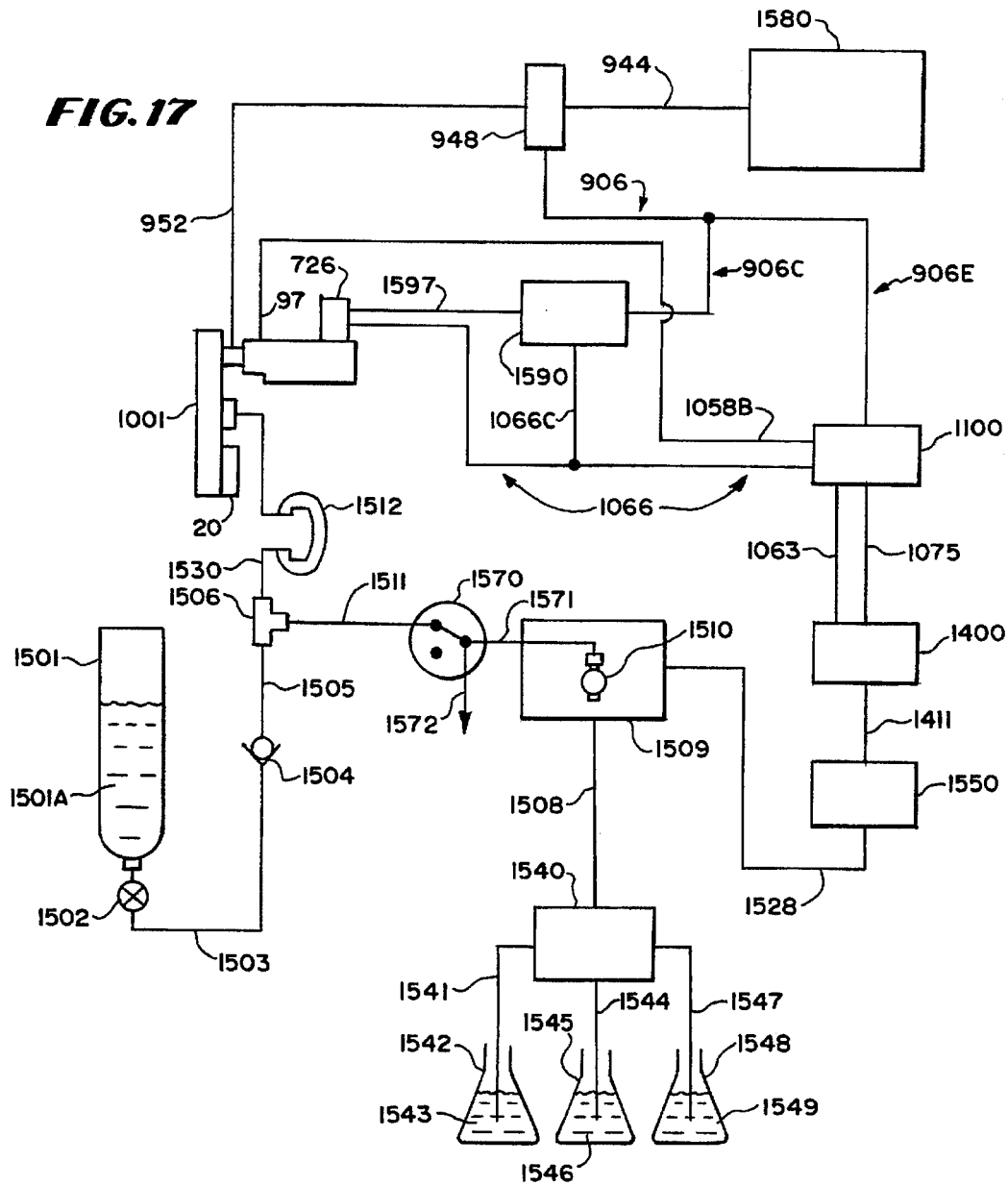
FIG. 17 is a schematic diagram of the gated flow pulse generator and flow rate indicator controller of the subject invention.

This pulse train on conductor 1160 is derived from tachometer sensor 1454A which monitors the motor speed via tachometer disc 798 (FIGS. 12 and 17). A resistor 1172 sets the current through the light emitting diode of optical sensor 1454A and current through the phototransistor of sensor 1454A flows through resistor 1174 which produces the train of voltage pulses corresponding to the passage holes 804 (FIG. 12) of tachometer disc 798 passing through the light path of optical sensor 1454A. As AND gate 1168 is enabled when output 1166 is high, the gate's output lead 1176 produces gated tachometer pulses representing flow volume during fluid delivery from pumphead 300.

At the end of the delivery stroke, approximate top dead center sensor 998 senses the passing of optical flag 722 (FIG. 12) on cam shaft 382 (FIG. 12), producing logical high level on lead 1156 and a logic low pulse on lead 1060. This resets R-S flipflop composed of NAND gates 1053 and 1158, putting logic high level on lead 1162 and invertor 1164, and therefore a low level on 1166, shutting off AND gate 1168 and stopping the pulse train on 1176.

The number of pulses in the train of pulses corresponding to each stroke of piston 304 and appearing at the output 1176 of NAND gate 1168 is proportional to high pressure fluid delivery from the pump during that stroke. Other pulses are available from this logic circuit. The pulse train at lead 1066 corresponds to the continuous tachometer signal representing the entire operating dynamic speed range of the pump motor 726 (FIG. 12). The output on lead 1204 from invertor 1062 goes to a logical high during the time that the optical flag 722 (FIG. 12) stops interrupting the optical sensor (corresponding to sensor 724 on FIG. 12). This logic high level starts at the time the cam 338 reaches top dead center. NAND gate 1072 produces an output on lead 1074 that is the compliment of the output on the lead 1176. The lead on 1074 is the pulse train representative of that part of the drive motor rotation corresponding to no flow from the pumphead.

For example, it is desirable to know the flow rate when pumping at constant pressure, which is often the case with supercritical fluid extraction systems. The typical pressure within pumping chamber 336 (FIG. 7) of pumphead 300 during a complete stroke cycle, starting with the plunger rod 304 having been moved all the way to the left (minimum displaced volume) is 6000 psi.

The pump cycle then includes the rod 304 relatively rapidly moving toward the right to refill the pumping chamber, and then moving back again more slowly to the left to repressurize the pumping chamber and to deliver fluid from the outlet of the pump. A typical, though by no means limiting, operating pressure is 6000 pounds per square inch. Pressure within the chamber 336 starts at 6000 pounds per square inch during the final stages of a previous delivery stroke, at which time the piston 304 reverses and the pressure drops toward the inlet pressure which is typically 800 psi, the vapor pressure of carbon dioxide at room temperature.

The pressure in the chamber 336 is at 870 psi in the preferred embodiment when the pump chamber fills through check valve 310 (FIG. 7) connected to the inlet line leading to the source of suitable liquid such as liquified carbon dioxide. The rod 304 reaches its maximum rightward excursion, refilling stops, and the rod starts to return to the left, compressing liquid carbon dioxide ahead of it. The pressure during this time rises from its lowest level.

When the pressure within the pumping chamber 336 reaches the pressure of the outlet line and whatever system is connected to it, the check valve 308 opens. The pressure within the pump chamber 336 when outlet check valve 308 is open, during fluid delivery, is a few percent lower than the 6000 pounds per square inch at the end of the previous stroke. This is because the fluid using system has drained some of the fluid from the high pressure line and its associated fluid holding components thereby dropping the pressure.

During the delivery stroke, the pressure gradually rises until at the end of the delivery stroke, the pressure is back to the original 6000 pounds per square inch. At this time, the plunger rod 304 has completed the leftmost portion of its stroke and starts to retract. This causes the pressure to drop, repeating the cycle described. The pressure during the fluid delivery period varies only slightly during the stroke. The average pressure can be considered a close approximation to constant pressure. If the velocity of the piston rod 304 is integrated over the delivery time, the result is the volume delivered per complete stroke-cycle of the piston 304.

If the portion of cam 338 (FIG. 7) corresponding to the delivery stroke of (leftward stroke) of the rod 304 is a linear spiral then the integration for determination of flow per pump stroke can be accomplished by integrating the pump drive motor speed over the delivery time. The terminal part of this interval is easily found as it corresponds to the top dead center position of cam 338 or it can be taken as the time that the pressure in the pump chamber 336 stops rising. The former may be determined by the output of sensor 1454A (FIG. 12) which produces a signal from optical flag 722 (FIG. 12) corresponding to near top dead center location of the plunger rod 304. Measurement of the motor speed for the integral is easily accomplished by counting the pulses in the pulse train produced by optical sensor 1454A (FIG. 12) in cooperation with tachometer disc 798 mounted on the shaft 794 of motor 726 which drives cam 338 through gear box 792.

The significant problem is to determine the time at which fluid delivery begins on each cycle of plunger rod 304. This is conveniently accomplished by single or double differentiating the pumphead pressure signal versus time. A first differential corresponds to the initial increasing downward slope of pressure during a refill. The signal levels off after falling because of the saturation limit in the electronics of the differentiator.

The signal gradually increases as the pressure increases during the time that fresh liquid carbon dioxide flows through the inlet check valve into the pump chamber 336 and then generally linearly increases as the leftward motion of piston 304 builds pressure up within the pumping chamber 336. The signal then decreases in rise as pressure decreases is rise within the pumping chamber when the outlet check valve 308 opens at the time the pressure in the pumping chamber slightly exceeds the pressure in the outlet line. The signal increases slowly corresponding to the few percent increase in pressure during delivery until a drop at the beginning of the next pump cycle.

The first differential or first derivative of the pressure in the pump chamber can be used to detect the end of a pump delivery stroke as the signal goes from a small positive value to a larger negative value. This information may be used interchangeably with the signal from the end-of-stroke sensor 724 (FIG. 12). It can also be used to detect the beginning of fluid delivery on the next stroke as the differential signal goes from a larger positive level to a lower positive level.

The second differential or the second derivative provides a negative pulse that corresponds to the downward slope of the first derivative and a positive pulse that corresponds to the upward slope of the first derivative. The first derivative corresponds closely with information derived from the optical sensor flag 722 (FIG. 12). The second derivative negative pulse occurs just at the time of initiation of delivery and therefore can be used to start the integration process which determines delivery per pump stroke.

When making a flow rate determination by a second method, the output pressure or flow of the pump by pressure transducer 948 or thermal flowmeter 957 is monitored (FIG. 13) instead of measuring the head pressure of the pump with diaphragm transducer strain gauge means 938 (FIG. 13). Assuming that the pressure transducer 948 is used to effect this method, that the pressure at the output of the pump at the start of a stroke is 6000 psi and that the piston is at the end of its previous stroke, then the pump passes top dead center, it first depressurizes the remaining liquid trapped within the pumphead, then inspirates additional liquid from the supply reservoir, and finally, the rod 304 (FIG. 7) repressurizes the inspired liquid to the delivery pressure. During this time, the pressure at the outlet of the pump as sensed by transducer 948 (FIG. 13) is dropping because of demand from the connected system such as a supercritical fluid extractor.

Typically, the pressure drops a few percent during this time. If the initial pressure is 6000 psi, the pressure may drop to say, 5850 psi. At this point, the content of pump chamber 336 (FIG. 7) is repressurized to the point where it slightly exceeds the head pressure and outlet check valve 308 (FIG.

7) opens admitting pressurized fluid to the outlet line. The pressure gradually rises from its starting level to its final level of 6000 psi. The integration points can be determined with a single differential (single time derivative) instead of a double derivative and processed and used as described above.

The pressure signal on the conductors 950 (FIG. 13) from pressure transducer 948 is amplified by a differential amplifier (not shown) and conveyed to a single inverting differentiator. A suitable double differentiator for 992 (FIG. 14) is described in U.S. Pat. No. 4,882,063. A suitable single inverting differentiator is derived from half of the double differentiator shown in U.S Pat. No. 4,882,063. The logic circuitry is the same as in FIG. 14 when a single inverting differentiator is used and produces signals including the gated tachometer pulses on lead 1176 representing flow volume during the time that there is fluid delivery and pulses during the time that there is no fluid delivery. Gated output pulses representing flow are available on lead 1176.

To use flow sensor information instead of pressure information, to detect the start of fluid delivery for each stroke, a signal representing flow information based on information from pressure transducer 948 in conjunction with a capillary restrictor (FIG. 13) or from information relating to the resistance of the sensing tube in thermal flowmeter 957 (FIG. 13) or the power supplied to the sensing tube by electrical sensing unit in flowmeter 957 is high during times of flow from forcing fluid through the capillary restrictor or the power signal is at a higher power level for the heating tube in flowmeter 957 to keep it a constant temperature as the flow carries heat away. Since this signal is not zero-based, it either needs to be adjusted with respect to a zero level by conventional fixed or tracing means or differentiated by a conventional differentiator.

The latter will be used for the purpose of this explanation. The first differential of this signal is a short spike that appears at the output of differentiator 992 on line 996 (FIG. 14). This signal is applied to the input of RS flip-flop element 1053 and operated upon gated tachometer pulses on indicating pump displacement during periods of delivered flow and gated tachometer pulses on lead 1074 when there is no delivered flow.

In an alternative to the embodiments already described in regard to FIGS. 13 and 14, flow can be determined by integrating cam or drive motor rotation over the depressurization, inlet and repressurization time 396, and subtracting this from the known constant integral corresponding to a full cam rotation. It is also often desirable to pump at constant flow rate, which is difficult to do with any accuracy if the fluid is highly compressible.

In FIG. 15, there is shown a constant flow controller 1200 for controlling the pump motor speed for constant flow regardless of fluid compression, using the gated pulses relating to flow from the arrangements of FIGS. 13 or 14. These tachometer pulses cannot be used as feedback to directly control a servo-operated pump motor. This is because the discontinuous nature of the pulses would cause the pump motor rotor to jump and buck while it is running over the pumping cycle.

As shown in FIG. 15, the gated tachometer pulse train can be used to control the setpoint voltage for a motor velocity control servo for the pump. It controls the motor speed to a constant value which is updated after each pump stroke. The same sort of scheme can be used to control an updated motor rotor angle location for a position control servo. The basic idea is to divide the setpoint voltage (or digital setpoint signal) by an amount equal or proportional to that part of the revolution time of the cam 338, which occurs during actual delivery of fluid. The latter is proportional to the number of gated flow pulses per stroke. Equations 1–8 together are a mathematical explanation of why this division is made.

In the operation of the embodiment of FIG. 15, at the end of a preceding delivery stroke, the voltage on lead 1063 goes high for 5 microseconds. This is applied to OR gate 1102 which ensures that no pulses which erroneously may be on lead 1075 are transmitted through lead 1103 to the clock input of 12-bit binary counter 1104. After a 1.6 microsecond delay provided by resistor 1106, capacitor 1107 and Schmidt inverter 1108, lead 1112 goes negative. OR gate 1113 in cooperation with resistor 1109, capacitor 1110 and inverter 1111 produce a 600 nanosecond low logic level pulse on lead 1116 which is connected to the "write" inputs of digital-to-analog converter 1118.

A flow rate setpoint voltage "$V_s$" is applied to the feedback resistor port (lead 1125) of converter 1118. The counter 1104 is a type 4040B and the digital analog converter is a type DAC1210. The logic low pulse on lead 1116 causes digital-to-analog converter 1118 to read and store the 12-bit pulse count signal on 12-bit line 1117. The output of OR gate 1113 on lead 1114 is also conducted to OR gate 1136 which in cooperation with resistor 1132, diode 1133, capacitor 1134 and inverter 1135 produces a 600 nanosecond positive pulse on lead 1105. This resets counter 1104 to zero.

The start of the next train of gated flow pulses from AND gate 1168 in FIG. 14 occurs after all of the logic voltage levels are back to their normal low level. Flow pulses are conducted on lead 1075, through OR gate 1102 and into the clock input of counter 1104. The counter counts these flow pulses and completes an output on 12-bit binary coded lead 1117 at the end of fluid delivery when the flow pulses stop. This output is then entered into the digital to analog converter 1118 when lead 1116 goes low as described above. This process repeats for every stroke of the pump, providing an updated motor speed setpoint at the end of every stroke as will be described below.

Operational amplifier 1126 may be a type 308A. The output lead 1127 of amplifier 1126 is connected by lead 1123 to the reference port of converter 1118. Digital to analog converter 1118 and operational amplifier 1126 are connected so that the analog input voltage $V_s$ is divided by the 12-bit binary number on lead 1117. This is in accordance with FIG. 14 and its accompanying explanatory information found on page 4–70 of *National Semiconductors Linear Databook 2*, Rev. 1, 1988 Edition.

Eq. 1: V setpoint = $k_1$ × average outlet flow rate = $V_s$ [FIG. 15]

Eq. 2: Average outlet flow rate =

$$\frac{k_2 \times \text{gated flow pulses per stroke}}{\text{(total pulses per cam revolution)} \times \text{(time per cam revolution)}}$$

Eq. 3: Let "total pulses per cam revolution" = $k_4$

Eq. 4: $V_{fb}$ = servo feedback on lead 1131 =

$$\frac{k_3 \times \text{total pulses per cam revolution}}{\text{time per cam revolution}} = \frac{k_3 k_4}{\text{time per cam revolution}}$$

Eq. 5: $V_{control}$ = control signal on lead 1128 = $V_{fb}$ [by servo action]

Eq. 6: $V_{control} = \dfrac{k_3 k_4}{\text{time per cam revolution}}$ $$\text{Eq. 7:} \quad \frac{V_{control}}{V_{setpoint}} = \frac{(k_3 \, k_4)}{(\text{time per cam revolution})} \times$$

$$\frac{(k_4 \times \text{time per cam revoltion})}{(k_2 k_1 \times \text{grated flow pulses per stroke})}$$

[from Eq's 1,2,3 and 6]

$$\text{Eq. 8:} \quad V_{control} = V\text{ setpoint} \times \frac{(k_5)}{(\text{gated flow pulses per stroke})}$$

The output voltage on lead 1123-1127-1128 is proportional to $V_s$ divided by a number proportional to the number of gated flow pulses per stroke. This is in accordance with Eq. 8, and is the control voltage which sets the speed of the pump motor. The voltage is updated after every delivery stroke. It is applied on lead 1128 to the conventional velocity servo composed of servo amplifier 1129, pump drive motor 726, shaft 1150, pump 780, shaft 794, tachometer 798, sensor 1454A, and frequency-to-voltage converter 1130 which closes the servo loop.

The pump speed is kept proportional to the control voltage by servo action. This keeps motor speed and pump speed at a rate which produces a flow rate directly and constantly proportional to flow rate setpoint voltage $V_s$.

Instead of the constant flow rate operation described above, the pump may be run in constant pressure operation. Constant pressure circuitry is known in the art. Examples include U.S. Pat. Nos. 3,985,467 and 4,775,481. It is desirable to have a supercritical fluid supply system capable of metering or proportioning in other fluids to modify the properties of the supercritical fluids. An example of doing this with constant flow operation is U.S. Pat. No. 3,398,689. An example of doing this with constant pressure operation is found in U.S. patent application Ser. No. 07/843,624 by D. G. Jameson and R. W. Allington, filed Feb. 27, 1992, the disclosure of which is incorporated herein by reference.

Figure 16:
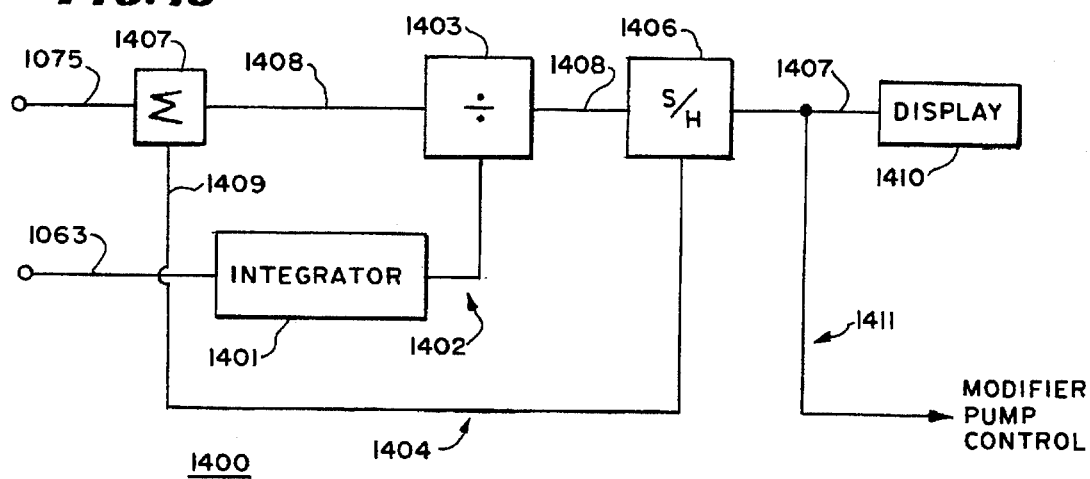
FIG. 16 is a block diagram of the flow rate indicator/controller used to determine the actual flow rate for the constant pressure operation of the subject invention.

For constant pressure operation, it is useful to know the actual flow rate. In FIG. 16, there is shown a flow rate indicator/controller 1400 which accomplishes this utilizing the gated flow pulses on lead 1075 and cam revolution pulses on lead 1063. It will be appreciated that the actual flow rate is equal to flow quantity per unit time and proportional to the number of gated flow pulses during a cam revolution, per revolution time of the cam 338.

Gated pulses representing actual flow quantity are delivered on lead 1075 (FIG. 15 and 16) to counter 1407 during one stroke of the pump. At the end of fluid delivery for that stroke, the output of the counter on lead 1408 represents the fluid delivered. This output is led to the numerator input of divider 1403. Five microsecond pulses representing the completion of each revolution of the cam 338 are lead on lead 1063 to the input of integrator 1401.

The output on lead 1402 of integrator 1401 represents the time for cam 338 (FIG. 7) to make one revolution. During the five microsecond pulse on lead 1063, the integrator 1401 and the counter 1407 freeze or hold their outputs constant. The integrator 1401 and counter 1407 reset just after each pulse on lead 1402. The output on lead 1402 is connected to the denominator input of divider 1403, so the output of the divider on lead 1408 corresponds to the flow rate during the five microsecond pulse on lead 1063. During this time, sample and hold 1406 stores the flow rate signal on lead 1408 because it is activated by the five microsecond pulse on lead 1404.

A flow rate signal relating to the immediately preceding pump stroke is present at the sample and hold output lead 1407. The flow rate signal on lead 1407 is led to display 1410 which displays actual flow rate regardless of whether the pump is operating in a constant flow mode or a constant pressure mode. This signal may also be used for control purposes, as in the control of a fluid modifier pump which meters modifier fluid into a supercritical fluid in selected proportion to the actual supercritical fluid flow rate regardless of whether the pump is operating in a constant flow mode or a constant pressure mode. A supercritical fluid flow rate signal for such proportional control is available on lead 1411.

In FIG. 17, there is shown the use of the gated flow pulse generator 1100 (also see FIG. 15) and the flow rate indicator/controller 1400 (also see FIG. 16) in a constant-pressure supercritical fluid extraction system for the purpose of controlling a fluid modifier pump so that it meters modifier fluid into the inlet of the supercritical fluid pumping system 1570 (FIG. 17) in selected proportion to the rate at which supercritical fluid enters the inlet of supercritical fluid extractor 1580.

A tank 1501 supplies liquid carbon dioxide 1501A through valve 1502 and inlet line 1503 to the inlet line check valve 1504. The outlet of check valve 1504 is connected to line 1505 through a first arm of tee 1506, out a second arm of tee 1506 to a Bourdon tube or other pressure pulsation damping and fluid storage device 1512. The outlet of Bourdon tube 1512 is led through line 770 to pre-cooling heat exchanger 762 (FIG. 11). The outlet of this heat exchanger is led through line 772 (FIG. 11) to the inlet of reciprocating pump 780 (FIG. 12). The pumphead block of pump 780 and the pre-cooling heat exchanger 762 (FIG. 11) are cooled by thermoelectricelements (not shown) which are thermally connected to heat rejection means 306 which is directly air-cooled by fan 764 (FIG. 11). The items 762, 780, and 306, and the thermoelectric cooling elements are as described hereinabove.

The outlet of pump 780 is connected by line 952 (FIG. 13) to the inlet of flow-through pressure transducer 948 (FIG. 13). The outlet of pressure transducer 948 is connected by line 944 (FIG. 13) to the fluid inlet of supercritical fluid extractor 1580 which may be one of the types of supercritical fluid extractors described in the parent application. An electrical signal from pressure transducer 948 (FIG. 13) indicating fluid pressure in line 944 (FIG. 13) is carried by lead 906 (FIG. 13) and 906C to constant pressure pump control 1590. The control 1590 may be of one of the types of known constant pressure pump controls referenced earlier in this disclosure.

The control output of constant pressure control 1590 is conducted on lead 1597 and power drive motor 726 (FIG. 12) of pump 780. The drive motor 726 is equipped with tachometer means (not shown) which supplies an electrical signal indicative of its rotational speed on line 1066 to gated flow pulse generator 1100 and on line 1066C to constant pressure pump control 1590. The pump control 1590 may use motor rotational speed and position information and pump outlet pressure information to control pump speed to obtain constant pressure in accordance with known techniques referenced earlier. A cam position transducer (722–724 on FIG. 12, not shown on FIG. 16) which is part of pump 780, produces an electrical signal on lead 1058B indicative of pump cam and plunger position and supplies this signal to a second input of gated flow pulse generator 1100. A signal indicative of fluid pressure in line 944 is supplied to a third input on gated flow pulse generator 1100 on line 906E.

As described previously in this disclosure, generator 1100 produces an electrical output on lead 1063 which is a 5 microsecond pulse indicative of cam position near the top dead center minimum chamber volume of each stroke of the pump 780. The second output on lead 1075 from generator 1100 is gated pulses which correspond to the rotation of the motor 726 and therefore rotation of the cam (not shown) in the pump 780 during actual flow delivery on fluid lead 952 (FIG. 13) at the outlet of the pump. Leads 1063 and 1075 are connected to the two inputs of flow rate indicator/controller 1400. As described previously in this disclosure, control 1400 produces a voltage on lead 1411 which is proportional to the actual flow rate of fluid through line 952 (FIG. 13).

Lead 1411 is connected to the input of % modifier adjustor/programmer 1550. Adjustor/programmer 1550 may be a conventional potentiometer to scale the voltage on lead 1411 to provide a control signal on lead 1411 which is connected to the analog control input of liquid pump 1509. Alternatively, adjustor/programmer 1550 may have program means such as one of the two program channels disclosed in U.S. Pat. No. 3,398,689 to allow programming of the percentage of fluid pumped by pump 1509 with respect to the total amount of fluid flowing through line 952 (FIG. 13). Liquid pump 1509 may be an Isco Model 2350 HPLC pump which accepts a 0 to 10 volt d.c. signal on lead 1528 to control the flow rate produced by its pumphead 1510.

The check valve 1504 prevents back flow of modifier liquid from pumphead 1510 into supply tank 1501. This back flow could otherwise happen because most of the time the pump 780 is discharging liquid and rather little of the time it is inspiring liquid. During the discharge time, excess liquid from pumphead 1510 is stored by expansion of bourdon tube 1512.

The inlet of pumphead 1510 is connected by lead 1508 to solvent selector and mixer 1540. Solvent mixer and selector 1540 may be an Isco Model 2360 composition gradient programmer and former normally intended for HPLC use. At low flow rates in fluid line 952 (FIG. 13) and at low percentages of modifier composition, the flow rate in line 1508 will be slow enough so that it would be impractical to use selector-mixer 1540 to program a varying modifier composition. The volume of the mixing chamber in an Isco Model 2360 gradient programmer is on the order of 1 milliliter and if the flow rate in lead 952 were 1 milliliter per minute and the desired modifier concentration were 5%, the fluid demand on fluid line 1508 would be only 50 microliters per minute. However, programmable selector-mixer 1540 is very useful for scouting different mixed modifier compositions during development of supercritical extraction methods prior to routine use.

The mixer and selector 1540 has three fluid inlet lines 1541, 1544 and 1547 which dip into three different modifier liquids 1543, 1546 and 1549 contained in flasks 1542, 1545 and 1548. With this arrangement, the mixer and selector 1540 blends any combinations of these liquids and supplies them as an ongoing flow to the inlet of pumphead 1510.

The outlet 1571 of pumphead 1510 is lead to selector valve 1570 which in the position shown conducts fluid from pumphead 1510 through line 1511 to a third arm of tee 1506 where the modifier fluid is mixed with the liquid carbon dioxide, or other liquid which is to be converted by heating, to a supercritical fluid in extractor 1580. When changing solvent compositions with mixer-selector 1540, the valve 1570 is reset so that the lead 1571 connects to lead 1572 which vents the outlet of pumphead 1510 to waste. Pump 1509 is then run at a relatively high rate of speed purging its interior fluid wetted volume and the interior fluid wetted volume of mixer-selector 1540 and refilling them with the newly selected composition of fluid.

By this it can be seen how knowledge of the actual flow rate of liquid entering the extractor 1580 can be used to accurately and repeatably control a desired modifier concentration in the supercritical fluid.

The functions provided by the constant flow controller 1200 (FIG. 15), the gated flow pulse generator e.g. 1100 (FIG. 15) and the flow rate indicator/controller 1400 (FIG. 16) can be realized by discrete electronic circuitry or by the computer controller referenced in the parent application.

Figure 18:
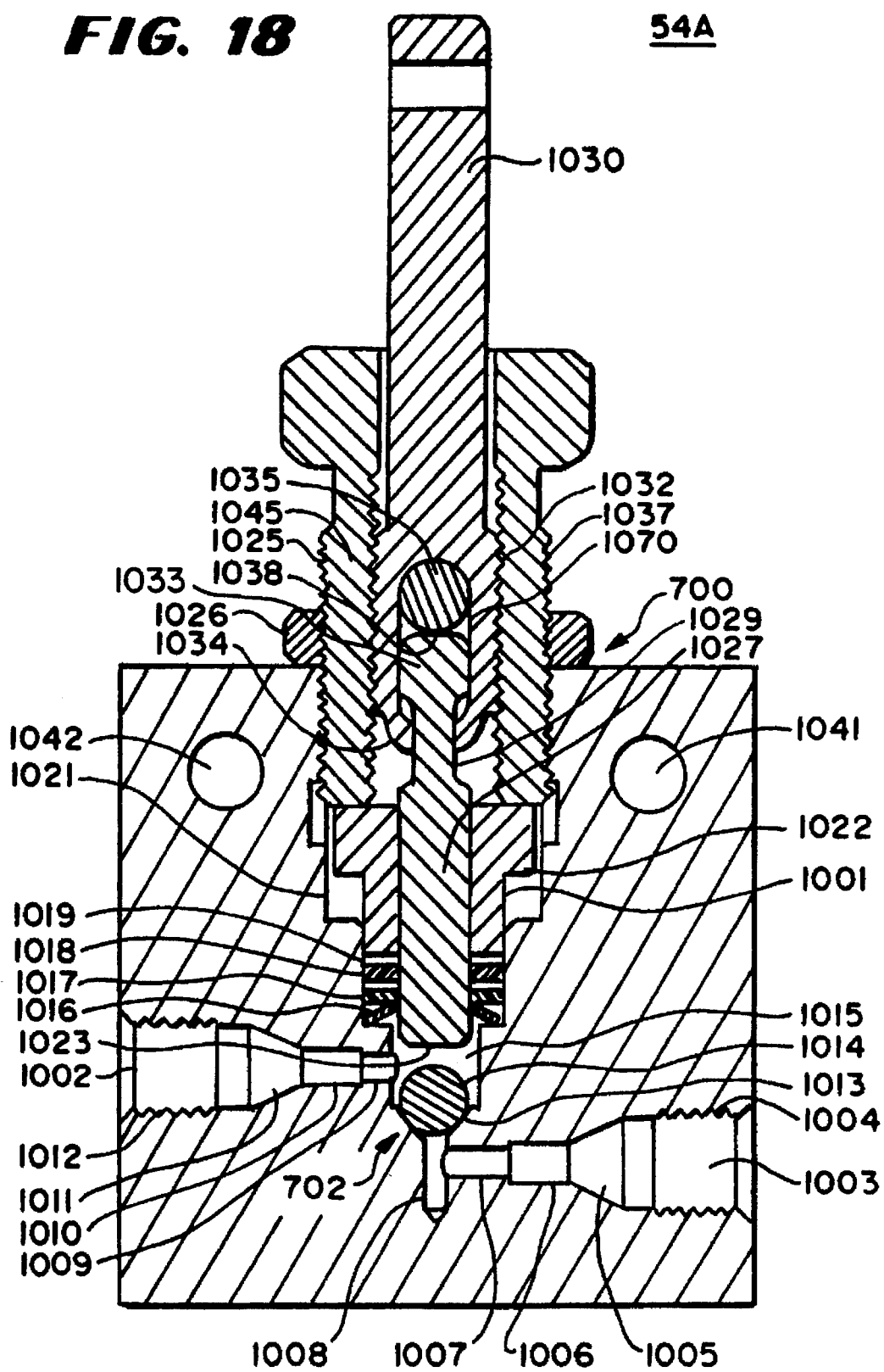
FIG. 18 is a cross-sectional elevational view of a valve useful in the invention.

In FIG. 18, there is shown a cross-sectional view of a valve 54A usable in the embodiments of this invention, having a valve body 1001, female fittings 1002 and 1003, a ball valve assembly 702 and a valve stem assembly 700. The female fitting 1003 is adapted to communicate with the pump 12 (FIG. 1) to receive supercritical fluid therefrom and the fitting 1002 is adapted to communicate with the pressure vessel and fluid assembly 18. The fitting 1003 and 1002', each communicating with each other through the ball valve assembly 702.

The valve stem assembly 700 is positioned to hold the ball valve assembly 702 closed in one position, thus blocking flow between the fitting 1003 and the fitting 1002 and in another position to release the valve ball assembly 702 so the fluid may flow from the pumping system 12 (FIG. 1) through the valve 54A and into the pressure-vessel and fluid-extraction assembly 18 (FIG. 1).

The ball valve assembly 702 includes passageways 1006, 1007, 1008, 1009 and 1010, a valve seat 1013, a valve element 1014 and a cavity 1015. The valve seat 1013 is initially machined as a female cone. The valve element 1014 is spherical and lies conformingly in the seat 1013 when it is forced into the seat as the valve is tightly closed, thereby forming a seal. When the valve is opened, the valve element 1014 may be lifted from the seat to permit communication between the fitting 1002 and 1003.

For this purpose, the valve seat 1013 communicates through the passageway 1008 at the bottom of the valve as a valve inlet and through the successively larger passageways 1007 and 1006 to the inlet female fitting 1003 to receive fluid underneath the valve seat capable of lifting the valve element 1014. The cavity 1015 is located above the valve element to communicate with the passageway 1008 when the valve element 1014 is lifted but to be sealed from it when it is closed at its bottom-most location. The cavity 1015 communicates through the successively larger passageways 1009 and 1010 with the outlet female fitting 1002 to permit fluid to flow from the female inlet fitting 1003 through the female outlet fitting 1002 when the valve element 1014 is permitted to rise into the cavity 1015 by the valve stem assembly 700.

The valve element 1014 must be harder on its surface and have a higher yield point than the valve seat 1013 and should be at least three times as hard as the seat 1013 on its surface. It should have a yield point of more than two times that of the seat and at least 40,000 psi since it must retain complete sphericity even though it rotates when it is lifted from the valve seat 1013 and is compressed by the stem into the valve seat 1013 when the valve 54A is closed by the stem assembly 700. The valve element 1014 must form a relatively large area of the seat to provide Hertzian line contact in order to form an adequate seal.

The valve seat 1013 is formed of the same material as the valve body 1001 and has a yield strength of at least 20,000 psi and preferably of about 85,000 psi. It is made of 316 stainless steel bar stock, hardened to about 85,000 psi yield strength by cold working to a 20 percent reduction in area. With this method of forming, the valve itself and the valve body 1001 is as small as one and one-eighth inch square by one-half inch thick. In the preferred embodiment, the valve element 1014 is approximately eight times as hard as the seat 1013 so that the seat 1013 deforms to fit the valve element 1014 rather than the valve element 1014 deforming. In this specification, hardness means compression yield point so that expressions such as eight times as hard mean that it has a yield point eight times higher. Because the materials are hardened throughout in the preferred embodiment rather than having only a surface hardening, the surface hardness is proportional to the yield point. Because the valve element 1014 is substantially harder the the seat, one or several tight closures of the valve force the valve element into the seat, thereby causing the seat to conform to the spherical surface of the valve element. The valve element is not deformed because it is too hard to do so.

To form a sufficiently strong valve element 1014, it is formed in the preferred embodiment of silicon nitride ceramic. Brittle balls, such as balls of monocrystalline sapphire and polycrystalline aluminum oxide ceramic, are generally less desirable and do not have the most useful hardness characteristics that permit sealing in the valve seat without leakage and resistance to scratching or breaking when lifted from the seat in a manner that causes rotation.

The valve element 1014 is one-eighth inch in diameter with a diametral tolerance of 100 micro-inches and a sphericity tolerance of 16 micro-inches. The close sphericity tolerance is desirable so that, after the ball rotates for more or less random reasons when the valve 54A is open, the sealing surface that is superimposed onto the conical seat 1013 by cold flow of the 316 stainless steel (due to the contact pressure or force of the ball 1014) continues to conform to the surface of the ball 1014. This conformance in shape with the contact surfaces prevents leaks when the valve 54A is closed. In the preferred embodiment, the ball 1014 has a hardness (compressive strength) of 500,000 psi (pounds per square inch).

Fittings for conducting fluids through the valve 54A are threaded into the female fittings 1002 and 1003 in a manner to be described hereinafter. Tapered sections or cones of the female fittings 1002 and 1003, shown respectively at 1011 and 1005, receive sealing ferrules to seal the connecting tubings protruding from the ferrules in the passageways 1010 and 1006. The internal threads are shown at 1012 and 1004, respectively, to engage the external threads on the corresponding male fittings.

The valve stem assembly 700 includes an outer stem 1030, an inner stem 1027, a hard anti-friction device 1035, a captivating element 1034, a spring 1016, a stepped bushing 1022 and a threaded bushing 1045. The outer stem 1030 fits rotatably within the threaded bushing 1045 with external threads on the outer stem 1030 engaging internal threads on the threaded bushing 1045.

Beneath the outer stem 1030 is the captivating element 1034 which holds an upper part of the inner stem 1027. Between the inner stem 1027 at its top point and the outer stem 1030 is the anti-friction device 1035 which is a hard ball that contacts the inner stem at a relatively small location and the outer stem 1030 over a wider area to provide a connection capable of pushing the inner stem 1027 downwardly but unlikely to transmit rotating forces between the outer stem 1030 and the inner stem 1027. The spring 1016 biases the inner packing support upwardly, compressing washer-shaped packing 1018 against the stem 1027. The inner stem 1027 is supported for up and down movement within the stepped bushing 1022. With this arrangement, rotation of the outer stem 1030 causes it to move downwardly within the threaded bushing 1045 to cause the anti-friction device 1035 to press the inner stem 1027 downwardly through tightly fitting packing 1018. The inner stem 1027, as it moves downwardly, presses the valve element 1014 into the valve seat 1013 and when it moves upwardly, releases the valve element 1014. The larger opening of the conical seat 1013 is large enough in diameter and the recess 1015 is small enough in diameter so that the ball, when pressed by the face 1023 of stem 1027, will find its way into the seat regardless of fluid flowing outwardly from the larger opening of the seat and regardless of the orientation of the valve with respect to gravity.

Above the cavity 1015, is a larger, one-fourth inch diameter, cylindrical recess 1019. In recess 1019, is the Bellville stainless steel spring 1016 made of highly work-hardened type 302 stainless steel (Associated Spring Company part number B-0250-013-S), washer-shaped packing support washer 1017 and semi-hard packing or seal 1018. Bellville spring 1016 is sized to fit loosely within the one-fourth inch diameter recess 1019 and to fit loosely around the one-eighth inch diameter internal stem 1027. The spring 1016 bears upwardly on the packing support washer 1017 and downwardly on the wall of the recess 1019. Packing support washer 1017 is made of Armco Nitronic® 60 stainless steel to prevent galling due to moving contact with the internal stem 1027. The annularly-shaped semi-hard seal 1018 is positioned between the packing support washer 1017 and the bottom of the stepped bushing 1021. It is dimensioned to sealingly fit the cylindrical wall of recess 1019 and is annularly shaped with its central hole dimensioned to sealingly fit the circumference of the one-eighth inch diameter inner stem 1027.

The semi-hard stem seal 1018 is made of DuPont Vespel type SP-211. Vespel is a trademark of DuPont for a temperature-resistant thermosetting polyimide resin reinforced with carbon and internally lubricated with Teflon polytetrafluorethylene powder (Teflon is a trademark of DuPont). Various softer seals made of plain and reinforced polytetrafluorethylene (PTFE) were tried, but had inadequate life at high temperatures and pressures. A seal with a hardness greater than 4000 psi, and which retains its hardness better than PTFE at high temperature, such as Vespel SP-211, is necessary.

The internal stem 1027 is made of age-hardened, cold drawn Type 17-7 PH stainless steel. Internal stem 1027 is guided by stepped bushing 1022 made of Nitronic 60 stainless steel. Nitronic 60 is used to prevent galling due to the motion of the contacting internal stem 1027.

There is a distinct relationship between the compressive yield strengths or hardnesses of the internal stem 1027, the very hard ball 1014 and the conical seat 1013. The ball 1014 must be substantially harder than the face 1023 of stem 1027, and the stem 1027 must be substantially harder than the seat 1013.

This is because when the valve closes tightly the ball 1014 must deform a relatively large area of the seat (a so-called Hertzian line contact) in order to seal, but the ball 1014 is in contact with a smaller area on the stem 1027 (a so-called Hertzian point contact). The ball's contact pressure on the stem 1027 is higher than its contact pressure on the seat 1013 because its contact area on the seat 1013 is larger. Nevertheless, the ball 1014 must not too greatly deform into (press too large a dimple into) the face 1023 of the stem 1027, or stem 1027 will swage outwards and interfere with or rub hard on washer 1017. Hence, stem 1027 must have a significantly higher yield point than conical seat 1013. Furthermore, ball 1014 should have a significantly higher yield point than stem 1027 so that the permanent contact dimple is on the stem face 1023 and not on the ball 1014.

Ball 1014 must retain almost perfect sphericity, as it is free to rotate when the valve is open and if it has a contact dimple it can produce a leak at the seat 1013 when the valve is closed.

The internal stem 1027 has a neck 1029 and a head 1033 which cooperates with captivating element 1034 of outer stem 1030. Head 1033 resides in cylindrical recess 1070 of outer stem 1030. The anti-friction device or hard ball 1035 transmits thrust from the female conical face 1036 of outer stem 1030 to the flat surface 1038 at the end of head 1033.

Before assembly of the head 1033 of inner stem 1027 and hard ball 1035 into outer stem 1030, captivating element 1034 is straight rather than curved and extends as a hollow cylinder with its extended interior diameter being part of the cylindrical recess or cavity 1070. At the final part of its assembly process, captivating element 1034 is bent, as shown in the figure, by a spinning or rotary swaging process. Outer stem 1030 is made of Type 17-4 PH age-hardened stainless but it not as hard as the interior stem 1027. The 17-7 PH stainless stem 1027 and its face 1023 has a hardness of 170,000 psi.

The face 1023 of stem 1027 should have a yield point and hardness at least 1.3 times higher than the seat 1013 and no more than 0.7 times as high as the yield point and hardness of the ball 1014. Screwing the stem 1030 counterclockwise relieves the force between the stem face 1023 and the ball 1014 and the ball 1014 is dislodged by any excess pressure present in fluid entering the location 1003, said fluid then exits through location 1002 and is prevented from leaking up through the valve stem area by the spring and fluid pressure loaded semi-hard seal 1018.

Because the yield strength of the 17-7 PH stainless steel at the face 1023 of the inner stem 1027 is only about 250,000 psi and the yield strength of the silicon nitride ball 1014 is about 500,000 psi, the rotation of the stem 1027 would be expected not to have a detrimental effect on the very hard ball or element 1014. Nevertheless, rotation of the stem 1027 surprisingly puts microscopic scars on the ball 1014 at the location of the interface between the ball 1014 and the stem end 1023. When the ball 1014 rotates later for semi-random reasons when the valve is opened, and the valve is closed again, these microscopic scars interfere with sealing at the interface between the ball 1027 and the conical seat 1013. To avoid these scars, the inner stem 1027 is provided with an anti-rotation element such as the ball 1035.

In operation, the outer valve stem 1030 may be rotated by any means which may be conveniently coupled to the outer stem 1030 by a pin through hole 1046. Clockwise rotation of the stem 1030 causes it to move into the valve because of the external threads on outer stem 1030 in contact with internal threads in threaded bushing 1045 which meet in the face of stem 1032. Fine-series one-fourth by 28 threads are satisfactory. The threaded face of stem 1032 is lubricated with DuPont Krytox® 217 high temperature, high pressure lubricant which is composed of perfluoronated polyether oil, low molecular weight powdered polytetrafluorethylene thickener and powdered molybdenum disulfide high pressure solid lubricant. This lubricant was found to have the best high temperature resistance of six high pressure, high temperature lubricants tested. The threaded bushing 1045 is made of Nitronic 60 to prevent galling due to the pressure and motion of the threads 1032 of outer stem 1030.

As the outer stem 1030 moves inward, so does the inner stem 1027 (FIG. 18) because of force transmitted by ball 1035 (FIG. 18). Although outer stem 1030 rotates, inner stem 1027 does not rotate because of the weakness of the rotary frictional force due to the small diameter of the contact area between the ball 1035 and the top 1038 of the head 1033 (FIG. 7) of the inner stem 1027. This weak friction force is not sufficient to overcome the anti-rotation frictional force of the tightly compressed seal 1018 (FIG. 18) against the cylindrical surface of the inner stem 1027.

As clockwise rotation of outer stem 1030 continues, eventually the inner stem 1027 is pushed in enough so that its flat end or stem face 1023 contacts the very hard valve ball 1014. Further clockwise rotation of the outer stem 1030 forces very hard ball 1014 into seat 1013, conformally deforming seat 1013 to fit the ball 1014 and providing a tight seal against flow of fluid entering the female fitting 1003 (FIG. 18). Fourteen pound inches of torque on stem 1030 provide a tight seal. Conversely, when outer stem 1030 is rotated counterclockwise, outer stem 1030 moves outwardly by action of its threads. Captivating element 1034 of outer stem 1030 pulls outwardly on the head 1033 of inner stem 1027, disengaging the boss 1023 of inner stem 1027 from tight contract with valve element or ball 1014. This allows fluid to flow from port 1003 to port 1002 in the valve.

Figure 19:
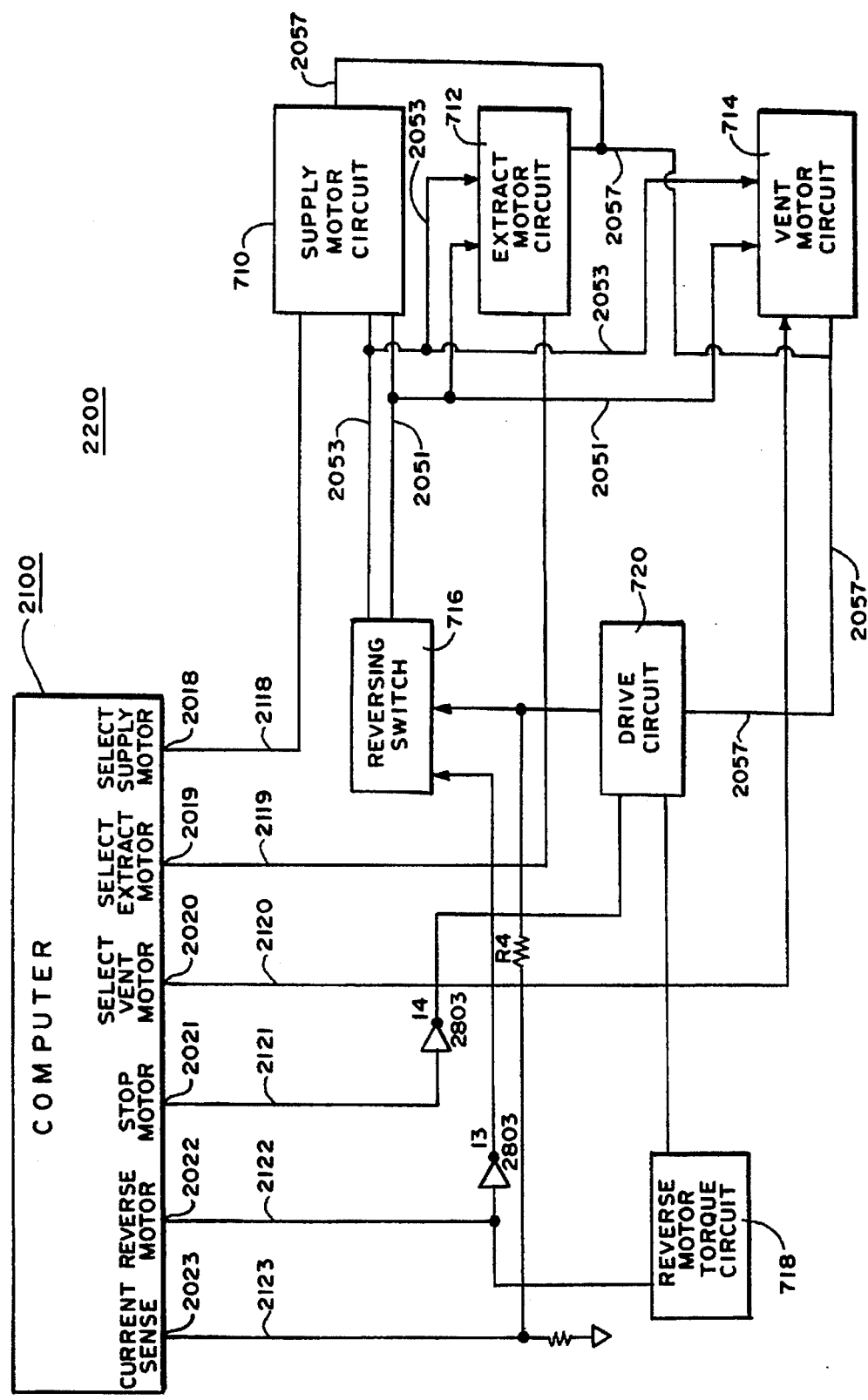
FIG. 19 is a block diagram of the circuitry for operating the system.

In FIG. 19, there is shown a block circuit diagram of the control circuitry 2200 for gear motor 570 (FIGS. 8, 9 and 10) which operates supercritical fluid supply valve 54A (FIG. 6), gear motor 574 (FIG. 5) which operates extraction valve 50A (FIG. 5), and gear motor 573 (FIG. 4) which then operates valve 52A (FIG. 4).

The control circuitry 2200 includes a programmer or other computer 2100, controlling a supply motor circuit 710, an extract motor circuit 712 and a vent motor circuit 714 to control the valves 54A (FIG. 6), 50A (FIG. 5) and 52A (FIG. 4), respectively, a reversing switch 716, a drive circuit 720 and a reverse motor torque circuit 718. The computer 2100 is electrically connected to the supply motor circuit 710, the extract motor circuit 712 and the vent motor circuit 714 through conductors 2118, 2119 and 2120 electrically connected to output terminals of the computer 2100.

The drive circuit 720 supplies power to a reversing switch 716 that is also electrically connected to the supply motor circuit 710, the extract motor circuit 712 and the vent motor circuit 714 to apply power to the selected one of those motors with a polarity that controls the direction of movement of the motors to open a valve or close a valve. The reversing switch 716 is electrically connected to conductor 2122 from a port 2022 in the computer to activate the reverse direction for closing the valve. This port is electrically connected to the reverse motor torque circuit 718 which controls the amount of torque in opening the valve and is for that purpose electrically connected to the drive circuit 720. A feedback circuit on conductor 2057 is electrically connected to the supply motor circuit 710, extract motor circuit 712 and vent motor circuit 714 to provide a feedback signal to the controller which controls the stopping of the motor when the valves close fully. The stop motor signal comes from conductor 2121 from the port 2021 in the computer or programmer 2100.

In the preferred embodiment, a programmable computer with timing circuits is utilized. It is the same computer used to operate the embodiment of FIG. 3. However, a manual switch can be used instead which switch is connected to a positive voltage supply to energize the corresponding motor when closed.

The control circuit 2200 includes a supply motor circuit 710, an extract motor circuit 712, a vent motor circuit 714, a computer or programmer 2100, a reversing switch 716, a drive circuit 720 and a reverse motor torque circuit 718. The supply motor circuit 710, extract motor circuit 712 and vent motor circuit 714 open and close corresponding ones of the valves 54A, 50A and 52A.

To control the valves, the computer or programmer 2100 has a plurality of output conductors that determine which valve is to be moved and the direction in which it is to be moved. This, in the preferred embodiment, is the computer which operates the extractor 10A (FIG. 3) but may be any timing device or indeed, instead of a programmer, manual switches may be used to close circuits to 15-volt DC voltages to open and close the valves as desired by an operator.

In the preferred embodiment, conductors 2118, 2119 and 2120 are connected to outputs 2018, 2019 and 2020, respectively, of the computer or programmer 2100 and to corresponding ones of the supply motor circuit 710, extract motor circuit 712 and vent motor circuit 714 to select those valves for opening or closing. A low-level signal on lead 2127 attached to computer output port 2021 is electrically connected through inverter 2026 to the drive circuit 720 to cause it to supply power to the selected valve through the reversing switch 716 which is electrically connected to the port 2023 through conductor 2123 to the reversing switch 716 and drive circuit 712.

The reversing switch 716 is electrically connected through conductors 2053 and 2051 to each of the supply motor circuits 710, extract motor circuit 712 and vent motor circuit 714 to supply the drive power thereto with the proper polarity for opening or closing the valves. The reverse motor port 2022 of the computer 2100 is electrically connected through conductor 2122 to the reverse motor torque circuit 718 and to the reversing switch 716 to select the polarity of electrical power to supply through conductors 2053 and 2051 to the selected one of the supply motor circuit 710, extract motor circuit 712 and vent motor circuit 714 to cause the motor to move the valve into the open position or closed position.

A torque adjustment feedback circuit connected to each of the motor circuits 710, 712 and 714 generates a potential which is fed back through conductor 2057 to the drive circuit 720, and in conjunction with the current sense signal on lead 2123 and the stop motor conductor 2121 from the computer 2100, determines when the motor should stop at the close valve position. The setpoint of this meter stopping torque may be set at the motor (FIG. 20) and may advantageously be programmed into the computer 2100 (FIG. 19). The reverse motor torque circuit increases the power supplied to the drive circuit 720 when the motors are moving in the direction that opens the valve to overcome overtightening due to differential expansion due to a temperature change since the valve was last closed, which may tend to keep the valve closed and to ensure opening of the valve on command.

Figure 20:
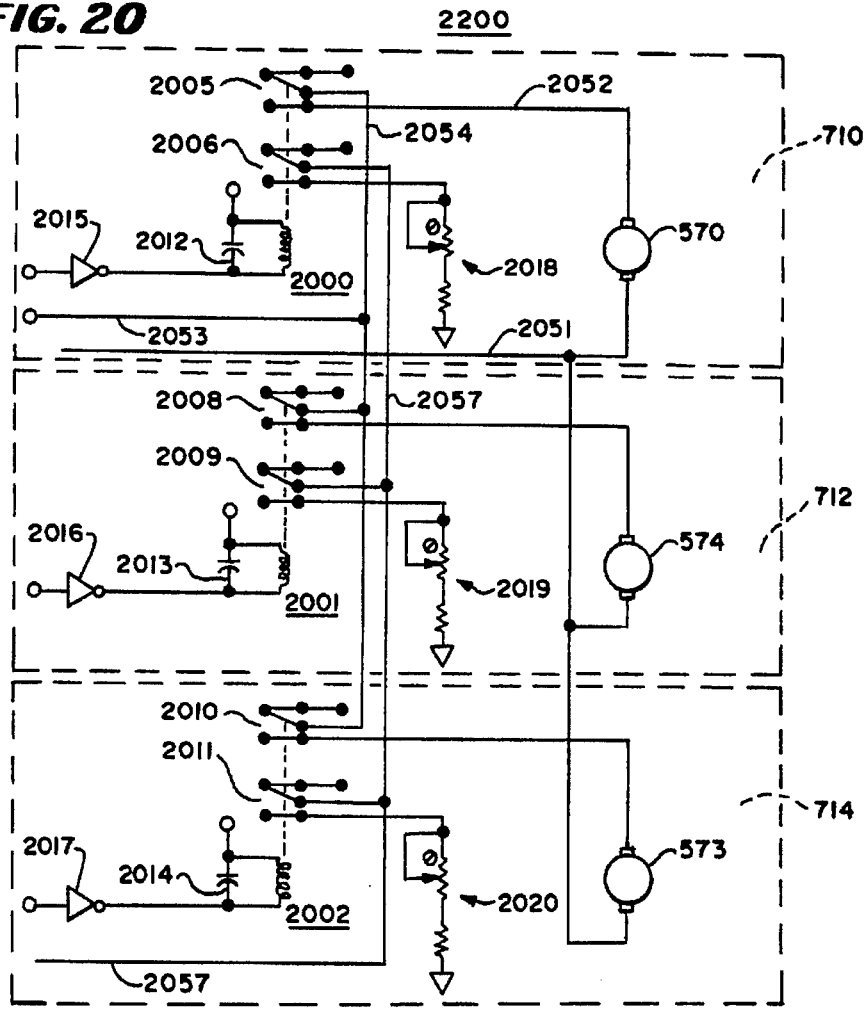
FIG. 20 is a schematic circuit diagram of a portion of the block diagram of FIG. 19.

In FIG. 20, there is shown a schematic circuit diagram of the supply motor circuit 710, extract motor circuit 712 and vent motor circuit 714 having gear motor 570, gear motor 574 and gear motor 573, respectively. Gear motor 570 is electrically selected by relay 2000, gear motor 574 is electrically selected by relay 2001 and gear motor 573 is electrically selected by relay 2002. Gear motor 570 controls or regulates the position (in this case, open or closed) of valve 54A (FIG. 6), gear motor 574 similarly controls valve 50A (FIG. 5) and gear motor 573 similarly controls valve 52A (FIG. 4).

The computer or programmable controller 2100 is the same computer controller or programmable controller that automates the other functions of the automatic extraction apparatus shown in FIG. 3. This conventional computer or programmable controller 2100 may be conventionally programmed to carry out any one of a variety of extraction protocols, including control of the valves. Computer 2100 has output ports 2018, 2019, 2020, 2021 and 2022 shown in FIG. 11. It also has input port 2023. Output port 2018 controls relay 2000 through inverter 2015. All of the inverters used in FIG. 11 are Type 2803 devices with open collector outputs. Output port 2019 controls relay 2001 through inverter 2016. Output port 2020 controls relay 2002 through inverter 2017.

Figure 21:
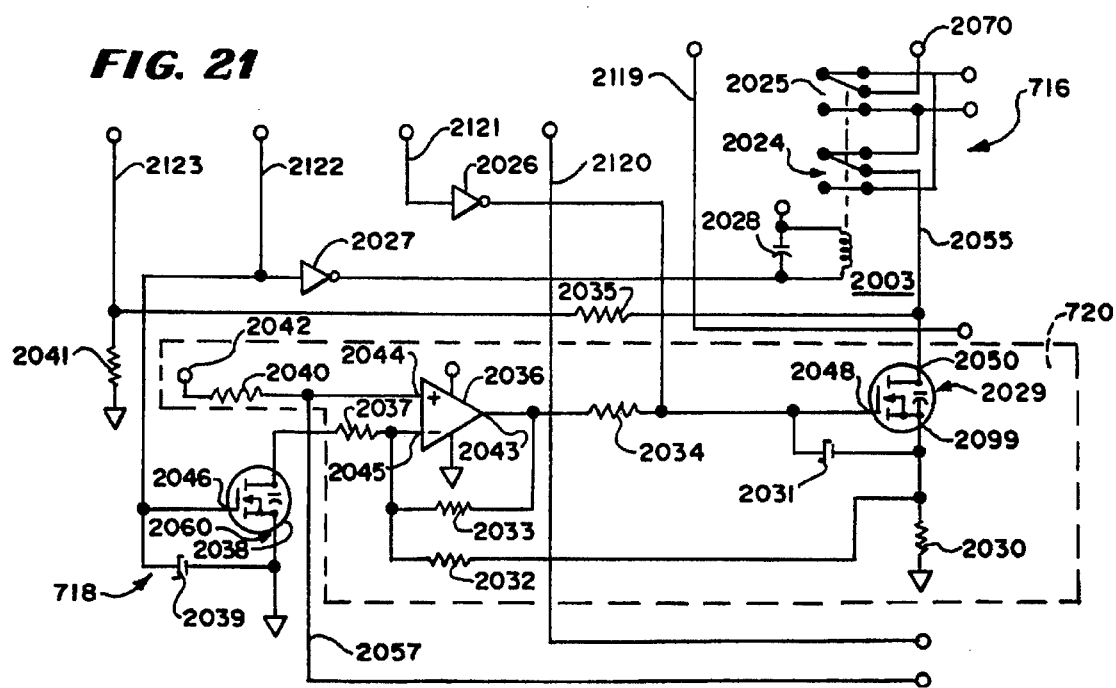
FIG. 21 is a schematic circuit diagram of another portion of the block diagram of FIG. 29.

In FIG. 21, there is shown a schematic circuit diagram of the reversing switch 716, reverse motor torque circuit 718 and drive circuit 720 of the control circuitry 2200. As best shown in this circuit, the output port 2022 controls relay 2003, of the reversing switch 716, through inverter 2027. Relay 2003 has its contacts wired in a conventional double-pole double-throw reversing circuit. It is used to reverse the voltage applied to whichever of the three gear motors is selected by relays 2000, 2001 or 2002 (FIG. 12).

To control torque, the control circuitry 2200 includes an operational amplifier 2036 and a power field effect transistor 2029 that provide current control (and therefore torque control) of the selected gear motor. Operational amplifier 2036 is a type 324 and power FET 2029 is a Type MTP12N06. Contacts 2024 of relay 2003 connect the drain 2050 of the power FET 2029 to one of the electrical terminals of the three gear motors 570 (FIG. 6), 574 (FIG. 5) and 573 (FIG. 4), and the motor selected by relay 2000, 2001 or 2002 (FIG. 12). Therefore, motor current flows through power FET 2029 and through current sensing resistor 2030 to circuit common.

The voltage drop across current sensing resistor 2030 is applied to the inverting input 2045 of operational amplifier 2036. The output 2043 of the operational amplifier 2036 is led through resistor 2034 to the gate 2048 of the power FET 2029. Resistors 2030 and 2032, the operational amplifier 2036 and the power FET 2029 provide a negative feedback or servo loop which is used to set the maximum current (and therefore the maximum torque or torque limit) of the gear motors. Resistor 2033 is connected between the output 2043 of the operational amplifier 2036 and sets the gain or proportional band of the servo loop.

The current setpoint is established by the voltage at the noninverting input 2044 of the operational amplifier 2036. A positive 2.5 volts reference voltage is applied to terminal 2042 and is led to the noninverting input through resistor 2040. The same relays 2000, 2001 and 2002 that select one of the three gear motors 570, 574 and 573 (FIG. 12) also simultaneously select an adjustable resistor corresponding to each gear motor. Adjustable resistor 2018 corresponds to gear motor 570, adjustable resistor 2019 corresponds to gear motor 574, and adjustable resistor 2020 corresponds to gear motor 573. Different nominally similar gear motors have somewhat different current-to-torque characteristics and the torque limit must be set separately for each gear motor.

Variable resistances 2018, 2019 and 2020 corresponding respectively to gear motors 570, 574 and 573 are respectively selected by relay contacts 2006, 2009 or 2011. The contacts 2006, 2009 and 2011 connect the selected variable resistance to conductor 2057 which is connected to the resistor 2040 and the noninverting terminal 2044 of the amplifier 2036. The voltage at inverting input 2045 equals the voltage at noninverting input 2044 when current or torque limiting is taking place.

The voltage across resistor 2030 is nearly the same as the voltage at the inverting input 2045, so changing the resistance of the variable resistances 2018, 2019 or 2020 during current limiting, varies the voltage across resistor 2030, and varies the limiting current through resistor 2030, which is the same as the current through the selected gear motor. The output port 2022 of the computer 2100 (FIG. 11) is also connected to the gate electrode 2046 of field effect transistor 2038. The source 2060 of the field effect transistor 2038 is connected to circuit common and its drain is connected to the inverting input 2045 of the operational amplifier 2036 through resistor 2037.

When the computer operates a selected motor in the reverse (valve-opening) direction, the voltage level at output port 2022 (FIG. 11) goes high, turning on field effect transistor 2038 through its gate 2046. This effectively connects the resistor 2037 between circuit common and the inverting input 2045 of the operational amplifier 2036. Resistor 2037 is approximately twice the value of resistor 2032, so it requires 1.5 times as much voltage across (and current through) resistor 2030 and the selected gear motor to bring the voltage at inverting input 2045 up to the voltage at noninverting input 2044.

The effect is to increase the torque limit by a factor of about 1.5 when the valve is opening as compared to when the valve is closing. This ensures that the valve does not stick if the opening torque is greater than the closing torque. It is surprising that such a jam can occur as it is known from experience that it takes less torque to reopen a valve than to close it. However, it is believed the reason for high opening torque is differential thermal contraction occurring when the valve is closed at a high temperature and then later opened at a significantly lower temperature.

It is desirable to shut off and turn on power to the gear motors 570, 574 and 573 (FIG. 12) by means other than the selector relays 2000, 2001 and 2002, and also to shut off power during a change of state of reversing relay 2003. It is desirable because these relays have longer life if their contacts switch (change state) at a time when no current is going through their contacts and because solid state power switching generates less electrical noise.

To this end the output port 2021 of computer 2100 (FIG. 11) provides a logic high level to shut off power FET 2029 through inverter 2026. A high level signal at output port 2021 (FIG. 11) is inverted by inverter 2026 and the resulting low level voltage is applied to the gate 2048 of power FET 2029, turning off the power FET 2029 and interrupting power to contacts 2024 and 2025 of relay 2003, contacts 2005 of relay 2000, contacts 2008 of relay 2001 and contacts 2010 of relay 2002. The computer 2100 (FIG. 7) is programmed so that the voltage level at output port 2021 (FIG. 11) goes high (power off) before the change of state of every relay and then goes low (power on) after a relay change of state.

When a valve is closing, the torque impressed on its gear motor starts to rise and the current through the gear motor starts to rise when the ball 1014 (FIG. 7) is forced into the conformal seat 1013. When the torque and current rise to the limit point described earlier, the voltage at the output 2043 of operational amplifier 2036 decreases. This decreased voltage is applied to gate 2048 of power FET 2029, and therefore the power FET 2029 starts to turn off. When this happens, the voltage at its drain 2050 and on the conductor 2055 starts to rise, causing current to flow through resistor 2035. Resistor 2041 forms a voltage divider with resistor 2035. The voltage division ratio is selected to indicate a torque limiting condition when the voltage on conductor 2055 produces a voltage at input port 2023 of computer 2100 (FIG. 11) which is equal to the logic level at that input port. This signals the computer 2100 that the valve has been closed.

Operation for a simple extraction procedure under programmable control is as follows with valves 54A (FIG. 6), 50A (FIG. 5) and 52A (FIG. 4) closed. Under computer control, gear motor 454 (FIG. 4) rotates high speed screw 476, elevating cartridge 30A into the extraction chamber within pressure vessel 24A (FIG. 4). The cartridge 30A positioned within the extraction chamber is shown in FIG. 6. Gear motor 600 drives locking mechanism 606 under computer control, effectively locking the extraction cartridge 30A within the extraction chamber (FIG. 6). The logic level at output port 2021 of computer 2100 (FIG. 19) has been high, shutting off power to all relay contacts. Then the logic level at port 2018 of computer 2100 (FIG. 19) goes high, turning on the coil of relay 2000 by action of the inverter 2015 (FIG. 20). Simultaneously, output port 2022 (FIG. 19) goes high activating relay 2003 (FIG. 21) through inverter 2027.

This places the contacts 2024 and 2025 of relay 2003 (FIG. 21) in the opposite position from that shown in FIG. 21. This is the reverse or valve-opening position. Simultaneously, the gate 2046 of FET 2038 goes high, turning on FET 2038.

After a fraction of a second, the logic level at port 2021 (FIG. 19) goes low, enabling the relay contact circuits by allowing power FET 2029 to turn on. A positive 15 volts at terminal 2070 is applied through contacts 2025 to place positive voltage on the bottom terminals (FIG. 19) of the gear motors 570, 574 and 573 (FIG. 20) which enables them to operate in reverse or in the direction which opens their associated valves. Positive voltage applied to the top terminals of these three motors enables closing of their respective valves.

Relay 2000 then selects the upper terminal of gear motor 570 through conductor 2052, contacts 2005 and conductors 2054 and 2053 (FIG. 20). Lead 2053 is connected to conductor 2055 through contacts 2024 since relay 2003 is activated. Lead 2055 is connected to the drain of power FET 2029 in the current limiting circuit. Since the motor requires less than the limiting current to open, it runs in the reverse (valve-opening) direction at a continuous speed of about 16 rpm, opening valve 54A (FIG. 6). After three seconds of such running and the corresponding opening of valve 54A, the computer 2100 causes output port 2021 (FIG. 19) to go high putting a low on the gate of power field effect resistor 2029 through inverter 2026 (FIG. 21). This stops current through the relay contacts and motor 570 (FIG. 20), and valve 54A (FIG. 7) remains open with the motor stopped. After a fraction of a second, port 2018 (FIG. 19) goes low turning off the relay 2000 which had selected motor 570 (FIG. 20).

The computer 2100 (FIG. 19) is programmed so a signal at its output port 2021 (FIG. 19) always shuts off the power FET current source transistor 2029 (FIG. 21) a fraction of a second before any of the relays 2000, 2001, 2002 (FIG. 20) or 2003 FIG. 21) change state. The computer 2100 is also programmed so that a signal at port 2021 re-enables the power FET 2029 a fraction of a second after a single or a group of simultaneous relay state changes, if power is needed at that time. Thus, none of these relays are required to switch any active current or power and their life is thereby prolonged. The operation of this protective feature is performed each time before and after each change of state of any of the relays.

In accordance with the above, gear motor 570 (FIG. 20) has opened valve 54A. This valve supplies supercritical fluid from a fluid line (not shown) attached to outlet port 308 of pumping system 1100 (FIG. 11) or pump 780 (FIG. 11); through fluid leads, lines or tubings 58A (FIG. 6) and 60A (FIG. 1) to the interior of the extraction chamber 24 (FIGS.

1, 2 and 3) and extraction cartridge 30A (FIG. 6). Then, computer output port 2019 (FIG. 19) goes high selecting relay 2001 through inverter 2016 (FIG. 20). Relay 2003 (FIG. 21) is still activated. Contacts 2008 of relay 2001 (FIG. 20) connect the upper conductor of motor 574 (FIG. 20) to conductor 2055 through contacts 2024 of relay 2003 (FIG. 21). This causes gear motor 574 to open valve 50A (FIG. 5). Valve 50A connects the outlet of the extraction cartridge 30A (FIG. 6) to restrictor tube 66A (FIG. 5) which leads to extractant collection vessel 98A. Three seconds after valve 50A starts to open, the computer 2100 causes the level at port 2019 (FIG. 11) to go low and motor 574 stops opening valve 50A, leaving valve 50A open.

Restrictor 66A (FIGS. 4 and 5) depressurizes supercritical fluid from the high pressure in extraction cartridge 30A (FIG. 6) to the lower pressure in collection vessel 98A (FIG. 4). The pressure in collection vessel 98A is usually comparatively close to atmospheric pressure and the supercritical fluid carrying dissolved sample usually has changed to a gas carrying entrained sample as it exits the restrictor 66A. Supercritical extraction of the contents of extraction cartridge 30A takes place as previously described.

A programmable timer within computer 2160 (FIG. 19) is set to the desired duration of the supercritical extraction. If the timer is set for ten minutes, then ten minutes after valve 50A (FIG. 5) opens, the extraction is complete. Output port 2022 of computer 2100 (FIG. 11) goes low, de-energizing relay 2003 through inverter 2027 (FIG. 13). De-energized contacts 2024 and 2025 of relay 2003 (FIG. 21) reverse the voltage to the gear motors 570, 574 and 573 (FIG. 20), enabling the gear motors to turn in the forward (valve-closing) direction. Field effect transistor 2038 turns off because of the low voltage on its gate 2046 (FIG. 13). Simultaneously, the computer causes its output port 2018 (FIG. 11) to go high, energizing relay 2000 through inverter 2015 (FIG. 20). Relay 2000 connects the upper terminal of gear motor 570 through conductor 2052, the relay contacts 2005, conductor 2054, conductor 2053 (FIG. 20), contacts 2025 of relay 2003 (FIG. 21) and to a positive 15 volt source at terminal 2070 (FIG. 20).

The lower terminal of gear motor 570 is connected through conductor 2051 (FIG. 20) to contacts 2024, conductor 2055 and drain 2050 of field effect transistor 2029 (FIG. 21) and from the source of the field effect transistor 2029 to resistor 2030. Contacts 2006 of relay 2000 connect variable resistance 2018 to conductor 2057 (FIG. 20) and then to noninverting input 2044 of operational amplifier 2036 (FIG. 21). Gear motor 507 now runs in the forward (valve-closing) direction with a current or torque limit set by variable resistance 2018 (FIG. 20).

As the valve closes tightly, pressing ball 1014 into conformal seat 1013 (FIG. 7), the motor torque and motor current increases, increasing the voltage across current sensing resistor 2030 (FIG. 21). As the torque and current increase a preset amount, the voltage on conductor 2055 (FIG. 21) becomes sufficiently high to reach the logic level of computer input port 2023 (FIG. 19) through the voltage divider composed of resistors 2035 and 2041 (FIG. 21). This causes the computer 2100 (FIG. 19) to bring the voltage at its output port 2018 low, de-energizing relay 2000 (FIG. 20). Then the computer brings the voltage at output port 2019 high. This energizes relay 2001 through inverter 2016, selecting gear motor 574 (which is coupled to valve 50A) and variable resistance 2014. Motor 574 rotates in the forward (valve-closing) direction closing the valve 50A (FIG. 5).

When the valve 50A (FIG. 5) is closed, the motor current increases until the voltage across current sensing resistor 2030 is approximately equal to the voltage at inverting input terminal 2045 of operational amplifier 2036 (FIG. 21), which is set by variable resistance 2019 associated with motor 574 (FIG. 20). This causes current and torque limiting which also causes the voltage of conductor 2055 (FIG. 21) to rise, in turn causing the voltage at current sensing input port 2023 (FIG. 11) to rise through the voltage divider comprised of resistors 2035 and 2041 (FIG. 13).

When the voltage at input port 2023 was the logic level of the computer 2100 (FIG. 19), the computer 2100 shuts off motor 574 (FIG. 20) at its predetermined torque limit. The voltage at output port 2019 goes low, de-energizing relay 2003 (FIG. 13) through inverter 2016 (FIG. 20). Output port 2022 (FIG. 11) goes high, energizing relay 2003 through inverter 2027 (FIG. 21). Energized contacts 2024 and 2025 (FIG. 21) enable gear motor 573 to open its high energizing relay 2002 through inverter 2017 (FIG. 20). Contacts 2010 and 2011 of relay 2002 select gear motor 573 connected to valve 52A (FIG. 4) and select variable resistance 2020 (FIG. 20) which sets the torque and current limit for gear motor 573. Gear motor 573 runs in the reverse (valve-opening) direction for three seconds opening valve 52A, which vents or discharges the pressure in the interior pressure vessel 24A and in extraction cartridge 30A (FIGS. 4 and 6).

After a suitable delay time to allow the pressure to reach a near-atmospheric value, gear motor 600 (FIG. 6) operates in reverse, unlocking the locking mechanism 606 (FIG. 6) under computer control. The gear motor 454 (FIG. 4) then rotates in reverse, causing high speed screw 476 to lower cartridge 30A from the extraction chamber within extraction vessel 24A.

Controlling the closing of the valves so that the valve stem motion stops when a torque limit is reached at the gear motor, is more desirable than closing the valve until a position limit is reached. This torque feedback limit control provides just enough force to close the valve. On the other hand, position control tends to either underclose the valve so that it leaks or overclose the valve so that excess unnecessary force causes unneeded wear of the seat.

The algorithm used to control the gear motor and open and close the corresponding valve is particularly useful as it is self-adjusting regardless of how far the inner stem 1027 forces the ball 1014 into seat 1013 (FIG. 18). Since the valve-opening torque is greater than the closing torque, the valve cannot stick closed and cause an erroneous "valve-open" condition within the computer or programmer. With repeated operation, the ball 1014 may be forced further and further into conical seat 1013 as the ball 1014 deforms a larger and larger area of the conical seat 1013 into a shape that conforms with the ball 1014. In closing the valve 54A, the gear motor always also forces the ball 1014 tightly into the seat 1013, shutting off the flow since the gear motor continues to run until attaining the torque limit which indiates leak tight seating of the ball 1014.

During opening of the valve 54A, the motor runs for a predetermined time which is equivalent to a predetermined angular rotation. This is because the motor runs in reverse at constant speed after the first fraction of one-thousandth of an inch of stroke of the inner stem 1027 (FIG. 18) while the stem 1027 is still applying force to the ball 1014 (FIG. 18). During all this time the motor runs with excess torque and is not unduly slowed down because the high logic level at computer output port 2022 (FIG. 11) is applied to the gate 2046 turning on field effect transistor 2038 (FIG. 13). As described previously, this sets a torque limit considerably higher than that necessary to loosen the ball 1014 from its seat 1013.

In operation, a program is entered into the control panel 410 (FIG. 4). This program is then stored in controller 450 (FIG. 4) and controls sample changing, fraction collection, static and/or dynamic extractions, fluid pressure, the steps or ramps of pressure, the supercritical fluid temperature, the elevation of the sample cartridge from the sampler reel up to the extraction chamber and return back to the sampler reel after extraction, locking and unlocking of the extraction chamber and operation of the three motor-operated valves in the manner described above to automatically duplicate the hand-operated functions of manual embodiments. In the alternative, the operations may be initiated from the keyboard by manually closing circuits to the motors as required to perform the desired sequence.

At the start of an extraction cycle, the extraction fluid valve 54A (FIGS. 6 and 7), purge valve 50A (FIG. 5), and the extractant valve 52A (FIG. 4) are closed. The sample reel 430 (FIG. 3) brings a selected extraction cartridge 30A into position under the extraction chamber 618 (FIG. 4). The extraction sample cartridge 30A within a sleeve 436 (FIG. 3) on reel 430 is positioned above the single hole 464 in the disk 462 (FIG. 4) and is supported on a spring-loaded support block 482 within the top of the piston 32A (FIG. 4).

To move the sample cartridge 30A (FIGS. 4 and 6) into the extraction chamber 618 (FIG. 4), the gear motor 454 (FIG. 4) causes the screw 476, piston 32A and cartridge 30A (FIGS. 4 and 6) to rise to the position shown in FIG. 6, inserting cartridge 30A and piston 32A into the pressure vessel 24A.

To lock the sample cartridge 30A in position, the gear motor 600 drives the pin 606 through the hole 609 in the pressure vessel 24A through the hole 610 in the piston 32A and through the hole 612 in the pressure vessel 24A (FIG. 6). This locks the piston into position within the pressure vessel 24A.

To remove extractant, the spring 201A under the block 482 (FIG. 4) forces the block 482 to push the sample cartridge 30A up against the bottom of the fitting 46A (FIG. 4). The gear motor 552 lowers the arm 560 carrying the restrictor tube 66A and the rack 406 (FIG. 3) into the position shown in FIG. 5, puncturing the cap 550 on the collection tube 98A. Alternatively, the collection tube 98A may be automatically raised to the restrictor tube 98A. The gear motor 570 (FIGS. 9, 10 and 12) rotates, opening the extraction fluid valve 54A (FIG. 6), admitting extraction fluid from a tube (not shown) connected to the outlet port 308 of pumping system 1100 (FIG. 11) or pump 780 (FIG. 12), through the heat exchanger 40A, tube 60A and the fitting 42A (FIG. 4).

The extraction fluid flowing through the fitting 42A enters the bottom of the extraction cartridge 30A (FIG. 4) and permeates the sample within it. If it is suspected that the outside cartridge 30A may be contaminated, the purge valve 52A is opened at this time under the control of the gear motor 573 (FIG. 4). This purges or flushes the space between the outer wall of the sample cartridge 30A and the inner wall of the pressure vessel 24A. Flushing fluid leaves the extraction chamber 618 outside of the cartridge 30A through the purge fitting 44A, tube 62A, Tee-joint tube 542, tube 620 (FIG. 4), Tee-joint tube 544, tube 548 and vent port 546 (FIG. 4).

After purging, the gear motor 573 closes the purge valve 52A (FIG. 4), terminating the purge operation. At this time, the controller 450 (FIG. 3) activates the gear motor 574 (FIG. 5) which opens the extractant valve 50A. Extractant fluid flows through the cartridge 30A, extracts material from the sample within the cartridge 30A, flows through the fitting 46A (FIG. 4), tubing 62A (FIG. 4), extractant valve 50A (FIG. 5), and to the restrictor tube 66A (FIG. 4). The restrictor tube 66A has a capillary bore of a small enough diameter to maintain the desired extraction pressure at the desired extraction fluid flow rate.

In case the extraction cartridge 30A (FIGS. 16 and 18) is not completely full of sample, it is beneficial to flow the extractant fluid downward through the cartridge 30A instead of upwards as in the foregoing example. Downward flow of extractant is accomplished by permitting the extractant to flow into the cartridge 30A through fitting 46A (FIG. 4) and from the cartridge 30A through fitting plug 32A (FIG. 4) and the fitting 42A (FIG. 4).

After extraction is complete and the extractant is collected in the trapping fluid 104A within the vial 98A (FIG. 5), the gear motor 570 (FIG. 6) shuts the extraction fluid valve 54A (FIG. 6). The gear motor 573 opens the purge valve 52A rapidly discharging the pressure and the extraction chamber 618 (FIG. 4). The gear motor 574 closes the extractant valve 50A and the gear motor 552 raises the arm 560 and restrictor tubing 66A and exhaust tubing 110A (FIG. 5). The gear motor 600 withdraws pin 606 from the holes 609, 610 and 612 in the pressure vessel 24A and the piston 32A (FIG. 6).

After the piston 32A has been unlocked, the gear motor 573 (FIG. 4) lowers the piston and sample cartridge 30A so that the sample cartridge 30A is lowered from being within the extraction volume 618 (FIG. 4) to being within the sleeve 436 of the sample reel 430 (FIG. 3). The gear motor 570 closes the purge valve 54A (FIG. 6).

After the valves have been closed and the sample cartridge 30A (FIGS. 4 and 6) returned to the sample reel, the sample reel 430 and the fraction collector reel 440 (FIG. 3) advance to bring another sample cartridge in another fraction collector vial into position.

As can be understood from the above description, the supercritical extraction technique has several advantages, such as for example: (1) it is more convenient than prior art extractors; (2) it automates the sample injection and fraction collection part of the extraction process as well as automating the extraction itself; (3) it is smaller and more compact because of the air-thermoelectric cooling the pumphead and the inlet fluid separately and simultaneously being water cooled; (4) it may have a reasonably high flow rate; (5) seal life is lengthened by improving the alignment of the plunger within the seal; and (6) fluid volume leaving the pump is precisely measured.

Although a preferred embodiment of the invention has been described in some detail, many modifications and variations of the preferred embodiment can be made without deviating from the invention. Therefore, it is to be understood that within the scope of the appended claims the invention may be practiced other than as specifically described.

We claim:

1. A pumping system for pumping and pressurizing a fluid used in supercritical fluid extraction comprising:

means connected to said pumping system for supercritical fluid extraction;

a rotating cam means having a cam with displacement slopes and a cooperating cam follower which varies the volume within a pumping chamber whereby said pumping chamber has within it liquid under pressure;

said pumping chamber including an inlet valve and an outlet valve;

said rotating cam having a repressurization surface, a delivery surface, a transition surface, a depressurization surface and a refill surface positioned to be traversed by the said cam follower in that order;

said depressurization surface having an initial displacement slope substantially equal to, but of the opposite sign of, the displacement slope of the final part of the delivery surface;

said transition surface being rounded sufficiently to allow closing of the said outlet valve without damage and to keep Hertzian contact forces between the cam and cam follower low enough to prevent deformation;

said depressurization surface being shaped to produce a continuously increasing linear velocity of the cam follower with respect to the cam rotation speed until the cam follower reaches the said refill surface, at which time the velocity the cam follower moves with a more constant linear velocity with respect to the cam rotation speed as it runs along the refill surface, whereby the fluid is pressurized by a maximum pressure by the pumping system and transferred to a heating means that converts said pressurized fluid to supercritical fluid.

2. A pumping system in accordance with claim 1 wherein the continuously increasing linear cam follower velocity of the depressurization surface corresponds to an acceleration of the linear velocity of the cam follower.

3. A pumping system in accordance with claim 1 wherein during the traversal of the depressurization surface, the displacement slope is inversely proportional to said pressure within the said pumping chamber when operating at the highest intended delivery pressure.

4. A pumping system in accordance with claim 1 in which the refill surface joins the depressurization surface without a discontinuity of slope and wherein the refill surface has a comparatively constant displacement slope.

5. A method of pumping for pumping and pressurizing a liquid used in supercritical fluid extraction to a maximum pressure which is conducted to a heating means that converts said pressurized liquid to supercritical fluid, comprising the steps of:

varying the volume within a pumping chamber with a rotating cam having displacement slopes and a cooperating cam follower wherein the chamber has within it liquid under pressure;

rotating said cam so that a repressurization surface, a delivery surface, a transition surface, a depressurization surface and a refill surface are traversed by the said cam follower in that order wherein said depressurization surface has an initial displacement slope substantially equal to, but of the opposite sign of, the displacement slope of the final part of the delivery surface; the transition surface being rounded sufficiently to allow closing of the said outlet valve without damage and keep Hertzian contact forces between the cam and cam follower low enough to prevent deformation; and said depressurization surface produces a continuously increasing linear velocity of the cam follower with respect to cam rotation speed until the cam follower reaches the said refill surface, at which time the velocity the cam follower moves with a more constant linear velocity with respect to cam rotation speed as it runs along refill surface.

6. A method of pumping in accordance with claim 5 wherein during the traversal of the depressurization surface, the said displacement slope is inversely proportional to said pressure within the said pumping chamber when operating at the highest intended delivery pressure.

* * * * *